US009388149B2

(12) United States Patent
Musicki et al.

(10) Patent No.: US 9,388,149 B2
(45) Date of Patent: Jul. 12, 2016

(54) DISUBSTITUTED 3,4-DIAMINO-3-CYCLOBUTENE-1,2-DIONE COMPOUNDS FOR USE IN THE TREATMENT OF CHEMOKINE-MEDIATED DISEASES

(71) Applicant: GALDERMA RESEARCH & DEVELOPMENT, Biot (FR)

(72) Inventors: Branislav Musicki, Nice (FR); Jerôme Aubert, Grasse (FR); Jean-Guy Boiteaux, Valbonne (FR); Laurence Clary, La Colle sur Loup (FR); Patricia Rossio, Grasse (FR); Marléne Schuppli-Nollet, Le Bar sur Loup (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/354,033

(22) PCT Filed: Oct. 26, 2012

(86) PCT No.: PCT/FR2012/052478
§ 371 (c)(1),
(2) Date: Apr. 24, 2014

(87) PCT Pub. No.: WO2013/061004
PCT Pub. Date: May 2, 2013

(65) Prior Publication Data
US 2014/0296254 A1   Oct. 2, 2014

Related U.S. Application Data

(60) Provisional application No. 61/552,940, filed on Oct. 28, 2011.

(30) Foreign Application Priority Data

Oct. 28, 2011   (FR) ...................................... 1159833

(51) Int. Cl.
| | | |
|---|---|---|
| C07D 407/06 | (2006.01) |
| C07D 409/06 | (2006.01) |
| C07D 409/14 | (2006.01) |
| C07D 307/14 | (2006.01) |
| C07D 307/54 | (2006.01) |
| A61K 31/341 | (2006.01) |
| A61K 31/381 | (2006.01) |
| A61K 31/4025 | (2006.01) |
| A61P 11/00 | (2006.01) |
| A61P 17/06 | (2006.01) |
| A61P 19/02 | (2006.01) |
| A61P 29/00 | (2006.01) |
| A61P 35/00 | (2006.01) |
| A61P 37/06 | (2006.01) |
| C07D 307/16 | (2006.01) |

(52) U.S. Cl.
CPC ............ *C07D 307/16* (2013.01); *A61K 31/341* (2013.01); *A61K 31/381* (2013.01); *A61K 31/4025* (2013.01); *C07D 307/14* (2013.01); *C07D 307/54* (2013.01); *C07D 407/06* (2013.01); *C07D 409/06* (2013.01); *C07D 409/14* (2013.01)

(58) Field of Classification Search
CPC .. C07D 407/06; C07D 405/06; C07D 409/06; C07D 409/14; C07D 307/14; C07D 307/16; C07D 307/54; C07D 405/14; C07D 407/14; C07D 413/14; A61K 31/381; A61K 31/341; A61K 31/351; A61K 31/4015; A61K 31/4025; A61K 31/4184; A61K 31/4192; A61K 31/422; A61K 31/4427; A61K 31/4709; A61K 31/506
See application file for complete search history.

(56) References Cited

U.S. PATENT DOCUMENTS

2010/0029670  A1 *  2/2010  Baettig et al. .............. 514/252.1

FOREIGN PATENT DOCUMENTS

| WO | WO 0208364 A1 * | 1/2002 | ............ B01J 23/468 |
| WO | 02/083624 A1 | 10/2002 | |
| WO | WO 2010015613 A1 * | 2/2010 | ............ C07C 311/48 |
| WO | 2010/063802 A1 | 6/2010 | |

OTHER PUBLICATIONS

Moreira et al. "Bioisosterism: A Useful Strategy for Molecular Modification and Drug Design" Curr. Med. Chem. 2005, 12, 23-49.*
Patani et al. "Bioisosterism: A Rational Approach in Drug Design" Chem. Rev. 1996, 96, 3147-3176.*
International Search Report dated Jan. 7, 2013 corresponding to International Patent Application No. PCT/FR2012/052478, 4 pages (with English translation).
Trivedi et al., "Gene Array Expression Profiling in Acne Lesions Reveals Marked Upregulation of Genes Involved in Inflammation and Matrix Remodeling", J Invest Dermatol, 2006, 1071-9, vol. 126.
Kang et al., "Inflammation and Extracellular Matrix Degradation Mediated by Activated Transcription Factors Nuclear Factor-kB and Activator Protein-1 in Inflammatory Acne Lesions in Vivo", Am J Pathol, 2005, 1691-9, vol. 166, issue 6.
Gonsiorek et al., "Pharmacological Characterization of Sch527123, a Potent Allosteric CXCR1/CXCR2 Antagonist", J Pharmacol and Exper Therapeutics, 2007, 477-485, vol. 322, issue 2.
Roth et al., "Magic shotguns versus magic bullets selectively non-selective drugs for mood disorders and schizophrenia", Nature Reviews Drug Discovery, 2004, 353-9, vol. 3.
Lipton, "Paradigm shift in neuroprotection by NMDA receptor blockade: Memantine and beyond", Nature Reviews Drug Discovery, 2006, 160-170, vol. 5.
Frantz, "Playing Dirty", Nature, 2005, 942-3, vol. 437.

(Continued)

*Primary Examiner* — Nyeemah A Grazier
*Assistant Examiner* — Amanda L Aguirre
(74) *Attorney, Agent, or Firm* — Dentons US LLP

(57) ABSTRACT

Disubstituted 3,4-diamino-3-cyclobutene-1,2-dione compounds are described that correspond to general formula (I). Also described, are pharmaceutical compositions that include these compounds and methods of using these compounds and compositions for the treatment of chemokine-mediated diseases.

10 Claims, 2 Drawing Sheets

(56) References Cited

OTHER PUBLICATIONS

Abd El All et al., "Immunohistochemical expression of interleukin 8 in skin biopsies from patients with inflammatory acne vulgaris", Diagnostic Pathology, 2007, 1-6, vol. 2, issue 4.

Kapur et al., "Does Fast Dissociation From Dopamine D2 Receptor Explain the Action of Atypical Antipsychotics?: A New Hypothesis", Am J Physchiatry, 2001, 360-9, vol. 158, issue 3.

Swinney, "Can Binding Kinetics Translate to a Clinical Differentiated Drug? From Theory to Practice", Lett Drug Design & Discovery, 2006, 569-574, vol. 3.

Swinney, "Applications of Binding Kinetics to Drug Discovery: Translation of Binding Mechanisms to Clinical Differentiated Therapeutic Responses", Pharm Med, 2008, 23-34, vol. 22, issue 1.

* cited by examiner

US 9,388,149 B2

DISUBSTITUTED 3,4-DIAMINO-3-CYCLOBUTENE-1,2-DIONE COMPOUNDS FOR USE IN THE TREATMENT OF CHEMOKINE-MEDIATED DISEASES

CROSS-REFERENCE TO PRIOR APPLICATIONS

This application is a National Stage of PCT/FR2012/052478, filed Oct. 26, 2012, and designating the United States (published in English on May 2, 2013, as WO 2013/061004 A1), which claims priority under 35 U.S.C. §119 to U.S. Provisional Application No. 61/552,940, filed Oct. 28, 2011, and French Patent Application No. 1159833, filed Oct. 28, 2011 each hereby expressly incorporated by reference in its entirety and each assigned to the assignee thereof.

FIELD OF THE INVENTION

The present invention relates to novel disubstituted 3,4-diamino-3-cyclobutene-1,2-dione compounds, to the pharmaceutical compositions containing these compounds and also to the use of these compounds and of these compositions for the treatment of chemokine-mediated diseases.

STATE OF THE ART PRIOR TO THE INVENTION

Chemokines or cytokines are small soluble proteins. Their most well-known role is the attraction of immune system cells and the control of the activation state of said cells. All chemokines perform their functions by binding to G protein-coupled receptors. Some chemokines are considered to be pro-inflammatory. The secretion of these chemokines can be induced during the immune response in order to promote the arrival of immune system cells at an infectious site.

There are two types of chemokines: pro-inflammatory chemokines and constitutive chemokines.

The pro-inflammatory (or "inducible") chemokines are produced at sites of inflammation by tissue cells or leucocytes that have infiltrated, after contact with a pathogenic agent.

The constitutive (or "homeostatic") chemokines are produced in the lymphoid organs and in certain non-lymphoid organs such as the skin and mucous membranes. They regulate lymphocyte trafficking and the localization of lymphocytes within these organs during lymphopoiesis, but also for maintaining immunosurveillance.

The nomenclature of these chemokine receptors is based on the group of chemokines to which its ligand belongs. Thus, the receptors corresponding to the chemokines of the CXC group are, for example, called CXCR1, CXCR2, CXCR3, CXCR4, etc., and the receptors corresponding to the chemokines of the CC group are, for example, called CCR1, CCR2, CCR3, etc. These receptors all have a similar tertiary structure, and they are coupled to a G protein: they are therefore part of the GPCR (G Protein-Coupled Receptor) superfamily. Interleukin-8 or IL-8 (also known as CXCL-8) is a member of the CXC chemokine family, which plays an essential role in the recruitment of neutrophils to the inflammation site. Two receptors, CXCR1 and CXCR2, are known to be specifically activated by IL-8. While CXCR2 binds with strong affinity to IL-8 and to the related chemokines, such as CXCL6, CXCL5, CXCL3, CXCL2 and CXCL1, CXCR1 binds only to IL-8. High levels of IL-8 and of related chemokines (CXCL5, CXCL2 & CXCL1) have been described in the lesions of inflammatory acne (J Invest Dermatol. 2006;126:1071-9; Am J Pathol. 2005;166(6):1691-9; Diagn Pathol. 2007 Jan 30;2: 4).

First indications demonstrate the expression of CXCR2 in inflammatory acne (Trivedi et al. J Invest Dermatol. 2006 126(5):1071-9). Thus, double antagonists of CXCR1 and CXCR2 might make it possible to rapidly reduce the harmful effects of the IL-8-mediated inflammatory response.

Patent application WO 02/083624 (Schering/Pharmacopeia) discloses more particularly substituted 1,2-cyclobutenedione compounds capable of modulating the activity of CXC-type chemokine receptors, and more particularly the activity of the CXCR1 and CXCR2 receptors. Among these compounds, the compound SCH-527123 (corresponding to example 360.71 on page 281), also called Navarixin, is in the process of being developed (Phase II) for the treatment of chronic obstructive pulmonary disease (or COPD). This compound has also been the subject of phase II studies in asthma and in psoriasis, but these developments have been stopped.

It is currently known that many pathologies of inflammatory type are mediated by chemokines. However, there is a need, which has not been satisfied to date, to treat the inflammatory component of the pathologies of interest in the dermatology field, for instance acne, rosacea or alternatively neutrophilic dermatosis, in particular psoriasis.

Likewise, the promise of obtaining effective new therapies for treating chemokine-mediated diseases using chemokine receptor antagonists has not been fulfilled. Indeed, several clinical studies have failed in phase II. One of the reasons which may explain these failures is the overlap of the biological effects of the various chemokines induced in a pathological situation. To date, the objective of the standard drug discovery process is to identify molecules which target a specific receptor without an off target effect. This approach is without doubt not the most suitable for treating complex inflammatory diseases. An increasing number of approaches appear to favor the search for antagonist molecules with a broad spectrum of action (promiscuous compounds), said approaches possibly thus proving to be more effective in treating complex and multifactorial diseases, (Franz S. Drug discovery: playing dirty. Nature. 2005 Oct. 13;437(7061):942-3; Roth B L, Sheffler D J, Kroeze W K. Magic shotguns versus magic bullets: selectively non-selective drugs for mood disorders and schizophrenia. Nat Rev Drug Discov. 2004 Apr. 3(4): 353-9).

As it happens, the applicant has discovered novel compounds which not only have an antagonist activity with respect to receptors of CXCR1 and CXCR2 type, but also a strong antagonist activity with respect to chemokine receptors, in particular CCR6 and CXCR3 receptors. These novel compounds surprisingly exhibit a polypharmacology, which makes them of additional interest compared with the already known compounds in the treatment of chemokine-mediated pathologies, and more particularly pathologies of dermatological type. Furthermore, these novel compounds exhibit a hepatic stability which is much lower than that of the already described compounds capable of blocking the activation of CXCR1 and CXCR2 receptors, for instance the SCH-527123 compound. This particular property provides the advantage of having novel compounds which, surprisingly, have a profile that is more suitable for the topical treatment of pathologies of dermatological type. Indeed, their hepatic instability leads to low, or even zero, systemic exposure, and therefore limited side effects. Another particularity of the compounds described in the present invention is their dissociation constant with respect to receptors of CXCR1 and CXCR2 type, said constant being much lower than that of the compounds described in the patent application WO 02/083624, for instance SCH-527123. Indeed, the SCH-527123 molecule has been described as having a dissociation time of about 22 h (pseudo-irreversible dissociation) (Pharmacological Characterization of SCH-527123, a Potent Allosteric CXCR1/CXCR2 Antagonist. JPET 322:477-485, 2007), whereas the dissociation times of the compounds of the present invention are much shorter.

Examples in the literature show that rapid dissociation of antagonists promotes a decrease in their toxicity. This has been described for the antagonists of dopamine D2 receptors (*Am J Psychiatry* (2001) 158(3):360-369), and of N-methyl-D-aspartate (NMDA) receptors (Nat Rev Drug Disc (2006) 5(2):160-170.) and also for nonsteroidal anti-inflammatory drugs (*Lett Drug Des Discov* (2006) 3(8):569-574. and *Pharm Med* (2008) 22(1):23-34). Indeed, a long dissociation time would instead have a tendency to induce adverse effects. With rapid dissociation times, the compounds according to the invention consequently exhibit reduced side effects.

SUMMARY OF THE INVENTION

Figure 1:
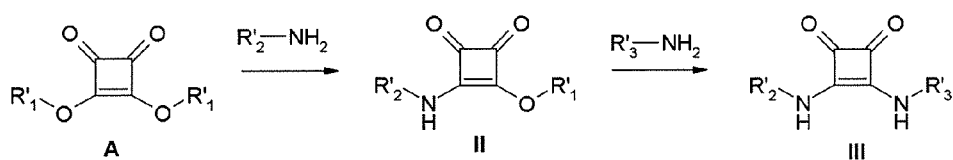
FIG. 1 is a scheme of a synthesis of the compounds of formula (III).
Figure 2:
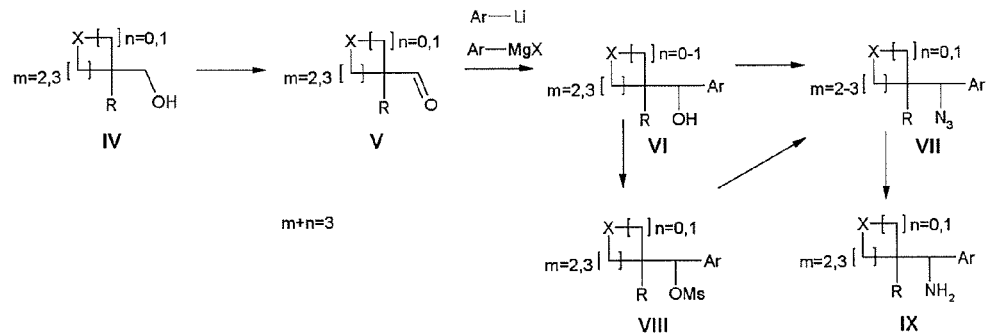
FIG. 2 is a scheme of a preparation of amines R'3-NH2 of formula (IX).
Figure 3:
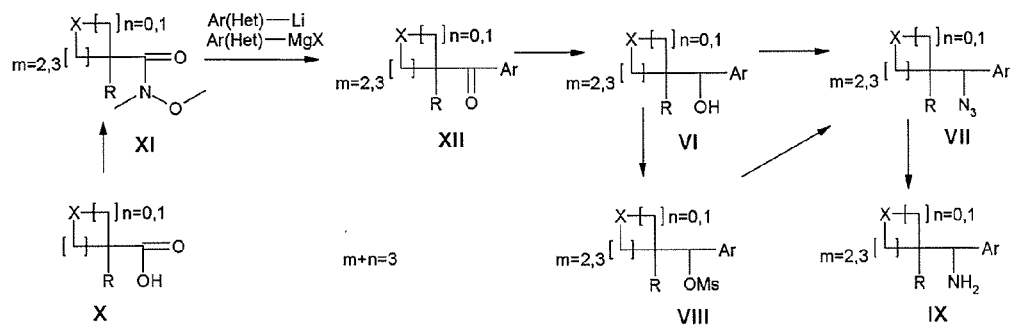
FIG. 3 is a scheme of an alternative preparation of amines R'3-NH2 of formula (IX).
Figure 4:
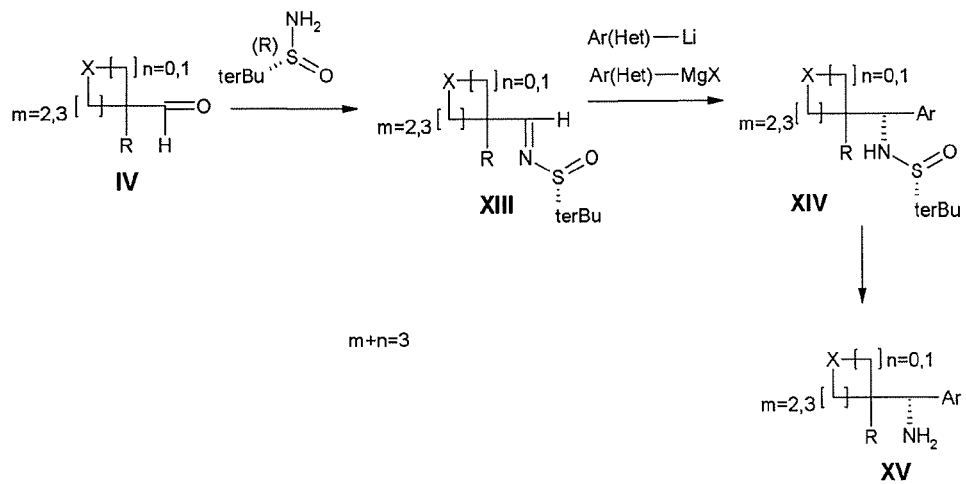
FIG. 4 is a scheme of a preparation of a chiral amine R'3-NH2 of formula (XV).
Figure 5:
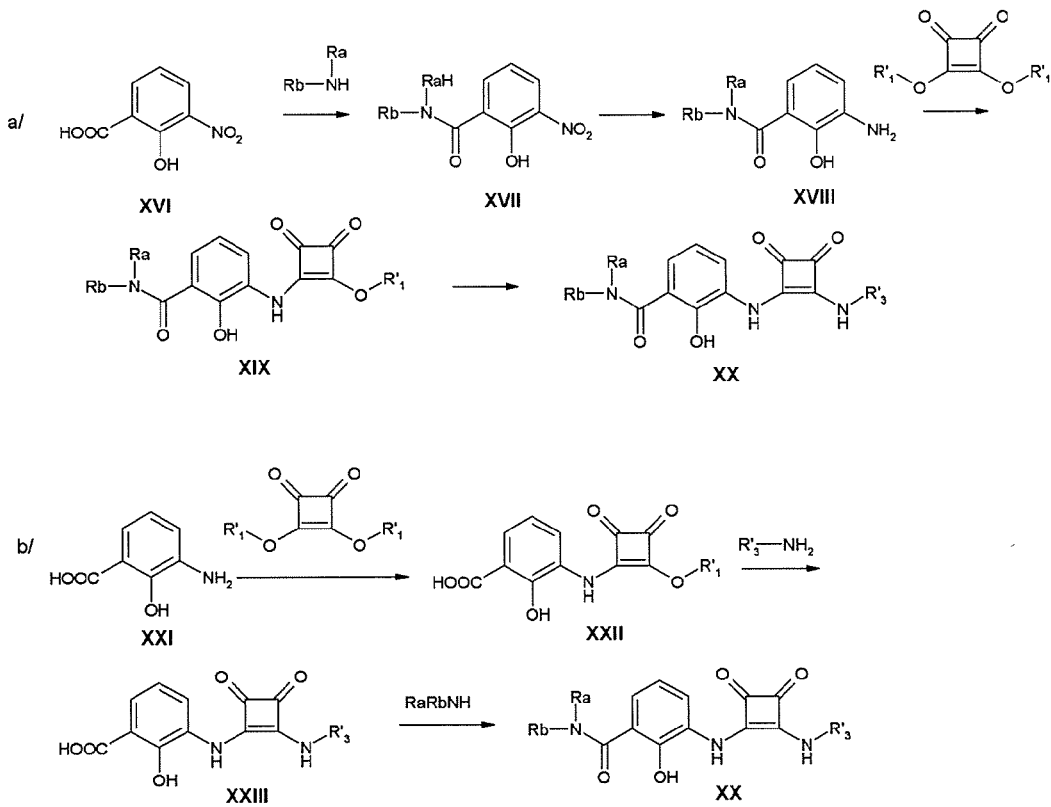
FIG. 5 is a scheme of a preparation of a compound of formula (XX).

A first subject according to the invention relates to novel disubstituted 3,4-diamino-3-cyclobutene-1,2-dione compounds corresponding to general formula (I) below:

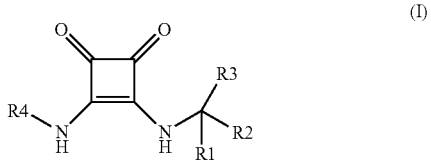

(I)

and also the pharmaceutically acceptable salts, solvates or hydrates thereof, for which the substituents R1, R2, R3 and R4 are as defined hereinafter in the detailed description of the invention.

A second subject according to the invention relates to a pharmaceutical composition comprising an effective amount of a compound corresponding to general formula (I), or of one of the pharmaceutically acceptable salts thereof or one of the pharmaceutically acceptable solvates or hydrates thereof, in combination with a pharmaceutically acceptable solvent or support.

A third subject according to the invention relates to a compound or a pharmaceutical composition as described above, for use as a medicament.

A fourth subject according to the invention relates to a compound or a pharmaceutical composition as described above, for use in the treatment of chemokine-mediated diseases.

A fifth subject according to the invention relates to a compound or pharmaceutical composition as described above, for use in the treatment of diseases of the group comprising neutrophilic dermatosis, and in particular psoriasis, atopic dermatitis, acne, rosacea, asthma, chronic obstructive pulmonary diseases, respiratory diseases in adults, arthritis, inflammatory bowel diseases, Crohn's disease, transplant rejection, cystic fibrosis and skin cancers.

DETAILED DESCRIPTION OF THE INVENTION

Unless otherwise indicated, the following definitions apply to the entire description and claims.

These definitions apply independently of whether a term is used alone or in combination with other terms. Thus, for example, the definition of the term "aryl" applies both to "aryl" as such and to the "aryl" part of the term "aryloxy".

"Alkyl" denotes a linear or branched, saturated hydrocarbon-based chain of which the number of carbon atoms is specified.

When the number of carbon atoms is not specified, this means that the alkyl chain contains from 1 to 20 carbon atoms.

The preferred alkyl radicals contain from 1 to 12 carbon atoms, and those which are even more preferred contain from 1 to 6 carbon atoms in the chain.

"Alkoxy" denotes an oxygen substituted with an alkyl radical as previously defined. Examples of alkoxy radicals include methoxy, ethoxy, n-propoxy, isopropoxy and n-butoxy radicals.

"Aryl" denotes a monocyclic or polycyclic (2 to 3 rings) aromatic cyclic system comprising from 6 to 14 carbon atoms, and preferably from 6 to 10 carbon atoms.

By way of examples of aryl radicals, mention may be made of phenyl, naphthyl, indenyl, tetrahydronaphthyl, indanyl, anthracenyl and fluorenyl radicals.

"Heteroaryl" denotes a monocyclic or polycyclic (2 to 3 rings) aromatic system comprising from 5 to 14 cyclic atoms, preferably from 5 to 10 cyclic atoms, in which one or more of the cyclic atoms represent(s) one or more (from 1 to 5) heteroatom(s) chosen from the group comprising nitrogen, oxygen and sulfur.

The preferred heteroraryls contain 5 or 6 cyclic atoms and 1 to 3 heteroatoms.

The prefix aza, oxa or thia before the name of the root heteroaryl signifies that at least one nitrogen, one oxygen or one sulfur is respectively present in the ring.

A nitrogen atom of a heteroaryl can be optionally oxidized to N-oxide.

By way of examples of appropriate heteroaryls, mention may be made of the following heteroaryls:

pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4 triazinyl and benzothiazolyl.

"Arylalkyl" denotes a radical of which the aryl and alkyl parts are as defined above.

By way of examples of arylalkyl, mention may be made of benzyl, phenethyl and naphthalenylmethyl radicals.

The linkage to the structure to which it is attached is via the alkyl radical.

"Heteroarylalkyl" denotes a radical of which the heteroaryl and alkyl parts are as defined above.

By way of examples of heteroarylalkyl, mention may be made of pyridylmethyl, pyridylethyl, imidazolylmethyl, imidazolylethyl, pyrazolylmethyl and pyrazolylethyl radicals.

The linkage to the structure to which it is attached is via the alkyl radical.

"Cycloalkyl" denotes a nonaromatic hydrocarbon-based cyclic system, having from 3 to 10 carbon atoms, preferably from 5 to 10 carbon atoms, and from one to three rings.

The preferred cycloalkyl radicals contain from 5 to 7 cyclic atoms.

By way of examples of cycloalkyl radicals, mention may be made of cyclopropyl, cyclopentyl, cyclohexyl, cycloheptyl, norbornyl and adamantyl radicals.

"Cycloalkylalkyl" denotes a radical of which the cycloalkyl and alkyl parts are as defined above.

By way of examples of cycloalkylalkyl, mention may be made of cyclopropylmethyl, cyclopropylethyl, cyclobutylmethyl, cyclobutylethyl, cyclopentylmethyl, cyclopentylethyl, cyclohexylmethyl, cyclohexylethyl, norbornylmethyl and adamantylmethyl radicals.

The linkage to the structure to which it is attached is via the alkyl radical.

"Heterocycloalkyl" denotes a nonaromatic hydrocarbon-based cyclic system, having from 4 to 10 carbon atoms, preferably from 5 to 10 carbon atoms, and from one to three rings, and comprising from one to three heteroatoms chosen from the group consisting of nitrogen, oxygen and sulfur.

The preferred heterocycloalkyl radicals contain from 5 to 7 cyclic atoms.

By way of examples of heterocycloalkyl radicals, mention may be made of tetrahydrofuranyl, tetrahydrothiophenyl, tetrahydropyranyl and 7-oxabicyclo[2.2.1]heptanyl radicals.

"Fluoroalkyl" denotes an alkyl radical as previously defined, substituted with one or more fluorine atoms.

By way of examples of fluoroalkyl radicals, mention may be made of fluoromethyl, difluoromethyl, 2-fluoroethyl, 2,2-difluoroethyl and 2,2,2-trifluoroethyl radicals.

"Perfluoroalkyl" denotes an alkyl radical as previously defined, in which each hydrogen atom has been substituted with a fluorine atom.

By way of examples of perfluoro radicals, mention may be made of trifluoromethyl and pentafluoroethyl radicals.

Thus, a first subject according to the invention relates to novel disubstituted 3,4-diamino-3-cyclobutene-1,2-dione compounds corresponding to general formula (I) below, or one of the pharmaceutically acceptable salts or solvates thereof:

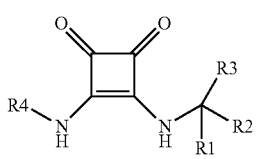

(I)

R1 represents a hydrogen atom or a methyl,

R2 represents a ring comprising five atoms, chosen from the structures (1), (2), (3) and (4) below:

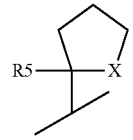

(1)

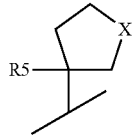

(2)

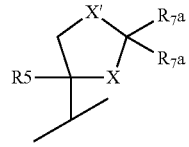

(3)

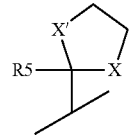

(4)

in which R5, R7a, X and X' have the meaning given hereinafter,

R3 represents an aromatic or heteroaromatic ring selected from the group consisting of the rings corresponding to formulae (a) to (o) below:

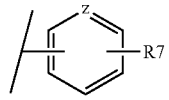

(a)

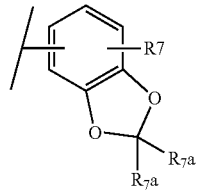

(b)

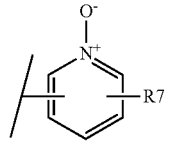

(c)

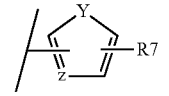

(d)

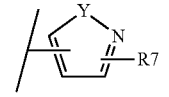

(e)

-continued

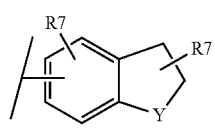 (f)

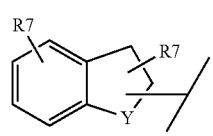 (g)

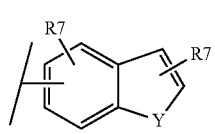 (h)

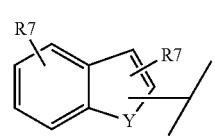 (i)

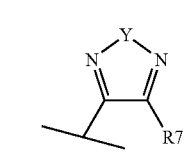 (j)

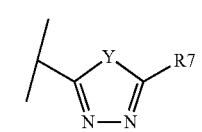 (k)

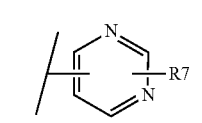 (l)

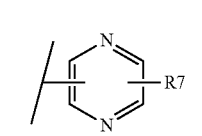 (m)

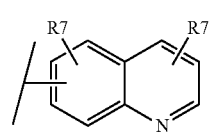 (n)

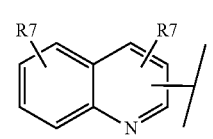 (o)

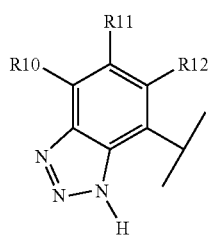 (p)

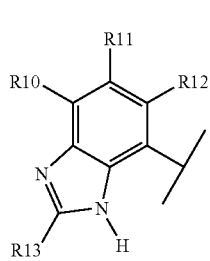 (q)

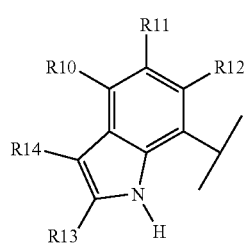 (r)

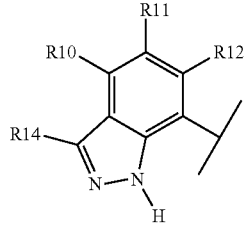 (s)

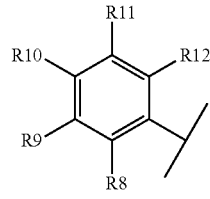 (t)

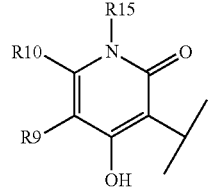 (u)

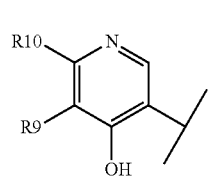 (v)

in which R7, R7a, Y and Z have the meaning given hereinafter, it being specified that the rings (a) to (o) can optionally bear several R7 groups, which may be identical or different, the total number of such R7 groups being at most equal to the number of substitutable atoms of the ring;

R4 represents an aromatic or heteroaromatic ring selected from the group consisting of the rings corresponding to formulae (p) to (z) and (aa) to (ak) below:

-continued

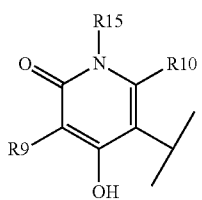
(w)

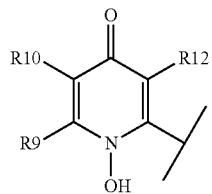
(x)

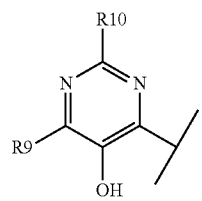
(y)

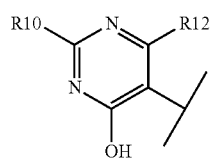
(z)

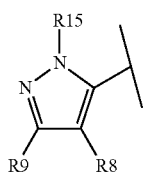
(aa)

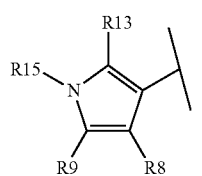
(ab)

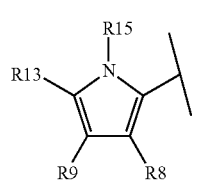
(ac)

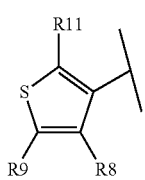
(ad)

-continued

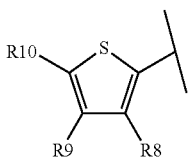
(ae)

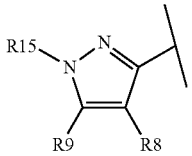
(af)

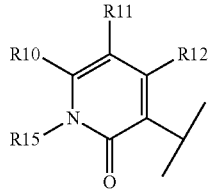
(ag)

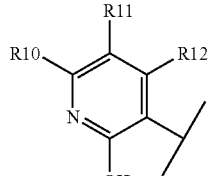
(ah)

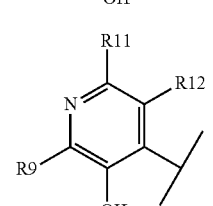
(ai)

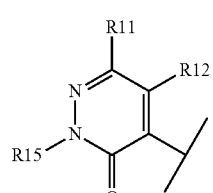
(aj)

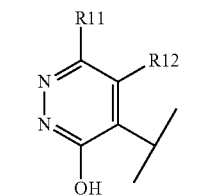
(ak)

in which R7, R8, R9, R10, R11, R12, R13, R14 and R15 have the meaning given hereinafter, R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a halogen, or an —R16, —CF₃, —COR16, —OR16, —NR16R17, —NO₂, —CN, —SO₂R16, —SO₂NR16R17, —NR16COR17, —CONR16R17, —NR16CO₂R17 or —CO₂R16 radical, R7a represents a hydrogen atom or an alkyl radical having from 1 to 5 carbon atoms, R8 represents a hydrogen atom, a halogen atom, an —OH radical, or an —SH, —CONHOR16, —CONR16OH, —NR16R17, —SO₃H, —OCOR16, —NHSO₂R16, —SO₂NR16R17, —NHCOR16, —CONR16R17, —NR16CO₂R17, —NHSO₂NR16R17, —CO₂R16, pyrrolyl, imidazolyl, triazolyl or tetrazolyl radical, R9, R10, R11 and R12 are identical or different and are independently chosen from the group consisting of a hydrogen, a halogen atom and an alkyl, alkoxy, —CF₃, —OCF₃, —OH, —NO₂, —CN, —SO₂R16, —SO₂NR16R17, —NR16COR17, —NR16CO₂R17, —CONR16R17, —COR16 or —CO₂R16 radical, or alternatively, when two of the R9, R10, R11 and R12 radicals are in the ortho position on an aromatic or heteroaromatic ring selected from the group consisting of the rings corresponding to formulae (p) to (z) and (aa) to (ak) above, then they can together form, with the bond which links them together, an aryl, heteroaryl, cycloalkyl or heterocycloalkyl ring, R13 and R14 are identical or different and are independently chosen from the group consisting of a hydrogen atom, a halogen atom, and an alkyl, —CF₃, —OCF₃, —OH, —SH, —CN, —SO₂R16, —SO₂NR16R17, —NHSO₂NR16R17, —NR16R17, —NR16CONR16R17, —NR16COR17, —NR16CO₂R17, —CONR16R17, —COR16 or —CO₂R16 radical, R15 represents a hydrogen atom or an —OH, —SO₂R16, —COR16, —CO₂R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH₂COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X and X', which may be identical or different, represent an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

In one preferred embodiment according to the invention, the compounds, and also the pharmaceutically acceptable salts, solvates or hydrates thereof, correspond to the above-mentioned general formula (I) in which:

R1 represents a hydrogen atom,

R2 represents a five-membered ring chosen from the structures (1), (2) and (3) below:

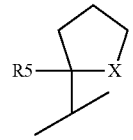

(1)

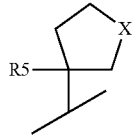

(2)

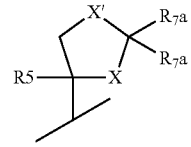

(3)

in which R5, R7a, X and X' have the meaning given hereinafter,

R3 represents an aromatic or heteroaromatic ring selected from the group consisting of the rings corresponding to formulae (a), (b) and (d) below:

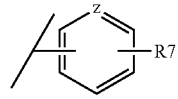

(a)

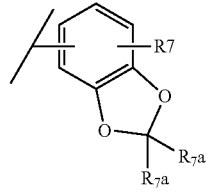

(b)

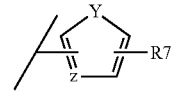

(d)

in which R7, R7a, Y and Z have the meaning given hereinafter, it being specified that the rings (a), (b) and (d) can optionally bear several R7 groups, which may be identical or different, the total number of such R7 groups being at most equal to the number of substitutable atoms of the ring;

R4 represents an aromatic or heteroaromatic ring selected from the group consisting of the rings corresponding to formulae (p), (q), (t), (z), (ad), (ag) and (ah) below:

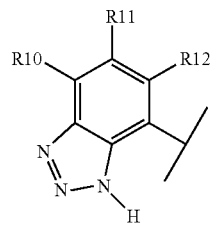

(p)

-continued

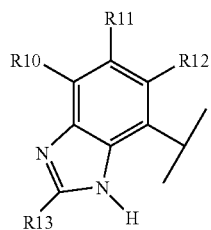
(q)

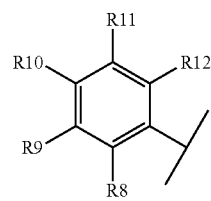
(t)

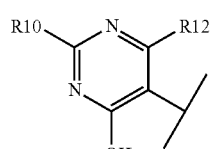
(z)

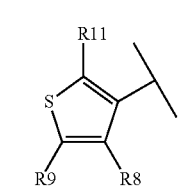
(ad)

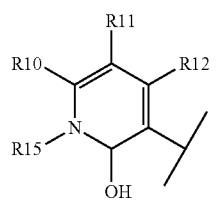
(ag)

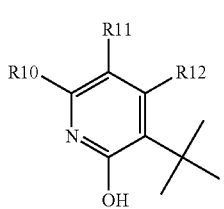
(ah)

which R8, R9, R10, R11, R12, R13 and R15 have the meaning given hereinafter,

R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a halogen, or an R16, —CF$_3$, —COR16, —OR16, —NR16R17, —NO$_2$, —CN, —SO$_2$NR16, —SO$_2$R16R17, —NR16COR17, —CONR16R17, —NR16CO$_2$R17 or —CO$_2$R16 radical, R7a represents a hydrogen or an alkyl radical having from 1 to 5 carbon atoms, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NH-COR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 or —CO$_2$R16 radical, or alternatively, when two of the R9, R10, R11 and R12 radicals are in the ortho position on an aromatic or heteroaromatic ring selected from the group consisting of the rings corresponding to formulae (p), (q), (t), (z), (ad), (ag) and (ah) above, then they can together form, with the bond which links them together, an aryl, heteroaryl, cycloalkyl or heterocycloalkyl ring, R13 is chosen from the group consisting of a hydrogen atom, a halogen atom, and an alkyl, —CF$_3$, —OCF$_3$, —OH, —SH, —CN, —SO$_2$R16, —SO$_2$NR16R17, —NHSO$_2$NR16R17, —NR16R17, —NR16CONR16R17, —NR16COR17, —NR16CO$_2$R17, —CONR16R17, —COR16 or —CO$_2$R16 radical, R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X and X', which may be identical or different, represent an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

In one more particularly preferred embodiment according to the invention, the compounds, and also the pharmaceutically acceptable salts, solvates or hydrates thereof, correspond to the abovementioned formula (I) in which:

R1 represents a hydrogen atom,

R2 represents a ring comprising five atoms, having the structure (1) below:

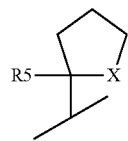
(1)

in which R5 and X have the meaning given hereinafter,

R3 represents a heteroaromatic ring corresponding to formula (d) below:

in which R7, Y and Z have the meaning given hereinafter, it being specified that the ring (d) can optionally bear several R7 groups, which may be identical or different, the total number of such R7 groups being at most equal to the number of substitutable atoms of the ring;

R4 represents an aromatic ring corresponding to formula (t) below:

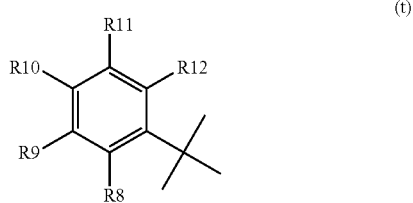

in which R8, R9, R10, R11 and R12 have the meaning given hereinafter,

R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a halogen atom, or an R16, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16 radical, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 or —CO$_2$R16 radical, or alternatively, when two of the R9, R10, R11 and R12 radicals are in the ortho position on the aromatic ring (t), they can together form, with the bond which links them together, an aryl, heteroaryl, cycloalkyl or heterocycloalkyl ring, R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

Among the compounds which are more particularly preferred, mention may be made, for example, of those chosen from the list comprising:

1/- 2-hydroxy-N,N-dimethyl-3-(2-{[5-methylfuran-2-yl)-(2-methyltetrahydrofuran-2-yl)methyl]amino}-3,4-dioxocyclobut-1-enylamino)benzamide 2/- 2-hydroxy-N,N-dimethyl-3-(2-{[(5-methylfuran-2-yl)-(tetrahydrothiophen-2-yl)methyl]amino}-3,4-dioxocyclobut-1-enylamino)benzamide 3/- methyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate 4/- isopropyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate 5/- ethyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate 6/- methyl (R)-1-[2-hydroxy-3-(2-{[(5-methylfuran-2-yl)-(tetrahydrothiophen-2-yl)methyl]amino}-3,4-dioxocyclobut-1-enylamino)benzoyl]pyrrolidine-2-carboxylate 7/- methyl (S)-1-[2-hydroxy-3-(2-{[(5-methylfuran-2-yl)-(tetrahydrothiophen-2-yl)methyl]amino}-3,4-dioxocyclobut-1-enylamino)benzoyl]pyrrolidine-2-carboxylate 8/- 2-hydroxy-N-methyl-3-(2-{[(S)-(5-methylfuran-2-yl)tetrahydrothiophen-2-ylmethyl]amino}-3,4-dioxocyclobut-1-enylamino)-N-(2,2,2-trifluoroethyl)benzamide 9/- methyl {[2-hydroxy-3-(2-{[(5-methylfuran-2-yl)-(tetrahydrothiophen-2-yl)methyl]amino}-3,4-dioxocyclobut-1-enylamino)benzoyl]methylamino}acetate 10/- 6-chloro-2-hydroxy-N,N-dimethyl-3-(2-{[(5-methylfuran-2-yl)-(tetrahydrothiophen-2-yl)methyl]amino}-3,4-dioxocyclobut-1-enylamino)benzenesulfonamide 11/- 2-hydroxy-N,N-dimethyl-3-(2-{[(R)-(5-methylfuran-2-yl)tetrahydro-furan-2-ylmethyl]amino}-3,4-dioxocyclobut-1-enylamino)benzamide 12/- 2-hydroxy-N,N-dimethyl-3-(2-{[(S)-(5-methylfuran-2-yl)tetrahydro-furan-2-ylmethyl]amino}-3,4-dioxocyclobut-1-enylamino)benzamide 15/ methyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate 18/ (−)-2-hydroxy-N-methyl-3-(2-{[(S)-(5-methylfuran-2-yl)-(tetrahydrothiophen-2-yl)methyl]amino}-3,4-dioxocyclobut-1-enylamino)-N-(2,2,2-trifluoroethyl)benzamide 19/ methyl (−)-{[2-hydroxy-3-(2-{[(S)-(5-methylfuran-2-yl)-(tetrahydrothiophen-2-yl)methyl]amino}-3,4-dioxocyclobut-1-enylamino)benzoyl]methylamino}acetate 20/ methyl (−)-1-[2-hydroxy-3-(2-{[((S)-5-methylfuran-2-yl)-(tetrahydrothiophen-2-yl)methyl]amino}-3,4-dioxocyclobut-1-enylamino)benzoyl]pyrrolidine-2-(R)-carboxylate 21/ (−)-6-chloro-2-hydroxy-N,N-dimethyl-3-(2-{[((S)-5-methylfuran-2-yl)-(tetrahydrothiophen-2-yl)methyl]amino}-3,4-dioxocyclobut-1-enylamino)benzamide 22/ (−)-3-[4-chloro-2-hydroxy-3-(4-methylpiperazine-1-sulfonyl)phenylamino]-4-{[(5-methylfuran-2-yl)-(tetrahydrothiophen-2-yl)methyl]amino}cyclobut-3-ene-1,2-dione.

A second subject according to the invention relates to a pharmaceutical composition comprising an effective amount of a compound corresponding to general formula (I), or of a pharmaceutically acceptable salt of said compound as described above, in combination with a pharmaceutically acceptable solvent or support.

A third subject according to the invention relates to the compounds corresponding to general formula (I), and also the pharmaceutically acceptable salts, solvates or hydrates thereof, or else a pharmaceutical composition comprising an effective amount of a compound corresponding to general formula (I), or of one of the pharmaceutically acceptable salts thereof or one of the pharmaceutically acceptable solvates or hydrates thereof, for use as a medicament.

A fourth subject according to the invention relates to the compounds corresponding to general formula (I), and also the pharmaceutically acceptable salts, solvates or hydrates thereof, or else a pharmaceutical composition comprising an effective amount of a compound corresponding to general formula (I), or of one of the pharmaceutically acceptable salts thereof or one of the pharmaceutically acceptable solvates or hydrates thereof, for use in the treatment of α-chemokine-mediated diseases.

A fifth subject according to the invention relates to a method for treating α-chemokine-mediated diseases using a compound corresponding to general formula (I), and also the pharmaceutically acceptable salts, solvates or hydrates thereof, or else a pharmaceutical composition comprising an effective amount of a compound corresponding to general formula (I), or of one of the pharmaceutically acceptable salts thereof or one of the pharmaceutically acceptable solvates or hydrates thereof.

By way of examples of α-chemokine-mediated diseases, mention may be made of neutrophilic dermatosis, in particular psoriasis, atopic dermatitis, acne, rosacea, asthma, chronic obstructive pulmonary diseases, respiratory diseases in adults, arthritis, inflammatory bowel diseases, Crohn's disease, transplant rejection, cystic fibrosis and skin cancers.

The term "neutrophilic dermatosis" is intended to mean, in its broadest sense, Sweet's syndrome, "ecerine hydradenitis", SAPHO syndrome, Sneddon Wilkinson syndrome, pyoderma gangrenosum, erythema elevatum duitinum, psoriasis, common psoriasis, pustular psoriasis, palmoplantar pustulosis, exanthematous pustulosis (AGEP), pustulosis with vasculitis, acropustulosis of infancy, Behcet's disease, and also certain bullous diseases such as herpes derived in the form of dermatitis, neutophilic IgA dermatosis, intraepidermal IgA pustulosis, bullous pemphigoid, IgA pemphigus, vasculitis, Leroy Reiter Fiellinger syndrome, pustulosis of the scalp, acrodermatitis continua of Hallopeau and dermatosis related to angioimmunoblastic lymphadenopathy, with cyclophosphamid-induced dysmyelopoiesis, with p-ANCA antibodies.

In one preferred embodiment according to the invention, the compound or the pharmaceutical composition mentioned above is used in the treatment of skin diseases such as neutrophilic dermatosis, in particular psoriasis, atopic dermatitis, acne and rosacea.

Another aspect of the invention relates to the use of a compound corresponding to general formula (I), and also the pharmaceutically acceptable salts, solvates or hydrates thereof, or else the use of a pharmaceutical composition comprising an effective amount of a compound corresponding to general formula (I), or of one of the pharmaceutically acceptable salts thereof or one of the pharmaceutically acceptable solvates or hydrates thereof, for preparing a medicament for the treatment of diseases of the group comprising neutrophilic dermatosis, in particular psoriasis, atopic dermatitis, acne, rosacea, asthma, chronic obstructive pulmonary diseases, respiratory diseases in adults, arthritis, inflammatory bowel diseases, Crohn's disease and skin cancers.

The compositions of general formula (I) of the present invention are prepared according to one or more of the synthesis routes as described below or as emerge from the various preparation examples given hereinafter in a nonlimiting manner.

The general synthesis route for preparing the compounds of formula (III) is illustrated in scheme 1. Sequential treatment of the alkyl squarate intermediates (A) with the amines R'2—NH$_2$ and R'3—NH$_2$ gives the compounds of formula (III). In formula (A), R'1 is a $C_1$-$C_6$ alkyl, preferably methyl or ethyl. The reaction is carried out in an inert and polar solvent (or in a mixture of solvents), such as ethanol, methanol, dimethyl sulfoxide, dimethylformamide or acetonitrile. The amines R'2—NH$_2$ and R'3—NH$_2$ can be used as free bases or in salt form. The reactions can be carried out in the presence of a suitable base, such as triethylamine, diisopropylethylamine, sodium carbonate or potassium carbonate and at 25° C. or preferably at high temperatures of 50-80° C. The reaction time is generally between 1 hour and 72 hours so as to have complete conversion.

The amines R'3—NH$_2$ of formula (IX) are prepared according to scheme 2 from commercial reagents using methods well known to those skilled in the art, described in the organic synthesis manuals, for instance "Comprehensive Organic Functional Group Transformation" Vol. 1-7 A. R. Katritzky, O. Meth-Cohn, C. W. Rees, Pergamon Press, 1998.

The primary alcohols (IV) [in which X and R have the same meaning as X and R5 respectively above for the compounds of general formula (I)] are oxidized to aldehydes of formula (V) under the conditions of Swern (Mancuso, A. J.; Huang, S.-L.; Swern, D. (1978). "Oxidation of long-chain and related alcohols to carbonyls by dimethyl sulfoxide "activated" by oxalyl chloride" *J. Org. Chem.* 43 (12), 2480-2482) or with pyridinium chlorochromate.

The aldehyde of formula (V) is successively treated with an aryl or heteroaryl Grignard reagent or with a lithiated derivative to give a secondary alcohol of formula (VI). The corresponding azides (VII) are prepared from the alcohols (VI) either by converting them into mesylates (VIII) which are subsequently treated with metal azides (for example sodium azide), or by converting them directly into azide after treatment with diphenylphosphoryl azide (DPPA). The azide (VII) is finally reduced to the corresponding amine (IX) with hydrogen in the presence of various catalysts (for example, palladium on activated carbon) or by treatment with triphenylphosphine followed by hydrolysis of the imidophosphorane intermediates (Gololobov, Y. G. (1981), "Sixty years of staudinger reaction", *Tetrahedron* 37 (3), 437).

Alternatively, the primary amines R'3—NH$_2$ of formula (IX) can be prepared according to scheme 3 from commercial acids (X) [in which X and R have the same meaning as X and R5 respectively above for the compounds of general formula (I)], by converting them to Weinreb amides (XI) (Nahm, S.; Weinreb, S. M. (1981), "N-methoxy-n-methylamides as effective acylating agents", *Tetrahedron Letters* 22, 3815), which, after reaction with aryl or heteroaryl Grignard reagents or with lithiated aryl or heteroaryl derivatives give the ketones (XII) which can be reduced to secondary alcohols (VI).

By following the steps described in scheme 2, the alcohol (VI) is optionally converted to the amine R'3—NH$_2$ of formula (IX).

The chiral primary amine R'3—NH$_2$ having the structure (XV) can also be prepared according to scheme 4 by condensation of enantiomerically pure 2-methyl-2-propanesulfinamide (tert-butanesulfinamide, Elman's sulfinamide: Liu, G. et al. *J. Am. Soc. Chem.* 1997, 119, 9913) with the aldehyde (IV) under mild conditions. This reaction provides the tert-butanesulfinyl imines (XIII). The tert-butanesulfinyl group activates the imines for the addition of the Grignard reagents and serves as an important chiral directing group for giving the products (XIV) with high diastereoselectivity. Deprotection of the tert-butanesulfinyl group under mild acidic conditions gives the chiral amine (XV).

The amide derivatives of 3-aminosalicylic acid of formula (XVIII) are prepared according to scheme 5a/ from 3-nitrosalicylic acid (XVI) using standard peptide coupling conditions (*Recent development of peptide coupling reagents in organic synthesis Tetrahedron*, Volume 60(11), 2447-2467, Han, S. -Y.; Kim, Y.-A.), followed by reduction of the nitro group to an amino group with hydrogen in the presence of an appropriate catalyst (for example, palladium on activated carbon). The derivative (XVIII) then reacts with the commercial dimethoxysquarate or diethoxysquarate to give the intermediate (XIX), which is converted to compound (XX) after reaction with the primary amine R'3—NH$_2$.

Alternatively, the coupling of the 3-aminosalicylic acid (XXI) with the commercial dimethoxysquarate or diethoxysquarate gives, according to scheme 5b/, the intermediate acid derivative (XXII) which, after reaction with the primary amine R'3—NH$_2$, can give the compound (XVIII). The latter can, finally, be used in a peptide coupling reaction with an amine of formula RaRbNH to give the compound of formula (XX).

By way of illustration, the following compounds corresponding to general formula (I) of the present invention were prepared according to one of the schemes presented above.

EXAMPLE 1

Preparation of 2-hydroxy-N,N-dimethyl-3-(2-{[(5-methylfuran-2-yl)-(2-methyltetrahydrofuran-2-yl) methyl]amino}-3,4-dioxocyclobut-1-enylamino) benzamide

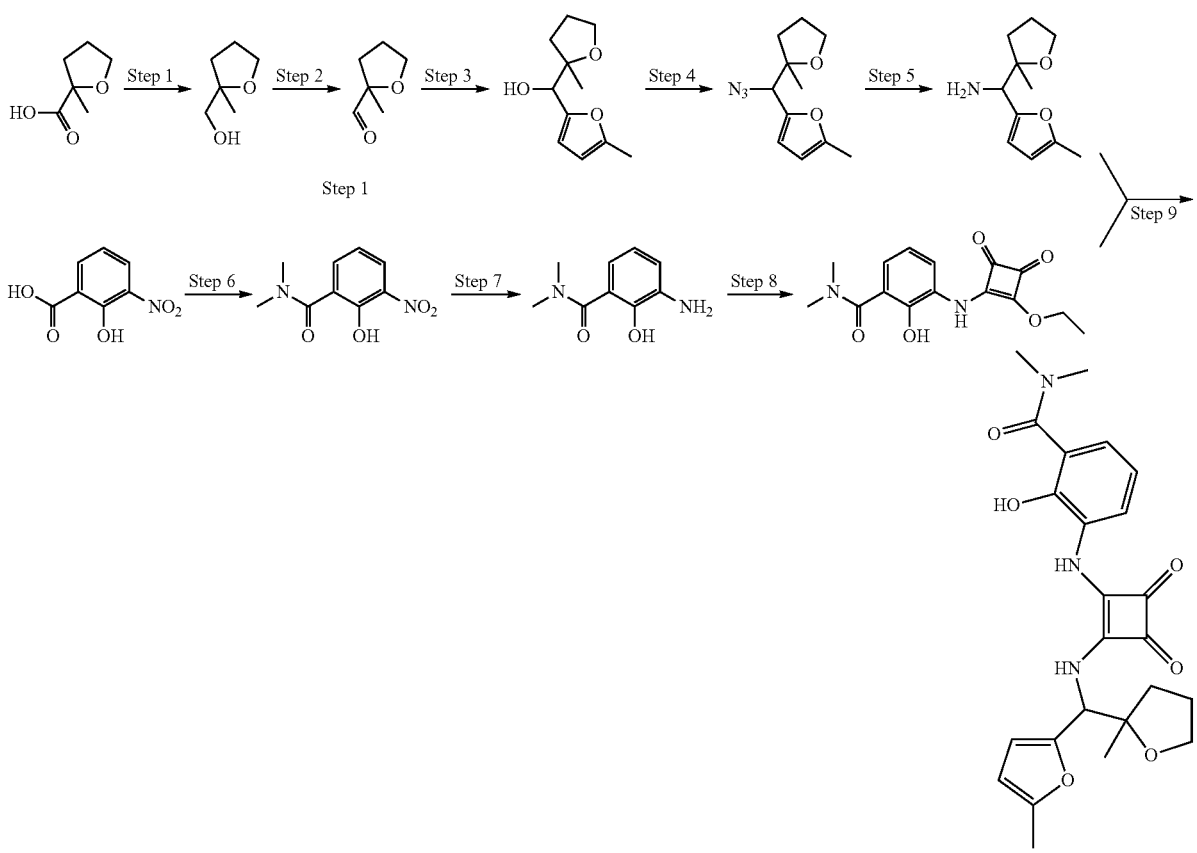

Step 1:
(2-Methyltetrahydrofuran-2-yl)methanol 19.94 g (0.145 mol, 1 eq) of 2-methyltetrahydrofuran-2-carboxylic acid (commercial) at 95% in solution in 100 ml of diethyl ether were added dropwise to a suspension, cooled to 10° C., of 16.6 g (0.438 mol, 3 eq) of lithium aluminum hydride in 100 ml of diethyl ether. The reaction medium was stirred at ambient temperature for 24 hours. The reaction medium was cooled and water was added dropwise, followed by a saturated ammonium chloride solution. The medium was extracted with diethyl ether. The organic phases were combined, washed with water, dried over magnesium sulfate, filtered and evaporated. 14.45 g of (2-methyltetrahydrofuran-2-yl)methanol were obtained. Yield=86%. TLC/SiO$_2$: CH$_2$Cl$_2$/MeOH (95/5), developing with KMnO$_4$.

Step 2:
2-Methyltetrahydrofuran-2-carbaldhyde

A solution of 14.44 g (0.124 mol, 1 eq) of (2-methyltetrahydrofuran-2-yl)methanol in 140 ml of dichloromethane was added dropwise to a mixture of 43.0 g (0.20 mol, 1.6 eq) of pyridinium chlorochromate in 400 ml of dichloromethane. 15 g of celite were added and the reaction medium was stirred at ambient temperature for 7 hours. The reaction medium was filtered on 280 g of silica and eluted with dichloromethane (4.5 1). 6.0 g of 2-methyltetrahydrofuran-2-carbaldehyde were obtained in the form of a yellow liquid (1st fraction at 77%). 8.4 g of 2-methyltetrahydrofuran-2-carbaldehyde were obtained in the form of an orange liquid (2nd fraction at 54%). Yield=65%. TLC/$SiO_2$: heptane/EtOAc (40/60), developing with $KMnO_4$.

Step 3:
(5-Methylfuran-2-yl)(2-methyltetrahydrofuran-2-yl)methanol 24 ml (60 mmol, 1.5 eq) of a 2.5 M solution of n-butyllithium in hexane were added dropwise to a solution of 5.0 g (60 mmol, 1.5 eq) of 2-methylfuran in 100 ml of tetrahydrofuran cooled to −70° C. The reaction medium was stirred and allowed to return to ambient temperature for 2 hours. The reaction medium was cooled to −70° C. and then 6.0 g (40 mmol, 1 eq) of 2-methyltetrahydrofuran-2-carbaldehyde at 77% were added. The reaction medium was stirred at ambient temperature for 3 hours. The reaction medium was treated with a saturated ammonium chloride solution and extracted with ethyl acetate. The organic phases were combined, washed with a saturated sodium chloride solution, filtered over magnesium sulfate and evaporated. 5.21 g of (5-methylfuran-2-yl)-(2-methyltetrahydrofuran-2-yl)methanol were obtained. Yield=66%. TLC/$SiO_2$: heptane/EtOAc (60/40), developing with $KMnO_4$.

Step 4:
2-[Azido-(2-methyltetrahydrofuran-2-yl)methyl]-5-methylfuran 8.77 g (31.8 mmol, 1.2 eq) of diphenylphosphoryl azide were added dropwise to a solution of 5.21 g (26.5 mmol, 1 eq) of (5-methylfuran-2-yl)-(2-methyltetrahydrofuran-2-yl)methanol in 90 ml of toluene. The reaction medium was cooled to 0° C. and then 4.75 ml (31.8 mmol, 1.2 eq) of 1,8-diazabicyclo[5.4.0]undec-7-ene were added dropwise. The reaction medium was stirred at ambient temperature for 41 hours. The (heterogeneous) reaction medium was treated with water and with ethyl acetate and then separated by settling out. The organic phase was washed with 1 N hydrochloric acid, dried over magnesium sulfate, filtered and evaporated. The residue was chromatographed on HP silica gel (column puriFlash IR50SI-200G, Spot II) eluted with heptane/ethyl acetate (95/5). 2.15 g of 2-[azido-(2-methyltetrahydrofuran-2-yl)methyl]-5-methylfuran were obtained. Yield=37%. TLC/$SiO_2$: heptane/EtOAc (80/20), developing with $KMnO_4$.

Step 5:
(5-Methylfuran-2-yl)(2-methyltetrahydrofuran-2-yl)methanamine

A solution of 2.51 g (9.7 mmol, 1 eq) of 2-[azido-(2-methyltetrahydrofuran-2-yl)methyl]-5-methylfuran in 45 ml of ethanol was stirred at hydrogen atmospheric pressure in the presence of 323 mg (15% by weight) of palladium on carbon (Pd/C) at 10% for 16 hours. The reaction medium was filtered and the filtrate was evaporated. 1.82 g of (5-methylfuran-2-yl)(2-methyltetrahydrofuran-2-yl)methanamine were obtained. Yield=96%. TLC/$SiO_2$: heptane/EtOAc (60/40), developing with $KMnO_4$.

Step 6:
2-Hydroxy-N,N-dimethyl-3-nitrobenzamide 42.9 ml (0.50 mol, 3 eq) of oxalyl chloride were added dropwise to a suspension of 30 g (0.16 mol, 1 eq) of 3-nitro salicylic acid in 1200 ml of dichloromethane. 30 drops of N,N-dimethylformamide were added (large amount of gas given off, adaptation of a system for trapping toxic carbon monoxide vapors). The reaction medium was stirred at ambient temperature for 24 hours. The reaction medium was cooled to 0-5° C. and then 246 ml (0.49 mol, 3 eq) of a 2 N solution of dimethylamine in tetrahydrofuran were added. The reaction medium was stirred at ambient temperature for 2 days. The reaction medium was concentrated to dryness and the residue was dissolved in 300 ml of 1 N sodium hydroxide. The aqueous solution (red) was extracted 3 times with 300 ml of dichloromethane. The aqueous phase was cooled in a water-ice bath, and the pH was adjusted to 2 with approximately 50 ml of 6 N hydrochloric acid. The mixture (which had become yellow) was extracted 3 times with 300 ml of dichloromethane. The organic phases were combined, washed twice with 250 ml of water and then once with 250 ml of a saturated sodium chloride solution, dried over anhydrous magnesium sulfate and evaporated. 33.5 g of 2-hydroxy-N,N-dimethyl-3-nitrobenzamide were obtained in the form of a cottony yellow solid. Yield=97%.

Step 7:
3-Amino-2-hydroxy-N,N-dimethylbenzamide

A solution of 33.5 g of 2-hydroxy-N,N-dimethyl-3-nitrobenzamide in 600 ml of ethanol was added to a suspension of 3.35 g of Pd/C 10% in 70 ml of ethanol. The reaction medium was stirred under 2 bar of hydrogen overnight. TLC and HPLC control (t=0.66 M+181). The reaction medium was filtered through celite and the filtrate was evaporated. 29 g of 3-amino-2-hydroxy-N,N-dimethylbenzamide were obtained in the form of an oily brown solid. Yield=100%.

Step 8:
3-(2-Ethoxy-3,4-dioxocyclobut-1-enylamino)-2-hydroxy-N,N-dimethylbenzamide Under nitrogen and at ambient temperature, 39.7 g of diethoxysquarate were added (over the course of 15 minutes) to a solution of 28 g of 3-amino-2-hydroxy-N,N-dimethylbenzamide in 840 ml of ethanol cooled to 0° C. The reaction medium was stirred for 2 hours at 0° C. and 48 hours at ambient temperature. 700 ml of ethanol were added (which increases the precipitation of the expected product). The solid was filtered off, washed with ambient ethanol and dried. 36.9 g of 3-(2-ethoxy-3,4-dioxocyclobut-1-enylamino)-2-hydroxy-N,N-dimethylbenzamide were obtained in the form of a light khaki green solid. Yield=78%.

Step 9:
2-Hydroxy-N,N-dimethyl-3-(2-{[(5-methylfuran-2-yl)-(2-methyltetrahydrofuran-2-yl)methyl]amino}-3,4-dioxocyclobut-1-enylamino)benzamide (diastereoisomers 1 and 2)

1.82 g (9.3 mmol, 1.5 eq) of (5-methylfuran-2-yl)(2-methyltetrahydrofuran-2-yl)methanamine were added to 1.89 g (6.2 mmol, 1 eq) of 3-(2-ethoxy-3,4-dioxocyclobut-1-enylamino)-2-hydroxy-N,N-dimethylbenzamide dissolved under hot conditions in 100 ml of methanol. The reaction medium was heated at 60° C. for three and a half hours. The methanol was evaporated off and the residue was chromatographed on silica gel (column puriFlash IR50SI-200G, Spot II) eluted with dichloromethane/methanol (gradient).

Diastereoisomer 1, 1.00 g of 2-hydroxy-N,N-dimethyl-3-(2-{[(5-methylfuran-2-yl)-(2-methyltetrahydrofuran-2-yl)methyl]amino}-3,4-dioxocyclobut-1-enylamino)benzamide was obtained in the form of a beige solid (Mp=127-129° C.). LC/MS: 98.41% [453].

$^1$H NMR (DMSO, 400 MHz); 1.22 (s, 3H); 1.57-1.62 (m, 1H); 1.67-1.74 (m, 1H); 1.82-1.89 (m, 1H); 1.95-1.99 (m, 1H); 2.28 (s, 3H); 2.94 (s, 6H); 3.6 (q, J=6.7 Hz, 1H); 3.8 (q, J=7.5 Hz, 1H); 5.3 (d, J=10 Hz, 1H); 6.06 (d, J=3.0 Hz, 1H); 6.25 (dd, J=3.0 Hz, 1H); 6.87 (m, 2H); 7.76 (dd, J=6.7 Hz, 1H); 8.93 (d, J=10.0 Hz, 1H); 9.56 (s, 1H); 9.92 (s, 1H).

Diastereoisomer 2, 1.03 g of 2-hydroxy-N,N-dimethyl-3-(2-{[(5-methylfuran-2-yl)-(2-methyltetrahydrofuran-2-yl)methyl]amino}-3,4-dioxo-cyclobut-1-enylamino)benzamide were obtained. (Mp=127-129° C.), LC/MS: 97.76% [453].

¹H NMR (DMSO-d6, 400 MHz): 1.16 (s, 3H); 1.65-1.70 (m, 1H); 1.84-1.98 (m, 3H); 2.28 (s, 3H); 2.94 (s, 6H); 3.76-3.80 (m, 2H); 5.3 (d, J=9.9 Hz, 1H); 6.06 (dd, J=2.9 Hz, 1H); 6.28 (d, J=3.0 Hz, 1H); 6.85-6.91 (m, 2H); 7.75 (dd, J=6.9 Hz, 1H); 8.85 (d, J=10.0 Hz, 1H); 9.54 (s, 1H); 9.95 (s, 1H).

2-Hydroxy-N,N-dimethyl-3-(2-{[(5-methylfuran-2-yl)-(2-methyltetrahydrofuran-2-yl)methyl]amino}-3,4-dioxo-cyclobut-1-enylamino)benzamide (enantiomers 1 and 2 of diastereoisomer 2)

The separation of diastereoisomer 2 into enantiomers 1 and 2 was carried out on the CHIRALCEL® OD-H 5 μm-250×4.6 mm chiral column; mobile phase: carbon dioxide/methanol (80/20), flow rate of 120 ml/min.

Enantiomer 1 of diastereoisomer 2: retention time at 3.91 min.

Enantiomer 2 of diastereoisomer 2: retention time at 5.08 min.

EXAMPLE 2:

Preparation of 2-hydroxy-N,N-dimethyl-3-(2-{[(5-methylfuran-2-yl)-(tetrahydrothiophen-2-yl)methyl]amino}-3,4-dioxocyclobut-1-enylamino)benzamide Step 1:
Methoxymethyltetrahydrothiophene-2-carboxylamide 32.0 ml (0.44 mol; 1.27 eq) of thionyl chloride were added dropwise, at ambient temperature, over the course of 15 minutes, to a solution of 46.0 g (0.35 mol; 1.0 eq) of tetrahydrothiophene-2-carboxylic acid (commercial) in 200 ml of dichloromethane. The reaction medium was stirred at ambient temperature for 3 hours until no more gas was given off. The dichloromethane and the excess thionyl chloride were evaporated off under vacuum and the residue was co-evaporated three times with 100 ml of toluene. The acid chloride obtained was solubilized in 200 ml of dichloromethane, and 37.34 g (0.38 mol; 1.1 eq) of N,O-dimethylhydroxylamine hydrochloride were added. The reaction medium was cooled to −10° C. and a mixture of 116 ml (0.84 mol; 2.4 eq) of triethylamine in 100 ml of dichloromethane was added dropwise over the course of one hour (while maintaining the temperature below 5° C.). After the addition, the reaction medium was stirred at ambient temperature for one hour and was then washed with 250 ml of a 1 M aqueous hydrochloric acid solution. The aqueous phase was extracted with dichloromethane. The organic phases were combined, washed with 200 ml of a 1 M aqueous sodium hydrogen phosphate solution, dried over anhydrous magnesium sulfate, filtered and evaporated. 51.0 g of methoxymethyltetrahydrothiophene-2-carboxylamide were obtained in the form of an orange oil. Yield=84%.

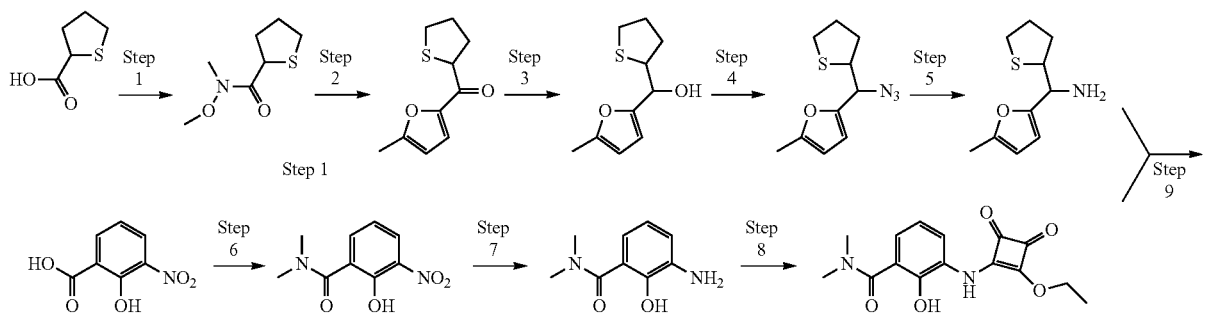

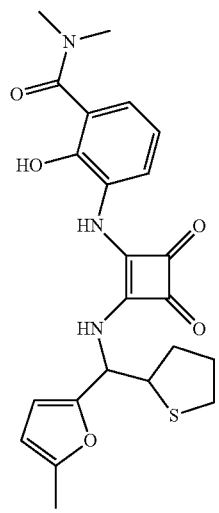

Step 2:

(5-Methylfuran-2-yl)-(tetrahydrothiophen-2-yl)methanone 176 ml (440.8 mmol; 1.50 eq) of n-butyllithium at 2.5 M in hexane were added dropwise to a solution of 39.8 ml (440.8 mmol; 1.50 eq) of 2-methylfuran in 1 l of tetrahydrofuran cooled to −78° C. The mixture was allowed to return to ambient temperature for 2 hours and was then cooled to −78° C. A solution of 51.00 g (291 mmol; 1.00 eq) of methoxymethyltetrahydrothiophene-2-carboxylamide in 400 ml of tetrahydrofuran was added and the reaction mixture was left at 0° C. for 2 hours. The reaction medium was diluted with 500 ml of ethyl acetate and then washed with 1 l of a 1 N aqueous hydrochloric acid solution. The aqueous phase was separated and extracted with 500 ml of ethyl acetate. The organic phases were combined, washed with a saturated sodium chloride solution, dried over anhydrous magnesium sulfate, filtered and evaporated. The brown oil obtained was filtered on silica (eluent: 90/10 heptane/EtOAc). 49.67 g of (5-methylfuran-2-yl)-(tetrahydrothiophen-2-yl)methanone were obtained. Yield=87%.

Step 3:

(5-Methylfuran-2-yl)-(tetrahydrothiophen-2-yl)methanol 6.69 g (0.18 mol; 1.20 eq) of sodium borohydride were added in small portions to a solution of 30.24 g (0.15 mol; 1.0 eq) of (5-methylfuran-2-yl)-(tetrahydrothiophen-2-yl)methanone in 300 ml of tetrahydrofuran and 50 ml of methanol cooled to 0° C. The reaction medium was stirred at ambient temperature for 3 hours. The reaction medium was poured into 400 ml of ethyl acetate and then 200 ml of water were added. The aqueous phase was extracted with ethyl acetate and then the organic phases were combined, washed with a saturated sodium chloride solution, dried over anhydrous magnesium sulfate, filtered and evaporated. 30.22 g of (5-methylfuran-2-yl)-(tetrahydrothiophen-2-yl)methanol were obtained. Quantitative yield.

Step 4:

2-[Azido-(tetrahydrothiophen-2-yl)methyl]-5-methylfuran 39.3 ml (0.18 mol; 1.2 eq) of diphenylphosphoryl azide and then 27.3 ml (0.18 mol; 1.2 eq) of 1,8-diazabicyclo[5.4.0] undec-7-ene were added dropwise to a solution of 30.21 g (0.15 mol; 1.0 eq) of (5-methylfuran-2-yl)-(tetrahydrothiophen-2-yl)methanol in 350 ml of toluene cooled to 0° C. The mixture was allowed to return to ambient temperature gently and was then stirred for 2 days. The reaction medium was treated with water and extracted with ethyl acetate. The organic phases were combined, washed with a 1 M sodium hydrogen phosphate solution, dried over magnesium sulfate, filtered and evaporated. The residue was chromatographed on silica gel (column puriFlash IR-50SI/800G, puriFlash) eluted with heptane/ethyl acetate (95/5). 26.95 g of 2-[azido-(tetrahydrothiophen-2-yl)methyl]-5-methylfuran were obtained (mixture of the 2 diastereoisomers). Yield=79%.

Step 5:

(R,S)-(5-Methylfuran-2-yl)((R,S)-tetrahydrothiophen-2-yl)methanamine (diastereoisomer 1) and (R,S)-(5-methylfuran-2-yl)((S,R)-tetrahydrothiophen-2-yl)methanamine (diastereoisomer 2)

A solution of 26.95 g (0.12 mol, 1.0 eq) of 2-[azido-(tetrahydrothiophen-2-yl)methyl]-5-methylfuran in 540 ml of ethanol and in the presence of 6.74 g (25% by weight) of Pd/C 10% was stirred at ambient temperature at hydrogen atmospheric pressure for 2 days. The reaction medium was filtered and the filtrate was evaporated. The residue was chromatographed on silica gel (column puriFlash IR-50SI-STD/800G, puriFlash) eluted with dichloromethane/ethyl acetate (gradient).

Diastereoisomer 1: 5.52 g of (R,S)-(5-methylfuran-2-yl) ((R,S)-tetrahydrothiophen-2-yl)methanamine [as a mixture of (R)-(-5-methylfuran-2-yl)((R)-tetrahydrothiophen-2-yl) methanamine and (S)-(-5-methylfuran-2-yl)((S)-tetrahydrothiophen-2-yl)methanamine] were obtained. Yield=22%.

Diastereoisomer 2: 13.30 g of (R,S)-(5-methylfuran-2-yl) ((S,R)-tetrahydrothiophen-2-yl)methanamine [as a mixture of (R)-(-5-methylfuran-2-yl)((S)-tetrahydrothiophen-2-yl) methanamine and (S)-(-5-methylfuran-2-yl)((R)-tetrahydrothiophen-2-yl)methanamine] were obtained. Yield=54%.

Steps 6 to 8:

In a manner analogous to EXAMPLE 1 (steps 6 to 8), 3-(2-ethoxy-3,4-dioxocyclobut-1-enylamino)-2-hydroxy-N, N-dimethylbenzamide was prepared.

Step 9:

2-Hydroxy-N,N-dimethyl-3-(2-{[(5-methylfuran-2-yl)-(tetrahydrothiophen-2-yl)methyl]amino}-3,4-dioxo-cyclobut-1-enylamino)benzamide (diastereoisomer 1)

A mixture of 694 mg (2.28 mmol; 1.0 eq) of 3-(2-ethoxy-3,4-dioxocyclobut-1-enylamino)-2-hydroxy-N,N-dimethylbenzamide and 540 mg (2.74 mmol; 1.2 eq) of (R,S)-(-5-methylfuran-2-yl)-(R,S)-(tetrahydrothiophen-2-yl) methanamine (diastereoisomer 1) in solution in 20 ml of methanol was stirred at ambient temperature for 4 days. The insoluble material was filtered off and dried under vacuum at 50° C., 560 mg of 2-hydroxy-N,N-dimethyl-3-(2-{[(5-methylfuran-2-yl)-(tetrahydrothiophen-2-yl)methyl]amino}-3,4-dioxocyclobut-1-enylamino)benzamide (diastereoisomer 1) were obtained. Yield=54%.

$^1$H NMR (DMSO-d6, 400 MHz): 1.63-1.68 (m, 1H), 1.88-1.92 (m, 1H), 1.98-2.04 (m, 2H), 2.26 (s, 3H), 2.81 (t, J=5.9 Hz, 2H), 2.94 (s, 6H), 3.97 (q, J=6.6 Hz, 1H), 5.41 (q, J=6.8-2.7 Hz, 1H), 6.06 (dd, J=0.9-3.0 Hz, 1H), 6.26 (d, J=3.1 Hz, 1H), 6.86-6.91 (m, 2H), 7.75 (dd, J=2.6-7.0 Hz, 1H), 8.82 (d, J=9.6 Hz, 1H), 9.51 (s, 1H), 9.94 (s, 1H).

2-Hydroxy-N,N-dimethyl-3-(2-{[(5-methylfuran-2-yl)-(tetrahydrothiophen-2-yl)methyl]amino}-3,4-dioxo-cyclobut-1-enylamino)benzamide (diastereoisomer 2)

A mixture of 1.29 g (4.22 mmol; 1.0 eq) of 3-(2-ethoxy-3,4-dioxocyclobut-1-enylamino)-2-hydroxy-N,N-dimethylbenzamide and 1.0 g (5.07 mmol; 1.2 eq) of (R,S)-(-5-methylfuran-2-yl)-(S,R)-(tetrahydrothiophen-2-yl)methanamine (diastereoisomer 2) in solution in 40 ml of methanol was stirred at ambient temperature for two and a half days. The insoluble material was filtered off and dried under vacuum at 45° C. 1.48 g of 2-hydroxy-N,N-dimethyl-3-(2-{[(5-methylfuran-2-yl)-(tetrahydrothiophen-2-yl)methyl]amino}-3,4-dioxocyclobut-1-enylamino)benzamide (diastereoisomer 2) were obtained. Yield=77%.

$^1$H NMR (DMSO-d6, 400 MHz): 1.82-1.86 (m, 2H), 1.90-1.93 (m, 2H), 2.26 (s, 3H), 2.75-2.84 (m, 2H), 2.93 (s, 6H), 3.86 (m, 1H), 5.2 (t, J=9.7 Hz, 1H), 6.06 (dd, J=1.0-3.0 Hz, 1H), 6.30 (d, J=3.1 Hz, 1H), 6.84-6.90 (m, 2H), 7.79 (dd, J=2.3-7.2 Hz, 1H), 8.77 (d, J=9.6 Hz, 1H), 9.34 (s, 1H), 9.94 (s, 1H).

2-Hydroxy-N,N-dimethyl-3-(2-{[(5-methylfuran-2-yl)-(tetrahydrothiophen-2-yl)methyl]amino}-3,4-dioxo-cyclobut-1-enylamino)benzamide (enantiomers 1 and 2)

The separation of diastereoisomer 1 into enantiomers was carried out on the CHIRALPACK$^R$ IC μm chiral column; mobile phase: carbon dioxide/ethanol (100/0.5), flow rate of 120 ml/min.

Enantiomer 1 of diastereoisomer 1: retention time at 6.1 min.

Enantiomer 2 of diastereoisomer 1: retention time at 8.0 min.

2-Hydroxy-N,N-dimethyl-3-(2-{[(5-methylfuran-2-yl)-(tetrahydrothiophen-2-yl)methyl]amino}-3,4-dioxo-cyclobut-1-enylamino)benzamide (enantiomers 1 and 2)

The separation of diastereoisomer 2 into enantiomers was carried out on the CHIRALPACK$^R$ ADH 5 μm chiral column; mobile phase: heptane/ethanol (60/40), flow rate of 42.5 ml/min.

Enantiomer 1 of diastereoisomer 2: retention time at 3.6 min.

Enantiomer 2 of diastereoisomer 2: retention time at 4.7 min.

EXAMPLE 3

Preparation of Methyl (S)-1-[2-fluoro-3-(2-{[(5-methylfuran-2-yl)-(tetrahydrothiophen-2-yl)methyl] amino}-3,4-dioxocyclobut-1-enylamino)benzoyl] pyrrolidine-2-carboxylate

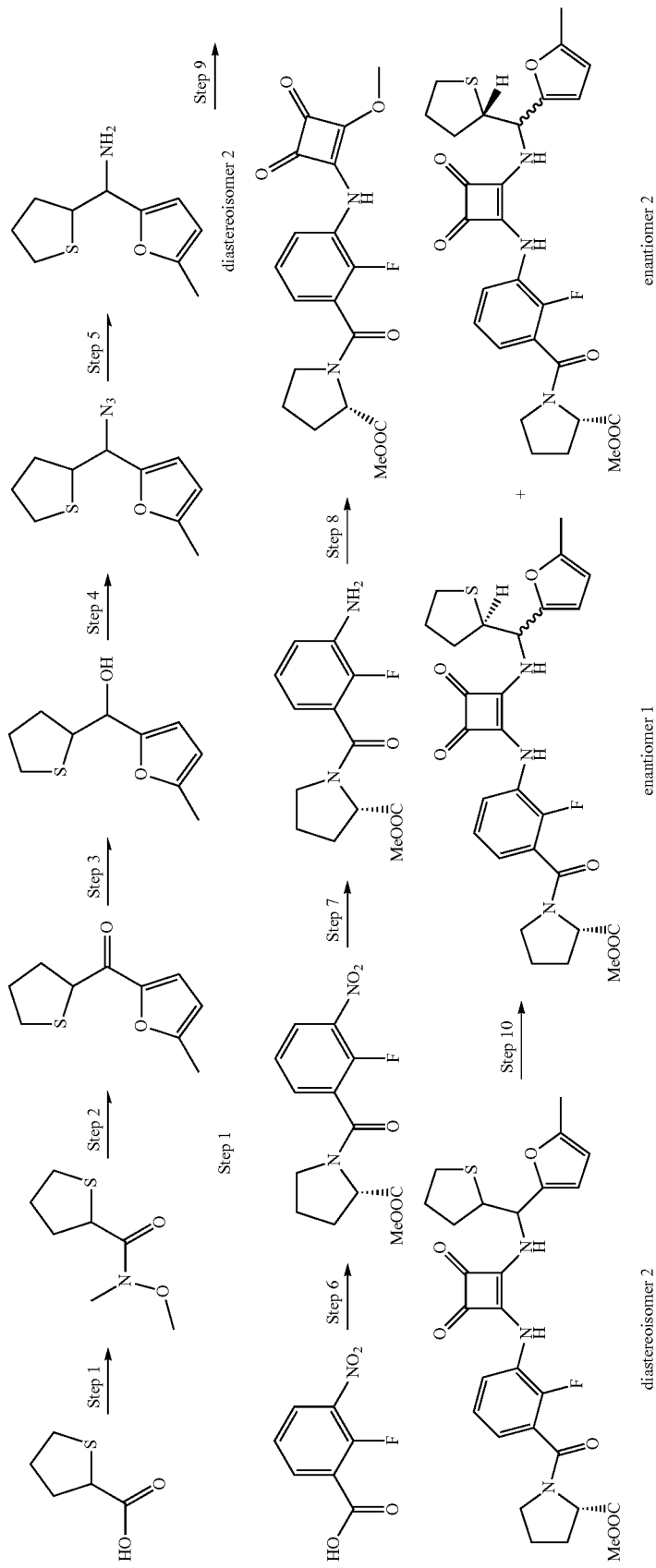

Steps 1 to 5:

In a manner analogous to EXAMPLE 2 (steps 1 to 5), (R,S)-(5-methylfuran-2-yl)-(S,R)-(tetrahydrothiophen-2-yl) methanamine (diastereoisomer 2) was prepared.

Step 6:

Methyl (S)-1-(2-fluoro-3-nitrobenzoyl)pyrrolidine-2-carboxylate

A mixture of 18.51 g (0.10 mol; 1.0 eq) of 2-fluoro-3-nitrobenzoic acid and 100 ml of thionyl chloride was refluxed for 3 hours. The excess thionyl chloride was then concentrated and the residue was co-evaporated twice with toluene. The resulting acid chloride was taken up in 250 ml of dichloromethane. To this mixture, cooled to 0° C., were added 16.56 g (0.10 mol; 1.0 eq) of L-proline methyl ester hydrochloride and then 30.50 ml (0.22 mol; 2.2 eq) of triethylamine. After 30 minutes at 0° C. and one hour at ambient temperature, the reaction medium was diluted and washed with 250 ml of a 1 M aqueous hydrochloric acid solution and then with 250 ml of a saturated aqueous sodium hydrogen carbonate solution. The organic phase was dried over anhydrous magnesium sulfate, filtered and evaporated. 25.64 g of methyl (S)-1-(2-fluoro-3-nitrobenzoyl)pyrrolidine-2-carboxylate were obtained. Yield=87%.

Step 7:

Methyl (S)-1-(3-amino-2-fluorobenzoyl)pyrrolidine-2-carboxylate

A solution of 25.0 g (0.08 mol, 1.0 eq) of methyl (S)-1-(2-fluoro-3-nitrobenzoyl)pyrrolidine-2-carboxylate in 250 ml of methanol in the presence of 7.0 g (28% by weight) of palladium on carbon at 10% was stirred under a hydrogen atmosphere at ambient temperature for 4 days. The reaction medium was filtered through celite and washed with 100 ml of methanol. The filtrate was evaporated. 22.80 g of methyl (S)-1-(3-amino-2-fluorobenzoyl)pyrrolidine-2-carboxylate were obtained in the form of a light oil. Quantitative yield.

Step 8:

Methyl (S)-1-[2-fluoro-3-(2-methoxy-3,4-dioxocyclobut-1-enylamino)benzoyl]pyrrolidine-2-carboxylate 21.35 g (0.15 mol; 2.0 eq) of 3,4-dimethoxy-3-cyclobutene-1,2-dione were added to a solution of 20.0 g (0.08 mol; 1.0 eq) of methyl (S)-1-(3-amino-2-fluorobenzoyl)pyrrolidine-2-carboxylate in 150 ml of methanol. The reaction medium was heated at 50° C. for 3 hours and concentrated. The residue was eluted on a silica cake (15 cm in diameter and 10 cm high) with 2 l of heptane/ethyl acetate (2/1), 2 l of heptane/ethyl acetate (1/2) and 2 l of ethyl acetate/methanol (95/5). 19 g of a product were obtained. This product was purified by chromatography on silica gel eluted with ethyl acetate. 15 g of methyl (S)-1-[2-fluoro-3-(2-methoxy-3,4-dioxocyclobut-1-enylamino)benzoyl]pyrrolidine-2-carboxylate were obtained. Yield=53%.

Step 9:

Methyl (S)-1[2-fluoro-3-(2-{[(R,S)-(5-methylfuran-2-yl)((S,R)-tetrahydrothiophen-2-yl)methyl]amino}-3,4-dioxocyclobut-1-enylamino)benzoyl]pyrrolidine-2-carboxylate A mixture of 1.02 g (2.70 mmol; 1.0 eq) of methyl (S)-1-[2-fluoro-3-(2-methoxy-3,4-dioxocyclobut-1-enylamino) benzoyl]pyrrolidine-2-carboxylate and 640 mg (3.24 mmol; 1.2 eq) of (R,S)-(5-methylfuran2-yl)((S,R)-tetrahydrothiophen-2-yl)methanamine (diastereoisomer 2) in solution in 25 ml of methanol was stirred at ambient temperature for three and a half days. The reaction medium was evaporated and the residue was chromatographed on silica gel (column puriFlash IR-50SI/120G, Spot II) eluted with dichloromethane/ethyl acetate (gradient). 1.01 g of methyl (S)-1[2-fluoro-3-(2-{[(R,S)-(5-methylfuran-2-yl)((S,R)-tetrahydrothiophen-2-yl)methyl]amino}-3,4-dioxocylobut-1-enylamino)benzoyl]pyrrolidine-2-carboxylate (pair of enantiomers 1 and 2) were obtained. Yield=69%.

$^1$H NMR (DMSO-d6, 400 MHz): 1.81-2.07 (m, 7H), 2.26 (s, 3H), 2.29 (m, 1H), 2.75-2.84 (m, 2H), 3.35-3.38 (m, 2H), 3.68 (s, 3H), 3.86-3.90 (m, 1H), 4.49-4.53 (m, 1H), 5.17 (t, J=9.5 Hz, 1H), 6.07 (d, J=2.9 Hz, 1H), 6.33 (d, J=3.1 Hz, 1H), 7.02 (t, J=6.6 Hz, 1H), 7.26 (t, J=7.9 Hz, 1H), 8.05 (t, J=7.9 Hz, 1H), 7.56 (d, J=9.6 Hz, 1H), 9.64 (s, 1H).

Step 10:

Methyl (S)-1-[2-fluoro-3-(2-{[(5-methylfuran-2-yl)-(tetrahydrothiophen-2-yl)methyl]amino}-3,4-dioxo-cyclobut-1-enylamino)benzoyl]pyrrolidine-2-carboxylate (enantiomer 1 and enantiorner 2)

The enantiomers 1 and 2 were separated on the CHIRALPACK ADH 5 µm column with the eluent 85/15 carbon dioxide/(ethanol+1% diethylamine), flow rate of 120 ml/min.

Methyl (S)-1-[2-fluoro-3-(2-{[(S)-(5-methylfuran-2-yl)((R)-tetrahydrothiophen-2-yl)methyl]amino}-3,4-dioxocyclobut-1-enylamino)benzoyl]pyrrolidine-2-carboxylate (enantiomer 1): retention time at 20.9 min.

Methyl (S)-1-[2-fluoro-3-(2-{[(R)-(5-methylfuran-2-yl)((S)-tetrahydrothiophen-2-yl)methyl]amino}-3,4-dioxocyclobut-1-enylamino)benzoyl]pyrrolidine-2-carboxylate (enantiomer 2): retention time at 33.7 min.

EXAMPLE 4

Preparation of Isopropyl (S)-1-[2-fluoro-3-(2-{[(5-methylfuran-2-yl)-(tetrahydrothiophen-2-yl)methyl] amino}-3,4-dioxocyclobut-1-enylamino)benzoyl] pyrrolidine-2-carboxylate

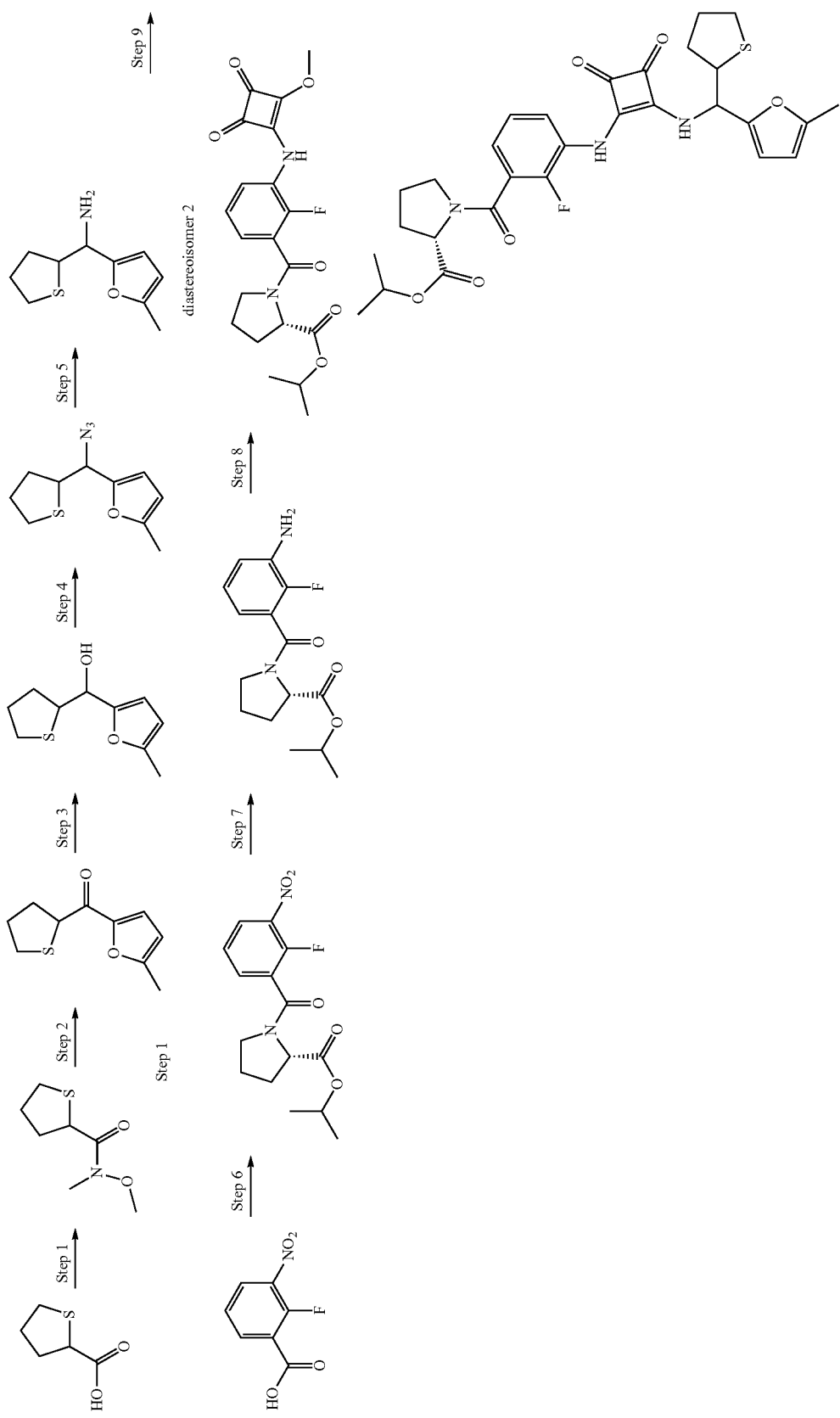

Steps 1 to 5:

In a manner analogous to EXAMPLE 2 (steps 1 to 5), C(R,S)-(5-methylfuran-2-yl)-(S,R)-(tetrahyrothiophen-2-yl)methanamine (diastereoisomer 2) was prepared.

Step 6:

Isopropyl (S)-1-(2-fluoro-3-nitrobenzoyl)pyrrolidine-2-carboxylate

A mixture of 1.50 g (8.10 mmol; 1.0 eq) of 2-fluoro-3-nitrobenzoic acid and 16 ml of thionyl chloride was refluxed for 3 hours. The excess thionyl chloride was then concentrated and the residue was co-evaporated twice with toluene. The resulting acid chloride was taken up in 25 ml of dichloromethane. 1.27 g (8.10 mmol; 1.0 eq) of isopropyl (S)-pyrrolidine-2-carboxylate were added to this mixture cooled to 0° C. The reaction medium was stirred at 0° C. for 30 minutes and then at ambient temperature for 2 hours. The reaction medium was diluted and washed with a 1 M hydrochloric acid solution (100 ml) and then with a saturated sodium hydrogen carbonate solution (100 ml). The organic phase was dried over $MgSO_4$, filtered and evaporated. 2.12 g of isopropyl (S)-1-(2-fluoro-3-nitrobenzoyl)pyrrolidine-2-carboxylate were obtained. Yield=81%.

Step 7:

Isopropyl (S)-1-(3-amino-2-fluorobenzoyl)pyrrolidine-2-carboxylate

A solution of 2.12 g (6.55 mmol, 1.0 eq) of isopropyl (S)-1-(2-fluoro-3-nitrobenzoyl)pyrrolidine-2-carboxylate in 40 ml of methanol in the presence of 0.32 g (15% by weight) of palladium on carbon at 10% was stirred under a hydrogen atmosphere at ambient temperature for 16 hours. The reaction medium was filtered through celite and concentrated to dryness. 1.87 g of isopropyl (S)-1-(3-amino-2-fluorobenzoyl)pyrrolidine-2-carboxylate were obtained in the form of a colorless oil. Yield=97%.

Step 8:

Isopropyl (S)-1-[2-fluoro-3-(2-methoxy-3,4-dioxocyclobut-1-enylamino)benzoyl]pyrrolidine-2-carboxylate 1.80 g (0.01 mol; 2.0 eq) of 3,4-dimethoxy-3-cyclobutene-1,2-dione were added to a solution of 1.87 g (0.08 mol; 1.0 eq) of isopropyl (S)-1-(3-amino-2-fluorobenzoyl)pyrrolidine-2-carboxylate in 45 ml of methanol. The reaction medium was stirred at ambient temperature for 24 hours. The solvent was evaporated off and the residue was chromatographed on silica gel (200 g prepacked column, eluent 20/80 then 0/100 heptane/ethyl acetate). 1.32 g of isopropyl (S)-1-[2-fluoro-3-(2-methoxy-3,4-dioxocyclobut-1-enylamino)benzoyl]pyrrolidine-2-carboxylate were obtained in the form of a light yellow amorphous solid. Yield=51%.

Step 9:

Isopropyl (S)-1-[2-fluoro-3-(2-{[(5-methylfuran-2-yl)-(tetrahydrothiophen-2-yl)methyl]amino}-3,4-dioxo-cyclobut-1-enylamino)benzoyl]pyrrolidine-2-carboxylate A mixture of 600 mg (1.48 mmol; 1.0 eq) of isopropyl (S)-1-[2-fluoro-3-(2-methoxy-3,4-dioxocyclobut-1-enylamino)benzoyl]pyrrolidine-2-carboxylate and 350 mg (1.78 mmol; 1.2 eq) of (R,S)-(5-methylfuran-2-yl)-(S,R)-(tetrahydrothiophen-2-yl)methanamine (diastereoisomer 2) in solution in 25 ml of methanol was heated at 60° C. for 18 hours. The reaction medium was evaporated and the residue was chromatographed on silica gel eluted with dichloromethane/ethyl acetate (75/25). The paste obtained was crystallized from ethyl ether, filtered and dried under vacuum at 40° C. 575 mg of isopropyl (S)-1-[2-fluoro-3-(2-{[(5-methylfuran-2-yl)-(tetrahydrothiophen-2-yl)methyl]amino}-3,4-dioxo-cyclobut-1-enylamino)benzoyl]pyrrolidine-2-carboxylate were obtained in the form of a white solid. Yield=67%.

$^1$NMR (DMSO-d6, 400 MHz): 0.89 (m, 1H), 1.06 (m, 1H), 1.19-1.23 (m, 4H), 1.81-2.07 (m, 7H), 2.26 (s, 3H), 2.29 (m, 1H), 2.75-2.83 (m, 2H), 3.35(m, 2H), 3.88-3.90 (m, 1H), 4.42-4.45 (m, 1H), 4.92-4.95 (m, 1H), 5.17 (m, 1H), 6.07 (d, J=2.9 Hz, 1H), 6.33 (d, J=4 Hz, 1H), 7.01 (t, 1H), 7.26 (t, J=8 Hz, 1H), 8.04 (t, 1H), 8.55 (d, J=8 Hz, 1H), 9.63 (s, 1H).

EXAMPLE 5

Preparation of Ethyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate

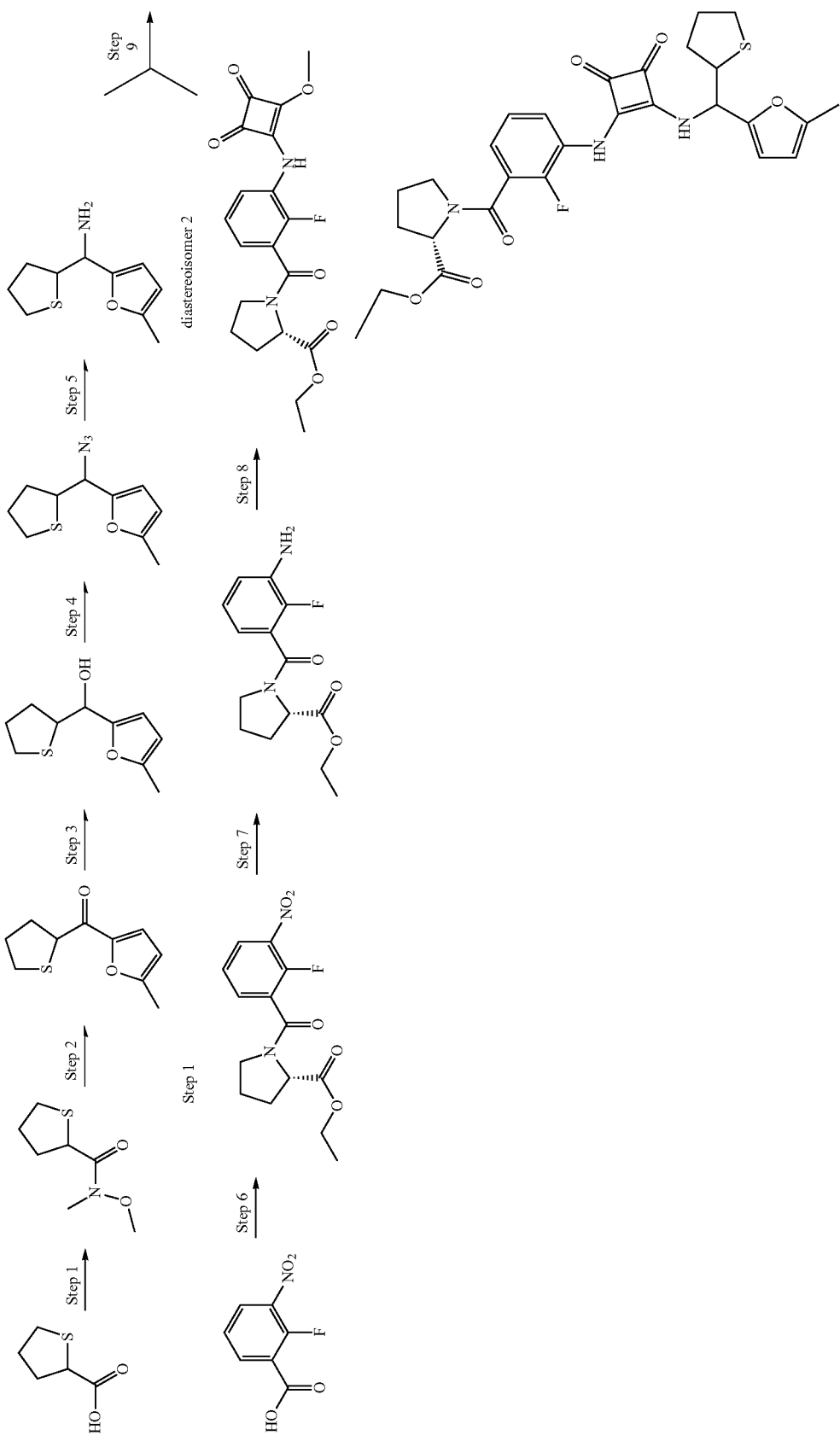

Steps 1 to 5:

In a manner analogous to EXAMPLE 2 (steps 1 to 5), (R,S)-(5-methylfuran-2-yl)-(S,R)-(tetrahydrothiophen-2-yl)methylamine (diastereoisomer 2) was prepared.

Steps 6 to 9:

In a manner analogous to EXAMPLE 2 (steps 6 to 9), and using L-proline ethyl ester hydrochloride, ethyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate was prepared. Yield=30%.

EXAMPLE 6

Preparation of Methyl (R)-1-[2-hydroxy-3-(2-{[(5-methylfuran-2-yl)-(tetrahydrothiophen-2-yl)methyl]amino}-3,4-dioxocyclobut-1-enylamino)benzoyl]pyrrolidine-2-carboxylate

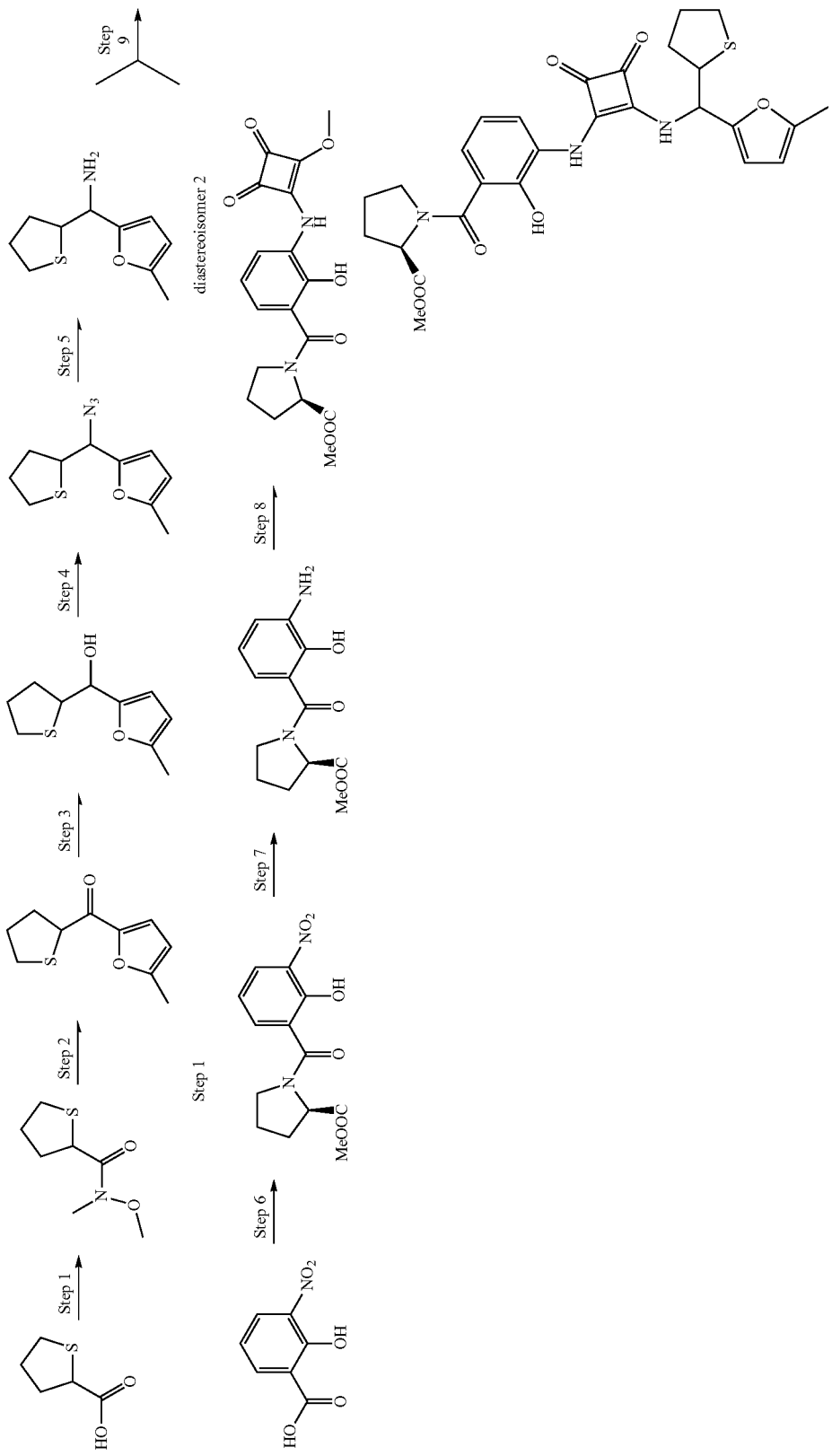

Steps 1 to 5:

In a manner analogous to EXAMPLE 2 (steps 1 to 5), (R,S)-(5-methylfuran-2-yl)-(S,R)-(tetrahydrothiophen-2-yl) methanamine (diastereoisomer 2) was prepared.

Step 6:

Methyl (R)-1-(2-hydroxy-3-nitrobenzoyl)pyrrolidine-2-carboxylate

A mixture of 3.74 g (20.4 mmol, 1 eq) of 3-nitrosalicylic acid and 14.27 g (30.6 mmol, 1.5 eq) of bromotripyrrolidinophosphonium hexafluorophosphate in 56 ml of dichloromethane and in the presence of 12.3 ml (71.5 mmol, 3.5 eq) de N,N-diisopropylethylamine was stirred at ambient temperature for 5 minutes. 5.07 g (30.6 mmol, 1.5 eq) of methyl (R)-pyrrolidine-2-carboxylate hydrochloride in solution in 10 ml of dichloromethane were added dropwise and the reaction medium was stirred at ambient temperature for 24 hours. The reaction medium was washed three times with a 1 N aqueous hydrochloric acid solution. The organic phase was dried over anhydrous sodium sulfate, filtered and evaporated. The oil obtained was chromatographed on silica gel (800 g prepacked column) eluted with heptane/ethyl acetate (gradient).

4.03 g of methyl (R)-1-(2-hydroxy-3-nitrobenzoyl)pyrrolidine-2-carboxylate were obtained in the form of a yellow foam. Yield=67%.

Step 7:

Methyl (R)-1-(3-amino-2-hydroxybenzoyl)pyrrolidine-2-carboxylate

A solution of 4.03 g (13.63 mmol; 1.0 eq) of methyl (R)-1-(2-hydroxy-3-nitrobenzoyl)pyrrolidine-2-carboxylate in 50 ml of methanol was stirred at hydrogen atmospheric pressure in the presence of 390 mg (10% by weight) of palladium on carbon at 10% for 3 days. The reaction medium was filtered through celite, rinsed with methanol and evaporated. The residue was chromatographed on silica gel (200 g prepacked column) eluted with heptane/ethyl acetate (gradient). 2.65 g of methyl (R)-1-(3-amino-2-hydroxybenzoyl)pyrrolidine-2-carboxylate were obtained in the form of a yellow oil. Yield=74%.

Step 8:

Methyl (R)-1-[2-hydroxy-3-(2-methoxy-3,4-dioxocyclobut-1-enylamino)benzoyl]pyrrolidine-2-carboxylate A mixture of 2.64 g (10 mmol, 1 eq) of methyl (R)-1-(3-amino-2-hydroxybenzoyl)pyrrolidine-2-carboxylate and 2.84 g (20 mmol, 2.0 eq) of 3,4-dimethoxy-3-cyclobutene-1,2-dione in 80 ml of ethanol was heated at 50° C. for four and a half hours. The residue was taken up with ethyl acetate and washed three times with a 1 M aqueous sodium dihydrogen phosphate solution. The organic phase was dried over anhydrous sodium sulfate, filtered and evaporated. The oil was chromatographed on silica gel (300 g prepacked column) eluted with heptane/ethyl acetate (gradient). 1.27 g of methyl (R)-1-[2-hydroxy-3-(2-methoxy-3,4-dioxocyclobut-1-enylamino)benzoyl]pyrrolidine-2-carboxylate were obtained in the form of white solid. Yield=34%.

Step 9:

Methyl (R)-1-[2-hydroxy-3-(2-{[(5-methylfuran-2-yl)-(tetrahydrothiophen-2-yl)methyl]amino}-3,4-dioxo-cyclobut-1-enylamino)benzoyl]pyrrolidine-2-carboxylate A mixture of 463 mg (1.24 mmol, 1 eq) of methyl (R)-1-[2-hydroxy-3-(2-methoxy-3,4-dioxocyclobut-1-enylamino) benzoyl]pyrrolidine-2-carboxylate and 293 mg (1.48 mmol; 1.2 eq) of (R,S)-(5-methylfuran-2-yl)-(S,R)-(tetrahydrothiophen-2-yl)methanamine (diastereoisomer 2) in solution in 15 ml of methanol was heated at 50° C. for 14 hours. The reaction medium was evaporated and the residue was chromatographed on HP silica gel (column puriFlash PF-15SI/40G, puriFlash) eluted with dichloromethane/ethyl acetate (gradient). 538 mg of methyl (R)-1-[2-hydroxy-3-(2-{[(5-methylfuran-2-yl)-(tetrahydrothiophen-2-yl)methyl] amino}-3,4-dioxocyclobut-1-enylamino)benzoyl]pyrrolidine-2-carboxylate were obtained in the form of a yellow solid. Yield=81%.

$^1$H NMR (DMSO-d6, 400 MHz): 1.82-1.99 (m, 5H), 2.03-2.05 (m, 2H), 2.26 (s, 3H), 2.75-2.84 (m, 2H), 3.59-3.67 (m, 2H), 3.84-3.88 (m, 1H), 3.89 (s, 3H), 4.53 (m, 1H), 5.19 (t, J=9.6 Hz, 1H), 6.06 (dd, J=1.0-3.0 Hz, 1H), 6.30 (d, J=3.1 Hz, 1H), 6.92 (t, J=9.6 Hz, 1H), 7.12 (d, J=6.2 Hz, 1H), 7.88 (d, J=7.9 Hz, 1H), 8.77 (d, J=9.6 Hz, 1H), 9.38 (s, 1H).

EXAMPLE 7

Preparation of Methyl (S)-1-[2-hydroxy-3-(2-{[(5-methylfuran-2-yl)-(tetrahydrothiophen-2-yl)methyl] amino}-3,4-dioxocyclobut-1-enylamino)benzoyl] pyrrolidine-2-carboxylate

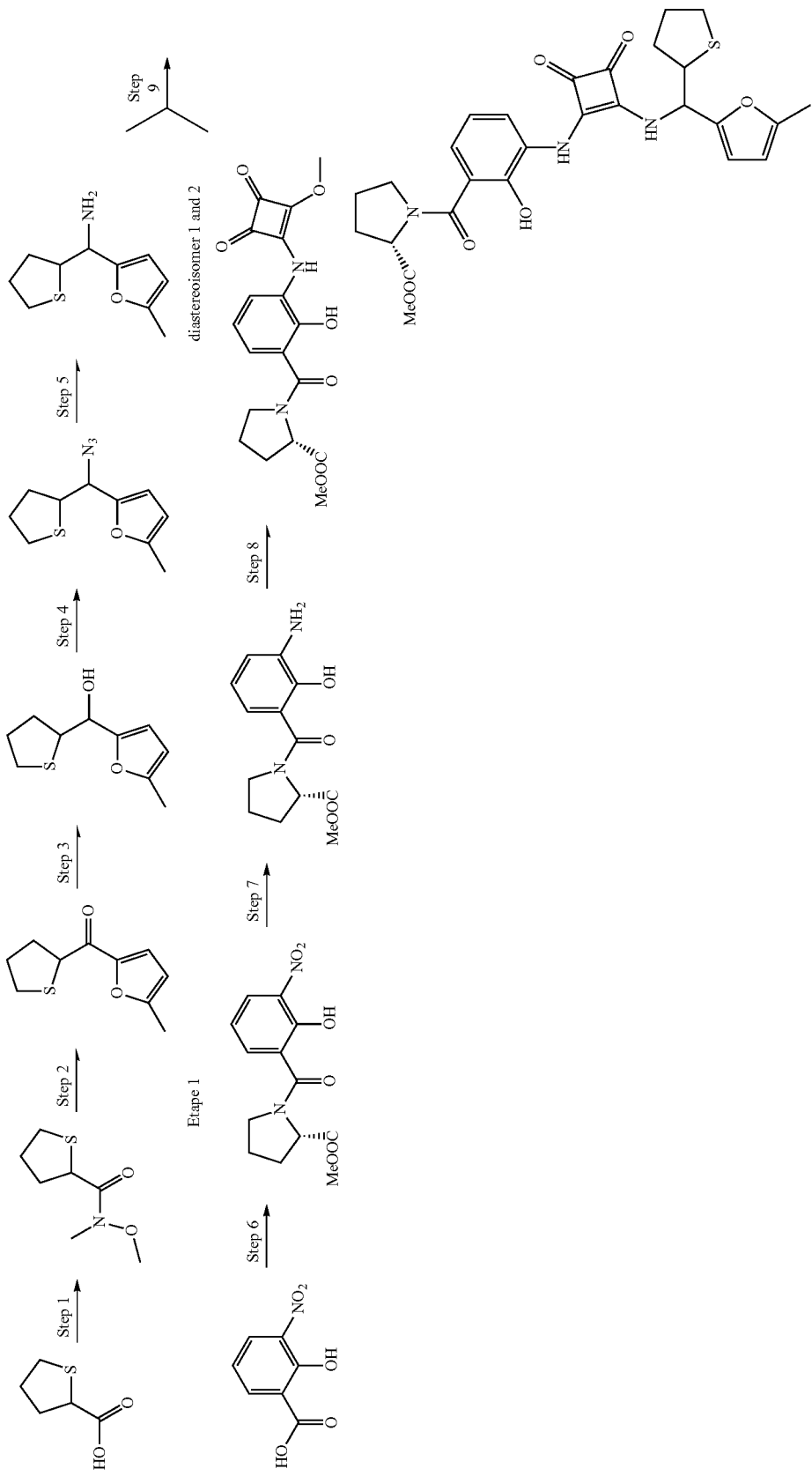

Steps 1 to 5:

In a manner analogous to EXAMPLE 2 (steps 1 to 5), (R,S)-(5-methylfuran-2-yl)-(R,S)-(tetrahydrothiophen-2-yl)methanamine and (R,S)-(5-methylfuran-2-yl)-(S,R)-(tetrahydrothiophen-2-yl)methanamine (diastereoisomers 1 and 2) was prepared.

Steps 6 to 9:

In a manner analogous to EXAMPLE 6 (steps 6 to 9), and using the hydrochloride of L-proline methyl ester and (R,S)-(5-methylfuran-2-yl)-(S,R)-(tetrahydrothiophen-2-yl)methanamine (diastereoisomer 2), methyl (S)-1-[2-hydroxy-3-(2-{[(5-methylfuran-2-yl)-(tetrahydrothiophen-2-yl)methyl]amino}-3,4-dioxocyclobut-1-enylamino)benzoyl]pyrrolidine-2-carboxylate was prepared. Yield=11%.

$^1$H NMR (DMSO-d6, 400 MHz): 1.84-1.93 (m, 4H), 2.01-2.04 (m, 2H), 2.26 (s, 3H), 2.29-2.33 (m, 1H), 2.79-2.82 (m, 2H), 3.35-3.42 (m, 1H), 3.61-3,65 (m, 2H), 3.67 (s, 3H), 3.95-3.97 (m, 1H), 4.56 (m, 1H), 5.40 (t, J=8.0 Hz, 1H), 6.06 (d, J=2.0 Hz, 1H), 6.26 (d, J=2.9 Hz, 1H), 6.92 (d, J=7.3 Hz, 1H), 7.12 (m, 1H), 7.85 (d, J=7.6 Hz, 1H), 8.84 (d, J=9.7 Hz, 1H), 9.54 (s, 1H).

Steps 6 to 9:

In a manner analogous to EXAMPLE 6 (steps 6 to 9), and using the hydrochloride of L-proline methyl ester and (R,S)-(5-methylfuran-2-yl)-(R,S)-(tetrahydrothiophen-2-yl)methanamine (diastereoisomer 1), methyl (S)-1-[2-hydroxy-3-(2-{[(5-methylfuran-2-yl)-(tetrahydrothiophen-2-yl)methyl]amino}-3,4-dioxocyclobut-1-enylamino)benzoyl]pyrrolidine-2-carboxylate was prepared. Yield=7%.

$^1$H NMR (DMSO-d6, 400 MHz): 1.64-1.68 (m, 1H), 1.88-1.93 (m, 4H), 2.03-2.06 (m, 2H), 2.27 (s, 3H), 2.76-2.81 (m, 2H), 3.38 (m, 1H), 3.61-3.64 (m, 2H), 3.67 (s, 3H), 3.85 (m, 1H), 4.52 (m, 1H), 5.18 (t, J=9.7 Hz, 1H), 6.06 (d, J=2.2 Hz, 1H), 6.30 (d, J=3.1 Hz, 1H), 6.92 (d, J=7.6 Hz, 1H), 6.94 (t, 1H), 7.12 (m, 1H), 7.85 (m, 1H), 8.77 (d, J=9.6 Hz, 1H), 9.38 (s, 1H).

EXAMPLE 8

Preparation of 2-hydroxy-N-methyl-3-(2-{[(S)-(5-methylfuran-2-yl)tetrahydrothiophen-2-ylmethyl]amino}-3,4-dioxocyclobut-1-enylamino)-N-(2,2,2-trifluoroethyl)benzamide

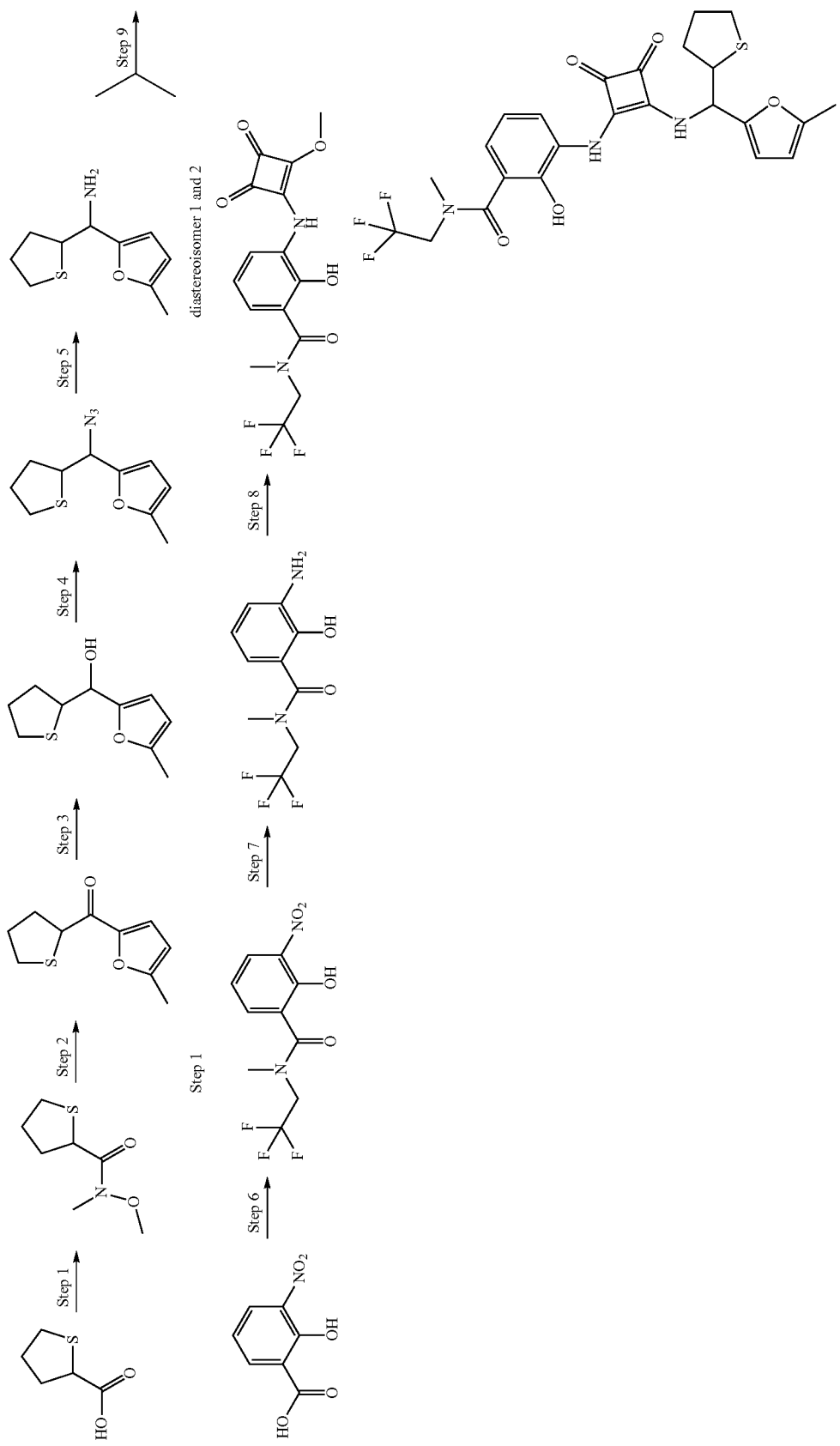

Steps 1 to 5:

In a manner analogous to EXAMPLE 2 (steps 1 to 5), (R,S)-(5-methylfuran-2-yl)-(R,S)-(tetrahydrothiophen-2-yl)methanamine and (R,S)-(5-methylfuran-2-yl)-(S,R)-(tetrahydrothiophen-2-yl)methanamine (diastereoisomers 1 and 2) was prepared.

Steps 6 to 9:

In a manner analogous to EXAMPLE 6 (steps 6 to 9), and using the hydrochloride of methyl(2,2,2-trifluoroethyl)amine and (R,S)-(5-methylfuran-2-yl)-(S,R)-(tetrahydrothiophen-2-yl)methanamine (diastereoisomer 2), 2-hydroxy-N-methyl-3-(2-{[(S)-(5-methylfuran-2-yl)tetrahydrothiophen-2-ylmethyl]amino}-3,4-dioxocyclobut-1-enylamino)-N-(2,2,2-trifluoroethyl)benzamide was prepared. Yield=8%.

$^1$H NMR (DMSO-d6, 400 MHz): 1.83 (m, 1H), 1.91 (m, 1H), 2.06 (m, 2H), 2.27 (s, 3H), 2.80 (m, 2H), 2.96 (s, 2H), 3.08 (m, 1H), 3.87 (m, 1H), 4.34 (s, 1H), 5.20 (t, J=9.6 Hz, 1H), 6.06 (d, J=2.9 Hz, 1H), 6.30 (d, J=3.0 Hz, 1H), 6.83 (d, J=7.6 Hz, 1H), 6.94 (t, J=7.8 Hz, 1H), 7.78 (d, J=8.0 Hz, 1H), 8.73 (d, J=9.6 Hz, 1H), 9.53 (s, 1H), 9.79 (s, 1H).

Steps 6 to 9:

In a manner analogous to EXAMPLE 6 (steps 6 to 9), and using the hydrochloride of methyl(2,2,2-trifluoroethyl)amine and (R,S)-(5-methylfuran-2-yl)-(S,R)-(tetrahydrothiophen-2-yl)methanamine (diastereoisomer 1), methyl (S)-1-[2-hydroxy-3-(2-{[(5-methylfuran-2-yl)-(tetrahydrothiophen-2-yl)methyl]amino}-3,4-dioxocyclobut-1-enylamino)benzoyl]pyrrolidine-2-carboxylate was prepared. Yield=10%.

$^1$H NMR (DMSO-d6, 400 MHz): 1.65 (m, 1H), 1.89 (m, 1H), 2.02 (m, 2H), 2.26 (s, 3H), 2.80 (m, 2H), 2.97 (s, 3H), 4.01 (m, 1H), 4.34 (s, 1H), 5.41 (dd, J=6.7 Hz, 9.4 Hz, 1H), 6.06 (d, J=3.0 Hz, 1H), 6.26 (d, J=3.0 Hz, 1H), 6.83 (dd, J=7.6 Hz, 1.2 Hz, 1H), 6.94 (t, J=7.8 Hz, 1H), 7.76 (d, J=8.0 Hz, 1H), 8.77 (d, J=9.6 Hz, 1H), 9.52 (s, 1H), 9.81 (s, 1H).

EXAMPLE 9

Preparation of Methyl {[2-hydroxy-3-(2-{[(5-methylfuran-2-yl)-(tetrahydrothiophen-2-yl)methyl]amino}-3,4-dioxocyclobut-1-enylamino)benzoyl]methylamino}acetate

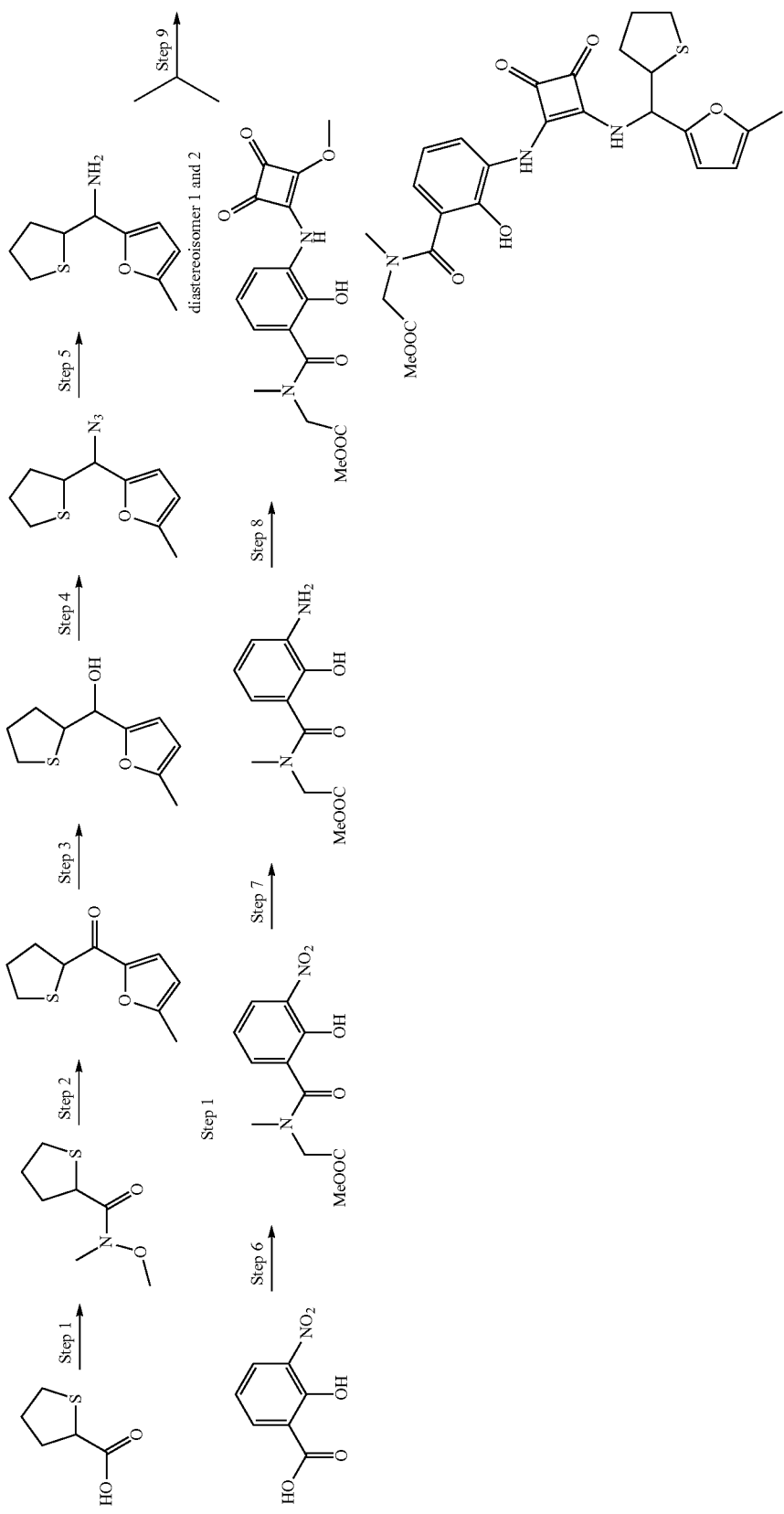

Steps 1 to 5:

In a manner analogous to EXAMPLE 2 (steps 1 to 5), diastereoisomers 1 and 2 of (5-methylfuran-2-yl)(tetrahydrothiophen-2-yl)methanamine were prepared.

Steps 6 to 9:

In a manner analogous to EXAMPLE 6 (steps 6 to 9), and using methyl methylaminoacetate and (R,S)-(5-methylfuran-2-yl)-(S,R)-(tetrahydrothiophen-2-yl)methanamine (diastereoisomer 2), methyl {[2-hydroxy-3-(2-{[(5-methylfuran-2-yl)-(tetrahydrothiophen-2-yl)methyl]amino}-3,4-dioxocyclobut-1-enylamino)benzoyl]methylamino}acetate was prepared. Yield=26%.

$^1$H NMR (DMSO-d6, 400 MHz): 1.81-1.98 (m, 2H), 2.05 (m, 2H), 2.26 (s, 3H), 2.78-2.85 (m, 2H), 2.95 (s, 3H), 3.67 (s, 3H), 3.84-3.88 (m, 1H), 4.20 (m, 2H), 5.19 (m, 1H), 6.07 (d, J=3.0 Hz, 1H), 6.30 (d, J=3.0 Hz, 1H), 6.90 (m, 1H), 7.78 (m, 1H), 8.79 (d, 1H), 9.32 (s, 1H), 10.53 (s, 1H).

Steps 6 to 9:

In a manner analogous to EXAMPLE 6 (steps 6 to 9), and using methyl methylaminoacetate and (R,S)-(5-methylfuran-2-yl)-(R,S)-(tetrahydrothiophen-2-yl)methanamine (diastereoisomer 1), methyl {[2-hydroxy-3-(2-{[(5-methylfuran-2-yl)-(tetrahydrothiophen-2-yl)methyl]amino}-3,4-dioxocyclobut-1-enylamino)benzoyl]methylamino}acetate was prepared. Yield=37%.

$^1$H NMR (DMSO-d6, 400 MHz): 1.65 (m, 1H), 1.88-1.92 (m, 2H), 1.98-2.05 (m, 2H), 2.26 (s, 3H), 2.79-2.82 (m, 2H), 2.96 (s, 3H), 3.67 (s, 3H), 3.95-4.00 (m, 1H), 4.22 (m, 2H), 5.40 (dd, 1H), 6.05 (dd, J=3.0 Hz, 1H), 6.26 (d, J=3.0 Hz, 1H), 6.90 (m, 2H), 7.76 (m, 1H), 8.80 (d, 1H), 9.52 (s, 1H), 9.81 (s, 1H).

EXAMPLE 10

Preparation of 6-chloro-2-hydroxy-N,N-dimethyl-3-(2-{[(5-methylfuran-2-yl)-(tetrahydrothiophen-2-yl)methyl]amino}-3,4-dioxocyclobut-1-enylamino)benzenesulfonamide

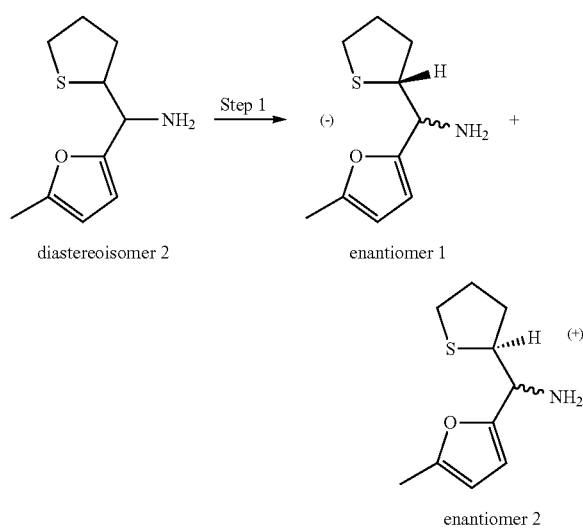

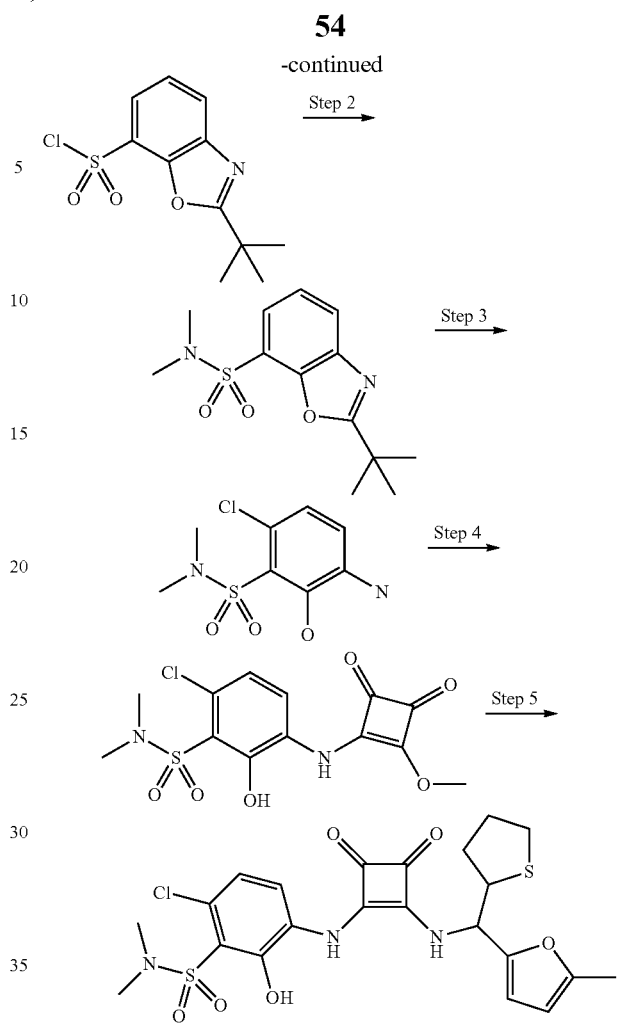

Step 1:

(R,S)-(5-Methylfuran-2-yl)-(S,R)-(tetrahydrothiophen-2-yl)methanamine

The separation of diastereoisomer 2 (prepared in EXAMPLE 2) into enantiomers was carried out on the CHIRALPACK$^R$ AD-H 5 μm and CHIRALPACK$^R$ AZ-H 5 μm semi-preparative chiral columns; mobile phase: hexane/ethanol (70/30), flow rate of 5 ml/min.

Enantiomer 1 (−) of diastereoisomer 2: 1st eluted.
Enantiomer 2 (+) of diastereoisomer 2: 2nd eluted.

Step 2:

2-tert-Butyl-6-chlorobenzooxazole-7-sulfonic Acid Dimethylamide 12.9 ml (93 mmol; 3.0 eq) of triethylamine and 93 ml of 2 M dimethylamine in tetrahydrofuran were added dropwise to a solution of 9.55 g (31 mmol; 1.0 eq) of 2-tert-butyl-6-chlorobenzoxazole-7-sulfonyl chloride in 200 ml of tetrahydrofuran cooled to 0° C. The reaction medium was stirred at 0° C. for 3 hours and was then treated with water. The reaction medium was extracted with ethyl acetate. The organic phases were combined, washed with water, dried over magnesium sulfate, filtered and evaporated. 9.12 g of 2-tert-butyl-6-chlorobenzooxazole-7-sulfonic acid dimethylamide were obtained in the form of a beige solid. Yield=93%.

Step 3:

3-Amino-6-chloro-2-hydroxy-N,N-dimethylbenzenesulfonamide 11 ml (205 mmol; 1.20 V) of sulfuric acid and 11 ml of water were added dropwise to a solution of 9.12 g (28.8 mmol; 1.0 eq) of 2-tert-butyl-6-chlorobenzooxazole-7-sulfonic acid dimethylamide in 41 ml of 1,4-dioxane. The reaction medium was refluxed for six and a half hours. The reaction medium was concentrated and 440 ml of 1 N sodium hydroxide were added (pH at 8). The solution was extracted with ethyl acetate. The organic phases were combined, dried over magnesium sulfate, filtered and evaporated. 6.94 g of 3-amino-6-chloro-2-hydroxy-N,N-dimethylbenzenesulfonamide were obtained in the form of a brown solid. Yield=96%.

Step 4:

6-Chloro-3-(2-ethoxy-3,4-dioxocyclobut-1-enylamino)-2-hydroxy-N,N-dimethylbenzenesulfonamide A mixture of 6.94 g (27.7 mmol, 1.0 eq) of 3-amino-6-chloro-2-hydroxy-N,N-dimethylbenzenesulfonamide and 9.42 g (55.4 mmol; 2.0 eq) of 3,4-diethoxy-3-cyclobutene-1,2-dione in 70 ml of ethanol was stirred at ambient temperature for 2 hours (4% product formed). The reaction medium was heated at 50° C. for 5 days. The insoluble material was filtered off and dried under vacuum at 45° C. 7.67 g of 6-chloro-3-(2-ethoxy-3,4-dioxocyclobut-1-enylamino)-2-hydroxy-N,N-dimethylbenzenesulfonamide were obtained in the form of a yellow solid. Yield=73%.

Step 5:

(−)6-Chloro-2-hydroxy-N,N-dimethyl-3-(2-{[(5-methylfuran-2-yl)-(tetrahydrothiophen-2-yl)methyl]amino}-3,4-dioxocyclobut-1-enylamino)benzenesulfonamide A mixture of 500 mg (1.33 mmol, 1.0 eq) of 6-chloro-3-(2-ethoxy-3,4-dioxocyclobut-1-enylamino)-2-hydroxy-N,N-dimethylbenzenesulfonamide and 316 mg (1.60 mmol; 1.2 eq) of (−)-(R,S)-(5-methylfuran-2-yl)-(S,R)-(tetrahydrothiophen-2-yl)methanamine in solution in 20 ml of methanol was heated at 50° C. for 16 hours. The insoluble material was filtered off, washed with a little methanol and dried under vacuum at 45° C. 615 mg of (−)-6-chloro-2-hydroxy-N,N-dimethyl-3-(2-{[(5-methylfuran-2-yl)-(tetrahydrothiophen-2-yl)methyl]amino}-3,4-dioxocyclobut-1-enylamino)benzenesulfonamide (diastereoisomer 1) were obtained in the form of an off-white solid. Yield=88%.

$^1$H NMR (DMSO-d6, 400 MHz): 1.81-1.98 (m, 2H), 2.05 (m, 2H), 2.27 (s, 3H), 2.75-2.85 (m, 2H), 2.87 (s, 6H), 3.17 (m, 2H), 3.84-3.90 (m, 1H), 4.10 (m, 1H), 5.19 (m, 1H), 6.07 (d, J=3.0 Hz, 1H), 6.31 (d, J=3.0 Hz, 1H), 7.20 (m, 1H), 8.02 (d, J=12.0 Hz, 1H), 8.84 (d, 1H), 9.48 (s, 1H), 10.53 (s, 1H).

Step 5a:

(+)-6-Chloro-2-hydroxy-N,N-dimethyl-3-(2-{[(5-methylfuran-2-yl)-(tetrahydrothiophen-2-yl)methyl]amino}-3,4-dioxocyclobut-1-enylamino)benzenesulfonamide A mixture of 500 mg (1.33 mmol, 1.0 eq) of 6-chloro-3-(2-ethoxy-3,4-dioxocyclobut-1-enylamino)-2-hydroxy-N,N-dimethylbenzenesulfonamide and 316 mg (1.60 mmol; 1.2 eq) of (+)-(R,S)-(5-methylfuran-2-yl)-(S,R)-(tetrahydrothiophen-2-yl)methanamine in solution in 20 ml of methanol was heated at 50° C. for 16 hours. The insoluble material was filtered off, washed with a little methanol and dried under vacuum at 45° C. 595 mg of (+)-6-chloro-2-hydroxy-N,N-dimethyl-3-(2-{[(5-methylfuran-2-yl)-(tetrahydrothiophen-2-yl)methyl]amino}-3,4-dioxocyclobut-1-enylamino)benzenesulfonamide (diastereoisomer 2) were obtained in the form of an off-white solid. Yield=85%.

$^1$H NMR (DMSO-d6, 400 MHz): 1.81-1.98 (m, 2H), 2.05 (m, 2H), 2.27 (s, 3H), 2.75-2.85 (m, 2H), 2.87 (s, 6H), 3.17 (m, 2H), 3.84-3.90 (m, 1H), 4.10 (m, 1H), 5.19 (m, 1H), 6.07 (d, J=3.0 Hz, 1H), 6.31 (d, J=3.0 Hz, 1H), 7.20 (m, 1H), 8.02 (d, J=12.0 Hz, 1H), 8.84 (d, 1H), 9.48 (s, 1H), 10.53 (s, 1H).

EXAMPLE 11

Preparation of 2-hydroxy-N,N-dimethyl-3-(2-{[(R)-(5-methylfuran-2-yl)tetrahydrofuran-2-ylmethyl]amino}-3,4-dioxocyclobut-1-enylamino)benzamide

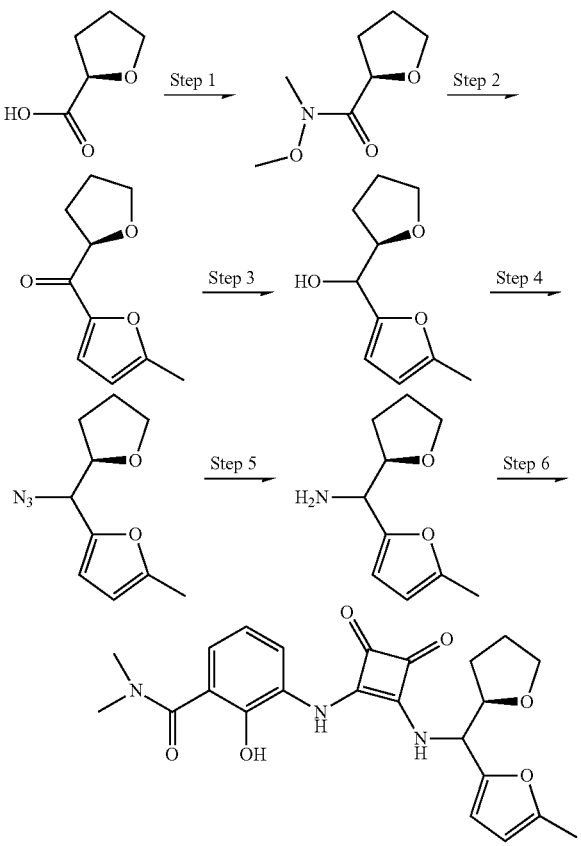

Step 1:

(R)-Tetrahydrofuran-2-methoxymethylcarboxamide 8.0 ml (110.1 mmol; 1.28 eq) of thionyl chloride were added dropwise, at ambient temperature, over the course of 15 minutes, to a solution of 10.0 g (86.1 mmol; 1.0 eq) of tetrahydrofuran-2-carboxylic acid in 50 ml of dichloromethane. The reaction medium was stirred at ambient temperature for 2 hours until no more gas was given off. The dichloromethane and the excess thionyl chloride were evaporated off under vacuum and the residue was co-evaporated three times with 50 ml of dichloromethane. The acid chloride obtained was solubilized in 50 ml of dichloromethane, and 9.24 g (94.7 mmol; 1.10 eq) of N,O-dimethylhydroxylamine hydrochloride were added. The reaction medium was cooled to 0° C. and a mixture of 27.5 ml (207.0 mmol; 2.40 eq) of triethylamine in 50 ml of dichloromethane was added dropwise over the course of 90 minutes (while maintaining the temperature below 5° C.). After the addition, the reaction medium was stirred at ambient temperature for one hour and was then washed with 250 ml of a 1 M aqueous hydrochloric acid solution, The aqueous phase was extracted with 50 ml of dichloromethane. The organic phases were combined, washed with 50 ml of a saturated aqueous sodium hydrogen phosphate solution, dried over anhydrous magnesium sulfate, filtered and evaporated. 8.5 g of (R)-tetrahydrofuran-2-methoxymethylcarboxamide were obtained in the form of an oil. Yield=62%, Step 2:

(5-Methylfuran-2-yl)-(R)-tetrahydrofuran-2-ylmethanone 87 ml (215.6 mmol; 1.50 eq) of n-butyllithium at 2.5 M in hexane were added dropwise to a solution of 19.5 ml (215.6 mmol; 1.50 eq) of 2-methylfuran in 550 ml of tetrahydrofuran cooled to −78° C. The mixture was allowed to return to ambient temperature for 2 hours and was then cooled to −78° C. A solution of 22.88 g (143.7 mmol; 1.00 eq) of (R)-tetrahydrofuran-2-methoxymethylcarboxamide in 200 ml of tetrahydrofuran was added and the reaction mixture was left at 0° C. for 2 hours. The reaction medium was diluted with 200 ml of ethyl acetate and then washed with 300 ml of a 1 N aqueous hydrochloric acid solution. The aqueous phase was separated and extracted with 200 ml of ethyl acetate. The organic phases were combined, washed with a saturated sodium chloride solution, dried over anhydrous magnesium sulfate, filtered and evaporated. The brown oil obtained was filtered on silica (eluent: 90/10 heptane/ethyl acetate). 17.72 g of (5-methylfuran-2-yl)-(R)-tetrahydrofuran-2-ylmethanone were obtained. Yield=68%.

Step 3:

(5-Methylfuran-2-yl)-(R)-tetrahydrofuran-2-ylmethanol 2.27 g (59.9 mmol; 1.20 eq) of sodium borohydride were added in small portions to a solution of 9.00 g (49.9 mmol; 1.0 eq) of (5-methylfuran-2-yl)-(R)-tetrahydrofuran-2-ylmethanone in 100 ml of tetrahydrofuran cooled to 0° C. The reaction medium was stirred at ambient temperature for 3 hours. The reaction medium was poured into 200 ml of ethyl acetate and then 100 ml of water were added. The aqueous phase was extracted with ethyl acetate and then the organic phases were combined, washed with a saturated sodium chloride solution, dried over anhydrous magnesium sulfate, filtered and evaporated. 8.10 g de (5-methylfuran-2-yl)-(R)-tetrahydrofuran-2-ylmethanol were obtained. Yield=92%.

Step 4:

2-((R)-Azidotetrahydrofuran-2-ylmethyl)-5-methylfuran 11.9 ml (55.3 mmol; 1.2 eq) of diphenylphosphoryl azide and then 8.3 ml (55.3 mmol; 1.2 eq) of 1,8-diazabicyclo[5.4.0]undec-7-ene were added dropwise to a solution of 8.40 g (46.1 mmol; 1.0 eq) of (5-methylfuran-2-yl)-(R)-tetrahydrofuran-2-ylmethanol in 300 ml of toluene cooled to 0° C. The mixture was allowed to return to ambient temperature gently and was then stirred for 24 hours. The reaction medium was treated with water and extracted with ethyl acetate, The organic phases were combined, washed with a 1 M sodium dihydrogen phosphate solution, dried over magnesium sulfate, filtered and evaporated. The residue was chromatographed on silica gel (column puriFlash IR-50SI/300G, puriFlash) eluted with heptane/ethyl acetate (90/10). 6.0 g of 2-((R)-azidotetrahydrofuran-2-ylmethyl)-5-methylfuran were obtained (mixture of the 2 diastereoisomers). Yield=63%.

Step 5:

(R,S)-(5-Methylfuran-2-yl)-[(R)-tetrahydrofuran-2-yl]methanamine

A solution of 6.00 g (29.0 mmol; 1.0 eq) of 2-((R)-azidotetrahydrofuran-2-ylmethyl)-5-methylfuran in 250 ml of methanol and in the presence of 600 mg (10% by weight) of Pd/C 10% was stirred at ambient temperature at hydrogen atmospheric pressure for 5 days. The reaction medium was filtered through celite and the filtrate was evaporated. The residue was chromatographed on silica gel (column puriFlash IR-50SI-STD/300G, puriFlash) eluted with dichloromethane/ethyl acetate (gradient). 4.6 g of (R,S)-(5-methylfuran-2-yl)-[(R)-tetrahydrofuran-2-yl]methanamine were obtained (mixture of the 2 diastereoisomers). Yield=70%.

Step 6:

2-Hydroxy-N,N-dimethyl-3-(2-{[(R)-(5-methylfuran-2-yl)tetrahydrofuran-2-ylmethyl]amino}-3,4-dioxocyclobut-1-enylamino)benzamide A mixture of 4.5 g (14.7 mmol; 1.0 eq) of 3-(2-ethoxy-3,4-dioxocyclobut-1-enylamino)-2-hydroxy-N,N-dimethylbenzamide and 2.7 g (14.7 mmol; 1.0 eq) of (R,S)-(5-methylfuran-2-yl)((R)-tetrahydrofuran-2-yl)methanamine in solution in 100 ml of methanol was stirred at 50° C. overnight. The reaction medium was evaporated and purified by chromatography on silica gel (eluent: 70/30 dichloromethane/ethyl acetate) and was recrystallized from a heptane/dichloromethane mixture (75/25). 5.6 g of 2-hydroxy-N,N-dimethyl-3-(2-{[(R)-(5-methylfuran-2-yl)tetrahydrofuran-2-ylmethyl]amino}-3,4-dioxocyclobut-1-enylamino)benzamide were obtained. Yield=54%.

$^1$H NMR (DMSO-d6, 400 MHz): 1.75-1.80 (m, 2H), 1.80-1.87 (m, 1H), 1.88-2.02 m, 1H), 2.27 (d, J=1.8 Hz, 3H), 2.94 (s, 6H), 3.65-3.75 (m, 2H), 4.24-4.26 (m, 1H), 5.32 (dd, $J_1$=9.2 Hz, $J_2$=5.6 Hz, 1H), 6.06 (dd, $J_1$=1.0 Hz, $J_2$=3.0 Hz, 1H), 6.28 (d, J=3.1 Hz, 1H), 6.87 (m, 2H), 7.77 (m, 1H), 8.84 (m, 1H), 9.45 (s, 1H), 9.95 (s, 1H).

EXAMPLE 12

Preparation of 2-hydroxy-N,N-dimethyl-3-(2-{[(S)-(5-methylfuran-2-yl)tetrahydrofuran-2-ylmethyl]amino}-3,4-dioxocyclobut-1-enylamino)benzamide

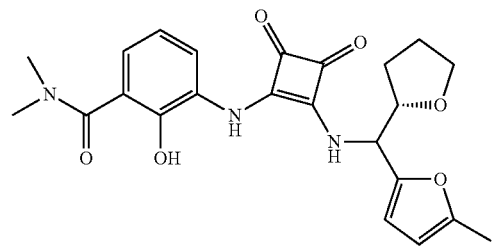

In a manner analogous to EXAMPLE 11 (steps 1 to 6), 2-hydroxy-N,N-dimethyl-3-(2-{[(S)-(5-methylfuran-2-yl)tetrahydrofuran-2-ylmethyl]amino}-3,4-dioxocyclobut-1-enylamino)benzamide was prepared.

$^1$H NMR (DMSO-d6, 400 MHz); 1.50-1.80 (m, 2H); 1.84 (m, 1H); 1.98 (m, 1H); 2.27 (s, 3H); 2.93 (s, 6H); 3.60-3.80 (m, 2H); 4.24 (m, 1H); 5.20-5.40 (m, 1H); 6.05 (d, J=2.0 Hz,

1H); 6.28 (d, J=3.0 Hz, 1H), 6.87 (m, 2H); 7.77 (m, 1H); 8.81 (d, J=9.6 Hz, 1H), 9.46 (s, 1H), 9.97 (s, 1H).

EXAMPLE 13

Preparation of 3-(3,4-dioxo-2-{[phenyl(tetrahydrofuran-2-yl)methyl]amino}cyclobut-1-enylamino)-2-hydroxy-N,N-dimethylbenzamide

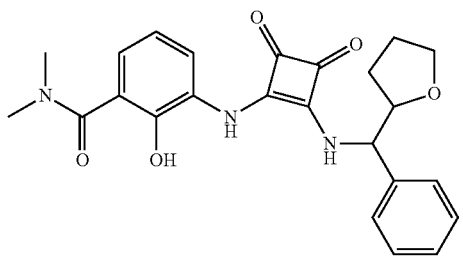 [SMILES: CN(C)C(=O)c1cccc(Nc2c(NC(c3ccccc3)C3CCCO3)c(=O)c2=O)c1O]

In a manner analogous to EXAMPLE 1 (steps 6 to 9), and using commercial phenyl(tetrahydrofuran-2-yl)methanamine and 3-(2-methoxy-3,4-dioxocyclobut-1-enylamino)-2-hydroxy-N,N-dimethylbenzamide, 3-(3,4-dioxo-2-{[phenyl(tetrahydrofuran-2-yl)methyl]aminocyclobut-1-enylamino)-2-hydroxy-N,N-dimethylbenzamide was prepared. (mixture of diastereoisomers) (Mp=120-125° C.). LC/MS: 99.66% [435].

$^1$H NMR (DMSO-d6, 400 MHz): 1.57-1.91 (m, 5H); 2.94 (s, 6H); 3.64-3.73 (m, 2H); 3.84-3.93 (m, 1H); 4.19-4.28 (m, 1H); 5.27 (t, 1H); 6.85 (d, J=6.2 Hz, 2H); 7.3-7.42 (m, 6H); 7.73 (dd, J=8.1 Hz, 1H); 8.86-8.96 (dd, J=9.6 Hz, 1H).

EXAMPLE 14

Preparation of 3-(2-{[((R)-2,2-dimethyl-[1,3]dioxolan-4-yl)-(5-methylfuran-2-yl)methyl]amino}-3,4-dioxocyclobut-1-enylamino)-2-hydroxy-N,N-dimethylbenzamide (diastereoisomers 1 and 2)

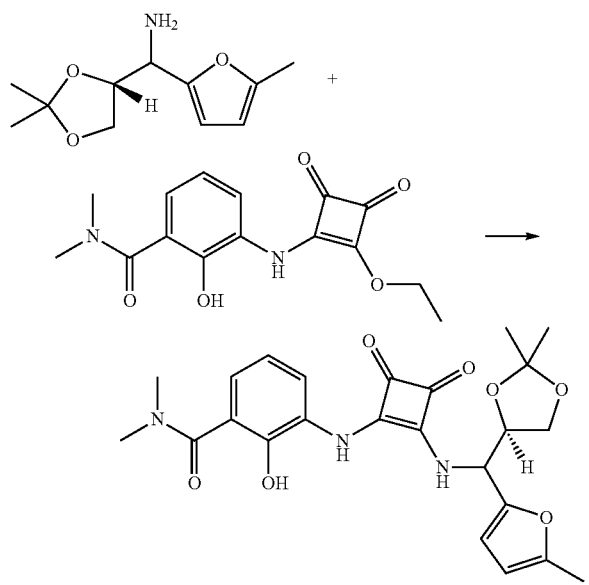

In a manner analogous to EXAMPLE 1 (steps 3 to 5), and using (S)-glyceraldehyde acetonide, (R,S)-((R)-2,2-dimethyl-1,3-dioxolan-4-yl)(5-methylfuran-2-yl)methanamine was prepared. Yield=10%.

The separation of the 2 diastereoisomers was carried out at the level of the azide intermediate (2nd step described below).

(R)-4-[Azido-(5-methylfuran-2-yl)methyl]-2,2-dimethyl-[1,3]dioxolane 4.15 g (15.0 mmol, 1.2 eq) of diphenylphosphoryl azide were added dropwise to a solution of 2.67 g (12.5 mmol, 1 eq) of crude ((S)-2,2-dimethyl-[1,3]dioxolan-4-yl)-(5-methylfuran-2-yl)methanol in 40 ml of toluene. The reaction medium was cooled to 0° C. and then 2.2 ml (15.0 mmol, 1.2 eq) of 1,8-diazabicyclo[5.4.0]undec-7-ene were added dropwise. The reaction medium was stirred at ambient temperature for 42 hours. The reaction medium (heterogeneous) was separated by settling out, treated with water and extracted with ethyl acetate. The organic phases were combined, washed with a 1 N sodium dihydrogen phosphate solution, dried over magnesium sulfate, filtered and evaporated. The residue was chromatographed on silica gel (column puriFlash IR-50SI/200G, Spot II, then column RediSep Rf Gold 40g, Spot II) eluted with heptane/ethyl acetate (95/5).

562 mg of (R)-4-[azido-(5-methylfuran-2-yl)methyl]-2,2-dimethyl-[1,3]dioxolane (diastereoisomer 1) were obtained.

257 mg of (R)-4-[azido-(5-methylfuran-2-yl)methyl]-2,2-dimethyl-[1,3]dioxolane (diastereoisomer 2) were obtained.

In a manner analogous to EXAMPLE 1 (steps 6 to 9), and using the two ((R)-2,2-dimethyl-1,3-dioxolan-4-yl)(5-methylfuran-2-yl)methanamine diastereoisomers and 3-(2-ethoxy-3,4-dioxocyclobut-1-enylamino)-2-hydroxy-N,N-dimethylbenzamide, diastereoisomers 1 and 2 of 3-(2-{[((R)-2,2-dimethyl-[1,3]dioxolan-4-yl)-(5-methylfuran-2-yl)methyl]amino}-3,4-dioxocyclobut-1-enylamino)-2-hydroxy-N,N-dimethylbenzamide were prepared. Yield of 78% (diastereoisomer 1) and 52% (diastereoisomer 2).

3-(2-{[((R)-2,2-dimethyl-[1,3]dioxolan-4-yl)-(5-methylfuran-2-yl)methyl]amino}-3,4-dioxocyclobut-1-enylamino)-2-hydroxy-N,N-dimethylbenzamide (diastereoisomer 1)

$^1$H NMR (DMSO-d6, 400 MHz): 1.27 (s, 3H); 1.29 (s, 3H); 2.27 (s, 3H); 2.94 (s, 6H); 3.86 (m, 1H); 4.14 (m, 1H); 4.49 (q, J=5.9 Hz, 1H); 5.43 (dd, J=9.4 Hz, 1H); 6.06 (dd, J=3.0 Hz, 1H), 6.30 (d, J=3.1 Hz, 1H); 6.87 (dd, J=6.8 Hz, 2H); 7.76 (dd, J=6.7 Hz, 1H); 8.82 (d, J=9.6 Hz, 1H); 9.40 (s, 1H).

3-(2-{[((R)-2,2-dimethyl-[1,3]dioxolan-4-yl)-(5-methylfuran-2-yl)methyl]amino}-3,4-dioxocyclobut-1-enylamino)-2-hydroxy-N,N-dimethylbenzamide (diastereoisomer 2)

$^1$H NMR (DMSO-d6, 400 MHz): 1.30 (s, 3H); 1.36 (s, 3H); 2.27 (s, 3H); 2.93 (s, 6H); 3.67 (q, J=5.5 Hz, 1H); 4.06 (q, J=6.8 Hz, 1H); 4.51 (q, J=6.6 Hz, 1H); 5.32 (dd, J=9.3 Hz,

1H); 6.07 (dd, J=3.0 Hz, 1H), 6.35 (d, J=3.1 Hz, 1H); 6.87 (m, 2H); 7.76 (dd, J=7.1 Hz, 1H); 8.76 (d, J=9.5 Hz, 1H); 9.40 (s, 1H); 9.92 (s, 1H).

EXAMPLE 15

Preparation of Methyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate

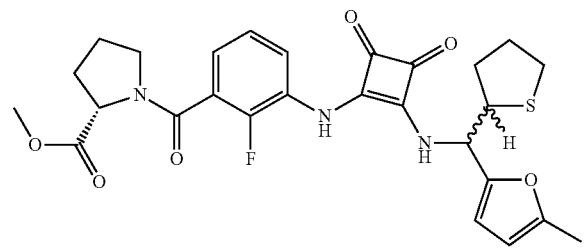

In a manner analogous to EXAMPLE 2 (steps 1 to 5), (R,S)-(5-methylfuran-2-yl)-(R,S)-(tetrahydrothiophen-2-yl)methanamine (diastereoisomer 1) was prepared.

In a manner analogous to EXAMPLE 2 (steps 6 to 9), and using the hydrochloride of L-proline methyl ester, methyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate was prepared.

$^1$H NMR (DMSO-d6, 400 MHz): 1.66 (m, 1H), 1.85-2.05 (2m, 6H), 2.26 (s, 3H), 2.30 (m, 1H), 2.80-2.83 (m, 2H), 3.35-3.38 (m, 2H), 3.46-3.68 (2s, 3H), 4.02 (m, 1H), 4.32-4.53 (2m, 1H), 5.40 (t, J=9.0 Hz, 1H), 6.06 (d, J=3.0 Hz, 1H), 6.28 (d, J=3.0 Hz, 1H), 7.02 (t, J=6.2 Hz, 1H), 7.27 (t, J=7.9 Hz, 1H), 8.05 (t, J=8.1 Hz, 1H), 8.63 (d, J=9.6 Hz, 1H), 9.83 (s, 1H).

EXAMPLE 16

Preparation of 3-(2-hydroxypyridin-3-ylamino)-4-{[5-methylfuran-2-yl)-(tetrahydrothiophen-2-yl)methyl]amino}cyclobut-3-ene-1,2-dione

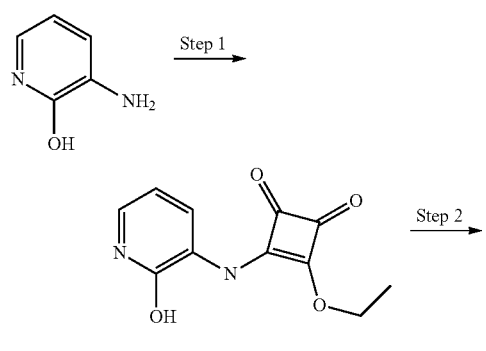

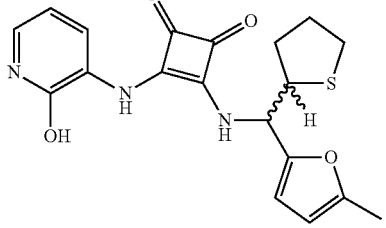

In a manner analogous to EXAMPLE 2 (steps 1 to 5), (R,S)-(5-methylfuran-2-yl)-(S,R)-(tetrahydrothiophen-2-yl)methylamine (diastereoisomer 2) was prepared.

Step 1:
3-Ethoxy-4-(2-hydroxypyridin-3-ylamino)cyclobut-3-ene-1,2-dione

A mixture of 1.82 g (16.5 mmol, 1 eq) of 3-aminopyridin-2-ol and 3.6 ml (24.8 mmol, 1.5 eq) of 3,4-diethoxycyclobut-3-ene-1,2-dione (3.6 ml, 24.8 mmol) in solution in 87 ml of ethanol was stirred at ambient temperature for 16 hours and then heated at 50° C. for 3 days with formation of a precipitate. Ethanol was added in order to promote the fall of the precipitate, which was filtered off, washed with diethyl ether and dried under vacuum at 45° C. 3.47 g of 3-ethoxy-4-(2-hydroxypyridin-3-ylamino)cyclobut-3-ene-1,2-dione were obtained in the form of a brown solid. Yield=90%.

Step 2:
3-(2-Hydroxypyridin-3-ylamino)-4-{[(5-methylfuran-2-yl)-(tetrahydrothiophen-2-yl)methyl]amino}cyclobut-3-ene-1,2-dione A mixture of 500 mg (2.1 mmol, 1.0 eq) of 3-ethoxy-4-(2-hydroxypyridin-3-ylamino)cyclobut-3-ene-1,2-dione and 505 mg (2.6 mmol; 1.2 eq) of (5-methylfuran-2-yl)(tetrahydrofuran-2-yl)methanamine in solution in 20 ml of methanol was heated at 50° C. for 18 hours. The reaction medium was evaporated and the residue was chromatographed on silica gel with said deposition (column puriFlash PF-15SI/40G, puriFlash) eluted with dichloromethane/methanol (gradient). The solid was taken up with a little diethyl ether, filtered and dried under vacuum at 45° C. 610 mg of 3-(2-hydroxypyridin-3-ylamino)-4-{[(5-methylfuran-2-yl)-(tetrahydrothiophen-2-yl)methyl]amino}cyclobut-3-ene-1,2-dione were obtained in the form of an off-white solid. Yield=74%.

$^1$H NMR (DMSO-d6, 400 MHz): 1.79-1.84 (m, 1H), 1.88-1.92 (m, 1H), 2.00-2.06 (m, 2H), 2.26 (s, 3H), 2.75-2.83 (m, 2H), 3.81-3.86 (m, 1H), 5.17 (t, 1H), 6.05 (d, J=2.1 Hz, 1H), 6.23-6.28 (m, 2H), 7.08 (dd, J=6.5-1.5 Hz, 1H), 8.01 (dd, J=7.3-1.5 Hz, 1H), 9.00 (d, 1H), 9.53 (s, 1H), 11.98 (s, 1H)

EXAMPLE 17

Preparation of 3-{[(5-methylfuran-2-yl)-(tetrahydrothiophen-2-yl)methyl]amino}-4-(1-methyl-2-oxo-1,2-dihydropyridin-3-ylamino)cyclobut-3-ene-1,2-dione

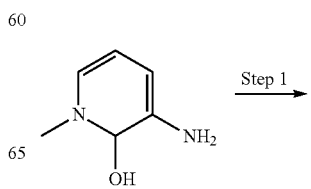

-continued

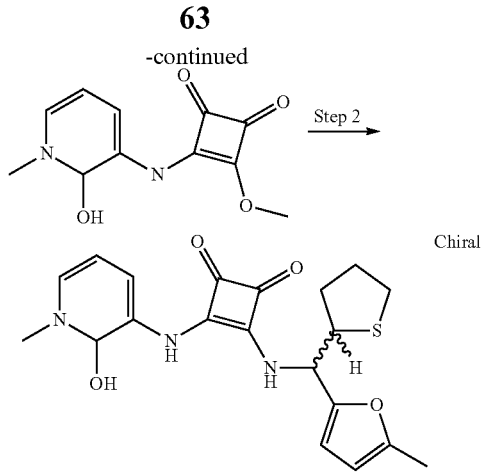

In a manner analogous to EXAMPLE 2 (steps 1 to 5), (R,S)-(5-methylfuran-2-yl)-(S,R)-(tetrahydrothiophen-2-yl) methanamine (diastereoisomer 2) was prepared.

Step 1:
3-Methoxy-4-(1-methyl-2-oxo-1,2-dihydropyridin-3-ylamino)cyclobut-3-ene-1,2-dione In a manner analogous to EXAMPLE 16 (step 1), and using 3,4-dimethoxy-cyclobut-3-ene-1,2-dione, 3-methoxy-4-(1-methyl-2-oxo-1,2-dihydropyridin-3-ylamino)cyclobut-3-ene-1,2-dione was prepared. Yield=50%.

Step 2:
3-{[(5-Methylfuran-2-yl)-(tetrahydrothiophen-2-yl)methyl]amino}-4-(1-methyl-2-oxo-1,2-dihydropyridin-3-ylamino)cyclobut-3-ene-1,2-dione In a manner analogous to EXAMPLE 16 (step 2), 3-{[(5-methylfuran-2-yl)-(tetrahydrothiophen-2-yl)methyl]amino}-4-(1-methyl-2-oxo-1,2-dihydropyridin-3-ylamino)cyclobut-3-ene-1,2-dione was prepared. Yield=90%.

$^1$H NMR (DMSO-d6, 400 MHz): 1.77-1.84 (m, 1H), 1.86-1.94 (m, 1H), 1.98-2.08 (m, 2H), 2.26 (s, 3H), 2.73-2.85 (m, 2H), 3.52 (s, 3H), 3.82-3.88 (m, 1H), 5.18 (t, J=9.5 Hz, 1H), 6.05-6.07 (m, 1H), 6.25-6.30 (m, 2H), 7.40 (dd, J=6.8 Hz, J=1.6 Hz, 1H), 7.99 (dd, J=7.4 Hz, J=1.6 Hz, 1H), 9.02 (d, J=9.6 Hz, 1H), 9.57 (s, 1H)

EXAMPLE 18

Preparation of (−)-2-hydroxy-N-methyl-3-(2-{[(S)-(5-methylfuran-2-yl)-(tetrahydrothiophen-2-yl)methyl]amino}-3,4-dioxocyclobut-1-enylamino)-N-(2,2,2-trifluoroethyl)benzamide

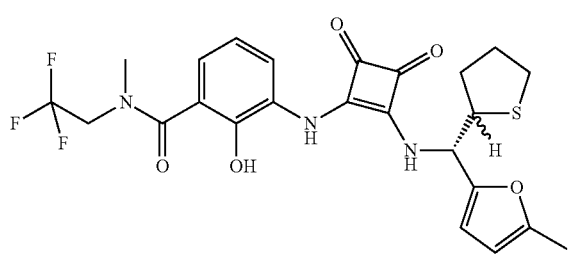 [SMILES: Cc1ccc([C@H](Nc2c(Nc3cccc(C(=O)N(C)CC(F)(F)F)c3O)c(=O)c2=O)C2CCCS2)o1]

In a manner analogous to EXAMPLE 10 (step 1), (−)-(R,S)-(5-methylfuran-2-yl)((R)-tetrahydrothiophen-2-yl) methanamine (enantiomer 1) was prepared.

In a manner analogous to EXAMPLE 8 (steps 6 to 9), and using (−)-(R,S)-(5-methylfuran-2-yl)-((R)-tetrahydrothiophen-2-yl)methanamine (enantiomer 1), (−)-2-hydroxy-N-methyl-3-(2-{[(S)-(5-methylfuran-2-yl)-(tetrahydrothiophen-2-yl)methyl]amino}-3,4-dioxo-cyclobut-1-enylamino)-N-(2,2,2-trifluoroethyl)benzamide was prepared. Yield=22%.

$^1$H NMR (DMSO-d6, 400 MHz): 1.91 (m, 1H), 1.96 (m, 1H), 2.05 (m, 1H), 2.27 (s, 3H), 2.81 (m, 2H), 2.96 (s, 3H), 3.86 (m, 1H), 4.11 (m, 1H), 4.33 (s, 1H), 5.20 (t, J=9.6 Hz, 1H), 6.06 (dd, J=0.9 Hz, 3.0 Hz, 1H), 6.30 (d, J=3.1 Hz, 1H), 6.82 (d, J=6.5 Hz, 1H), 6.92 (s, 1H), 7.78 (d, J=8.4 Hz, 1H), 8.72 (d, J=9.2 Hz, 1H), 9.34 (s, 1H), 9.79 (s, 1H)

EXAMPLE 19

Preparation of Methyl (−)-{[2-hydroxy-3-(2-{[(S)-(5-methylfuran-2-yl)-(tetrahydrothiophen-2-yl)methyl]amino}-3,4-dioxocyclobut-1-enylamino)benzoyl]methylamino}acetate

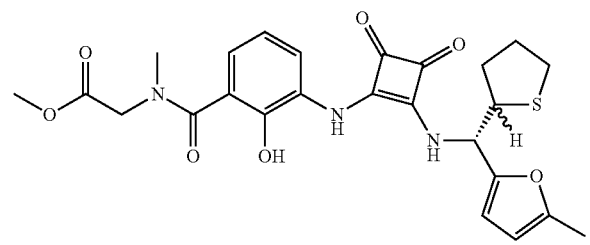

In a manner analogous to EXAMPLE 10 (step 1), (−)-(R,S)-(5-methylfuran-2-yl)((R)-tetrahydrothiophen-2-yl) methanamine (enantiomer 1) was prepared.

In a manner analogous to EXAMPLE 6 (steps 6 to 9), and using methyl methylaminoacetate and (−)-(R,S)-(5-methylfuran-2-yl)((R)-tetrahydrothiophen-2-yl)methanamine (enantiomer 1), methyl (−)-{[2-hydroxy-3-(2-{[(S)-(5-methylfuran-2-yl)-(tetrahydrothiophen-2-yl)methyl]amino}-3,4-dioxo-cyclobut-1-enylamino)benzoyl]methylamino}acetate was prepared. Yield=25%.

$^1$H NMR (DMSO-d6, 400 MHz): 1.80-1.96 (m, 2H), 1.99-2.10 (m, 2H), 2.37 (s, 3H), 2.74-2.85 (m, 2H), 2.95 (bs, 3H), 3.67 (bs, 3H), 3.83-3.89 (m, 1H), 4.00-4.35 (m, 2H), 5.20 (t, J=9.6 Hz, 1H), 6.05-6.07 (m, 1H), 6.30 (d, J=3.1 Hz, 1H), 6.65-6.95 (m, 2H), 7.80 (d, J=7.8 Hz, 1H), 8.77 (d, J=9.6 Hz, 1H), 9.36 (m, 1H), 9.82 (m, 1H)

EXAMPLE 20

Preparation of Methyl (−)-1-[2-hydroxy-3-(2-{[((S)-5-methylfuran-2-yl)-(tetrahydrothiophen-2-yl)methyl]amino}-3,4-dioxocyclobut-1-enylamino)benzoyl]pyrrolidine-2-(R)-carboxylate

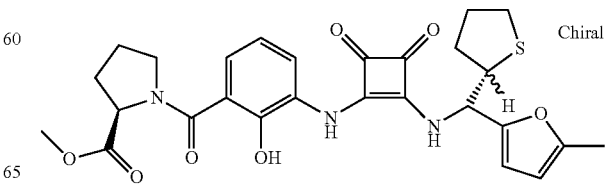

In a manner analogous to EXAMPLE 10 (step 1), (−)-(R,S)-(5-methylfuran-2-yl)((R)-tetrahydrothiophen-2-yl)methanamine (enantiomer 1) was prepared.

In a manner analogous to EXAMPLE 6 (steps 6 to 9), and using L-proline methyl ester and (−)-(R,S)-(5-methylfuran-2-yl)((R)-tetrahydrothiophen-2-yl)methanamine (enantiomer 1), methyl (−)-1-[2-hydroxy-3-(2-{[((S)-5-methylfuran-2-yl)-(tetrahydrothiophen-2-yl)methyl]amino}-3,4-dioxocyclobut-1-enylamino)benzoyl]pyrrolidine-2-(R)-carboxylate was prepared. Yield=7%.

$^1$H NMR (DMSO-d6, 400 MHz): 1.87-1.97 (m, 5H), 1.99-2.10 (m, 2H), 2.21-2.33 (m, 4H), 2.73-2.85 (m, 2H), 3.56-3.70 (m, 5H), 3.83-3.89 (m, 1H), 4.50-4.60 (m, 1H), 5.20 (t, J=9.6 Hz, 1H), 6.05-6.07 (m, 1H), 6.30 (d, J=3.1 Hz, 1H), 6.91 (t, J=7.9 Hz, 1H), 7.12 (d, J=7.5 Hz, 1H), 7.88 (d, J=7.8 Hz, 1H), 8.78 (d, J=9.5 Hz, 1H), 9.37 (m, 1H), 10.98 (m, 1H).

EXAMPLE 21

Preparation of (−)-6-chloro-2-hydroxy-N,N-dimethyl-3-(2-{[((S)-5-methylfuran-2-yl)-(tetrahydrothiophen-2-yl)methyl]amino}-3,4-dioxocyclobut-1-enylamino)benzamide

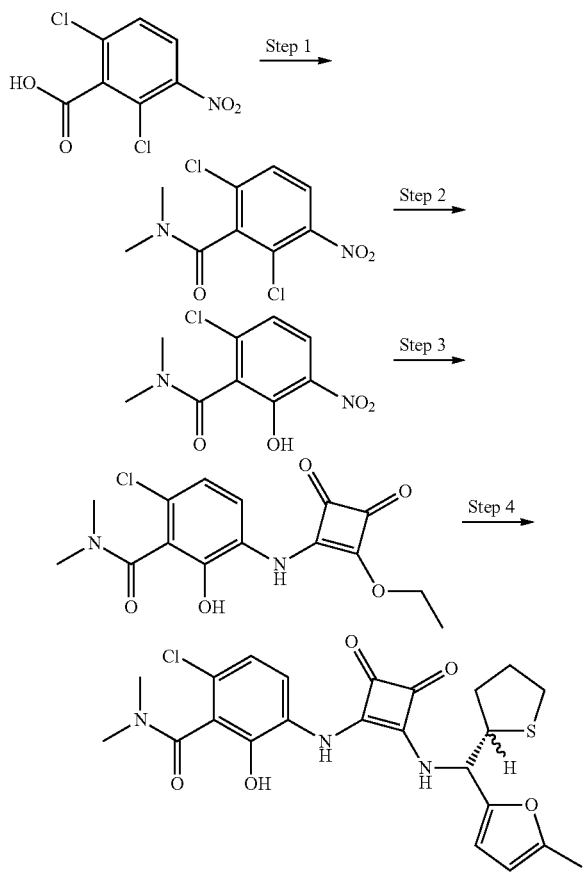

In a manner analogous to EXAMPLE 10 (step 1), (−)-(R,S)-(5-methylfuran-2-yl)((R)-tetrahydrothiophen-2-yl)methanamine (enantiomer 1) was prepared.

Step 1:
2,6-Dichloro-N,N-dimethyl-3-nitrobenzamide

A solution of 10.0 g (42.4 mmol, 1 eq) of 2,6-dichloro-3-nitrobenzoic acid in 50 ml of thionyl chloride was refluxed for 2 hours. The reaction medium was concentrated and co-evaporated with toluene. The residue was taken up in 35 ml of tetrahydrofuran and then 48 ml of a solution of dimethylamine in tetrahydrofuran was added dropwise. After 20 minutes of stirring at ambient temperature, water was added, as was ethyl acetate. The organic phase was washed with water, dried over anhydrous sodium sulfate, filtered and concentrated. 11.36 g of 2,6-dichloro-N,N-dimethyl-3-nitrobenzamide were obtained in the form of a yellow oil. Quantitative yield.

Step 2:
6-Chloro-2-hydroxy-N,N-dimethyl-3-nitrobenzamide 3.2 ml (177.6 mmol, 4.2 eq) of water and 11.04 g (41.96 mmol; 1.0 eq) of 2,6-dichloro-N,N-dimethyl-3-nitrobenzamide (41.96 mmol; 1.00 eq.) in solution in 130.00 ml of tetrahydrofuran were added to a suspension of 7.16 g (179.01 mmol; 4.3 eq) of sodium hydride in 250 ml of tetrahydrofuran cooled to 0° C. After 10 minutes, the reaction medium was stirred at ambient temperature for 19 hours. The reaction medium was hydrolyzed with a 1 N aqueous hydrochloric acid solution and extracted with ethyl acetate. The organic phase was washed with a 1 N aqueous hydrochloric acid solution, dried over anhydrous sodium sulfate, filtered and concentrated. The residue (11.82 g) was chromatographed on silica gel (300 g prepacked column, eluent heptane/ethyl acetate from 40 to 80% of ethyl acetate, 150 ml/min). 6.10 g of 6-chloro-2-hydroxy-N,N-dimethyl-3-nitrobenzamide were obtained in the form of a yellow solid. Yield=59%.

Step 3:
6-Chloro-3-(2-ethoxy-3,4-dioxocyclobut-1-enylamino)-2-hydroxy-N,N-dimethylbenzamide A solution of 5.96 g (24.4 mmol, 1 eq) of 6-chloro-2-hydroxy-N,N-dimethyl-3-nitrobenzamide in 100 ml of methanol in the presence of 0.58 g of platinum oxide hydrate was stirred at hydrogen atmospheric pressure for 3 hours. The reaction medium was filtered through celite and the filtrate was concentrated. The solution obtained was added dropwise to 8.0 g (48.8 mmol, 2 eq) of 3,4-diethoxy-3-cyclobutene-1,2-dione in solution in 50 ml of methanol. The reaction medium was stirred at ambient temperature for 18 hours. The solvent was evaporated off and the residue was chromatographed on silica gel (300 g prepacked column, eluent heptane/acetone, from 50 to 100% of acetone). 4.42 g of 6-chloro-3-(2-ethoxy-3,4-dioxocyclobut-1-enylamino)-2-hydroxy-N,N-dimethylbenzamide were obtained in the form of a beige solid. Yield=54%.

Step 4:
(−)-6-Chloro-2-hydroxy-N,N-dimethyl-3-(2-{[((S)-5-methylfuran-2-yl)-(tetrahydrothiophen-2-yl)methyl]amino}-3,4-dioxo-cyclobut-1-enylamino)benzamide A mixture of 560 mg (2.83 mmol, 1.2 eq) of (−)-(R,S)-(5-methylfuran-2-yl)((R)-tetrahydrothiophen-2-yl)methanamine (enantiomer 1, prepared in EXAMPLE 10, step 1) and 800 mg (2.36 mmol, 1 eq) of 6-chloro-3-(2-ethoxy-3,4-dioxocyclobut-1-enylamino)-2-hydroxy-N,N-dimethylbenzamide in 50 ml of methanol was heated at 50° C. for 23 hours. The methanol was evaporated off and the residue was taken up with ethyl acetate and washed with a 1 M aqueous sodium dihydrogen phosphate solution. The organic phase was dried over anhydrous sodium sulfate, filtered and concentrated. The residue (0.90 g) was chromatographed on silica gel (120 g prepacked column, eluent dichloromethane/methanol, from 0 to 10% of methanol). 530 mg of (−)-6-chloro-2-hydroxy-N,N-dimethyl-3-(2-{[((S)-5-methylfuran-2-yl)-(tetrahydrothiophen-2-yl)methyl]amino}-3,4-dioxocyclobut-1-enylamino)benzamide were obtained in the form of a brown solid. Yield=45%. Mp=153-154° C.

¹H NMR (DMSO-d6, 400 MHz); 1.75-1.95 (m, 2H), 2.00-2.10 (m, 2H), 2.26 (s, 3H), 2.73-2.85 (m, 5H), 3.00 (s, 1H), 3.75-3.90 (m, 1H), 5.15-5.22 (m, 1H), 6.05 (s, 1H), 6.27-6.30 (m, 1H), 6.98 (bd, J=8.5 Hz, 1H), 7.73-7.77 (m, 1H), 8.73-8.78 (m, 1H), 9.37 (m, 1H), 9.90-10.30 (m, 1H).

EXAMPLE 22

Preparation of (−)-3-[4-chloro-2-hydroxy-3-(4-methylpiperazine-1-sulfonyl)phenylamino]-4-{[(5-methylfuran-2-yl)-(tetrahydrothiophen-2-yl)methyl]amino}cyclobut-3-ene-1,2-dione

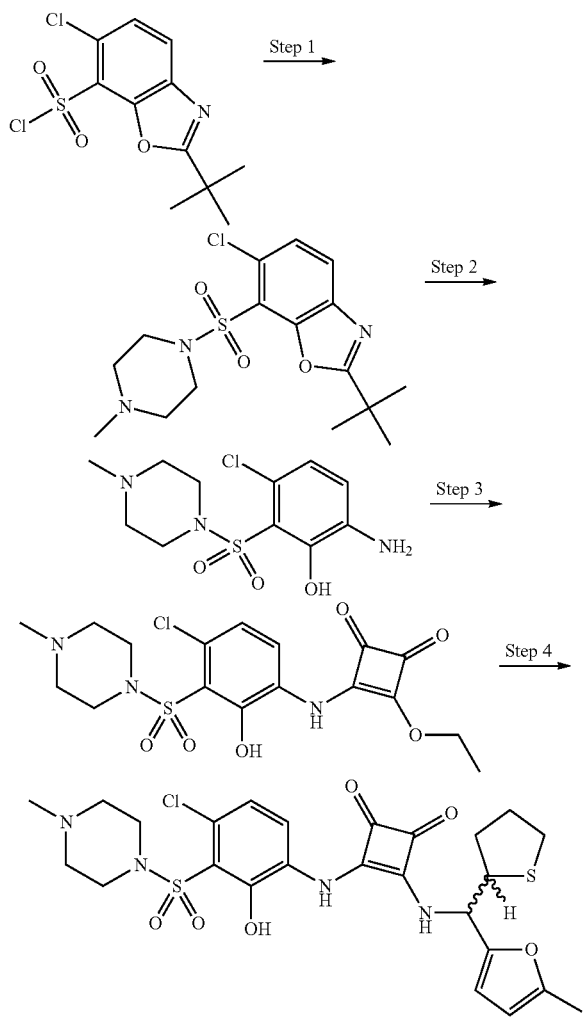

In a manner analogous to EXAMPLE 10 (step 1), (−)-(R,S)-(5-methylfuran-2-yl)((R)-tetrahydrothiophen-2-yl) methanamine (enantiomer 1) was prepared.

Step 1:
2-tert-Butyl-6-chloro-7-(4-methylpiperazine-1-sulfonyl)benzooxazole 1.62 ml (11.68 mmol; 1.2 eq) of triethylamine followed by 1.20 ml (10.71 mmol; 1.1 eq) of 1-methylpiperazine were added to a solution of 3.0 g (9.73 mmol; 1.0 eq) of 2-tert-butyl-6-chlorobenzoxazole-7-sulfonyl chloride (commercial ?) in 45 ml of tetrahydrofuran. The reaction medium was stirred at ambient temperature for 2 hours. Water was added and the reaction medium was extracted with ethyl acetate. The organic phases were combined, dried over magnesium sulfate, filtered and evaporated. 3.57 g of 2-tert-butyl-6-chloro-7-(4-methylpiperazine-1-sulfonyl)benzooxazole were obtained in the form of a tacky brown foam. Yield=98%.

Step 2:
6-Amino-3-chloro-2-(4-methylpiperazine-1-sulfonyl)phenol 4.27 ml (0.08 mol; 1.20 V) of sulfuric acid diluted in 4.3 ml of water were added dropwise to 3.56 g of 2-tert-butyl-6-chloro-7-(4-methylpiperazine-1-sulfonyl)benzooxazole (0.01 mol; 1.0 eq) in solution in 15 ml of 1,4-dioxane. The reaction medium was refluxed for six and a half hours. The reaction medium was concentrated and 1 N sodium hydroxide was added (to pH 7). The solution was extracted with dichloromethane. The organic phases were combined, dried over magnesium sulfate, filtered and evaporated. The residue obtained was chromatographed on silica gel, eluent 95/5 ethyl acetate/dichloromethane. 2.0 g of 6-amino-3-chloro-2-(4-methylpiperazine-1-sulfonyl)phenol were obtained in the form of a thick brown oil. Yield=68%.

Step 3:
3-[4-Chloro-2-hydroxy-3-(4-methylpiperazine-1-sulfonyl)phenylamino]-4-ethoxycyclobut-3-ene-1,2-dione A mixture of 1.98 g (6.5 mmol, 1 eq) of 6-amino-3-chloro-2-(4-methylpiperazine-1-sulfonyl)phenol and 2.20 g (48.8 mmol, 2 eq) of 3,4-diethoxy-3-cyclobutene-1,2-dione was placed in solution in 20 ml of ethanol. The reaction medium was heated at 50° C. for 16 hours. The insoluble material was filtered off, washed with ethanol and dried under vacuum at 45° C. 2.05 g of 3-[4-chloro-2-hydroxy-3-(4-methylpiperazine-1-sulfonyl)phenylamino]-4-ethoxycyclobut-3-ene-1,2-dione were obtained in the form of a yellow solid. Yield=74%.

Step 4:
(−)-3-[4-Chloro-2-hydroxy-3-(4-methylpiperazine-1-sulfonyl)phenylamino]-4-{[(5-methylfuran-2-yl)-(tetrahydrothiophen-2-yl)methyl]amino}cyclobut-3-ene-1,2-dione A mixture of 280 mg (1.4 mmol, 1.2 eq) of (−)-(R,S)-(5-methylfuran-2-yl)-((R)-tetrahydrothiophen-2-yl)methanamine (enantiomer 1, prepared in EXAMPLE 10, step 1) and 500 mg (1.16 mmol, 1 eq) of 3-[4-chloro-2-hydroxy-3-(4-methylpiperazine-1-sulfonyl)phenylamino]-4-ethoxycyclobut-3-ene-1,2-dione in 20 ml of methanol was heated at 50° C. for 20 hours. The methanol was evaporated off and the residue was taken up with dichloromethane and washed with a 1 M aqueous sodium dihydrogen phosphate solution. The organic phase was dried over anhydrous sodium sulfate, filtered and evaporated. The residue was chromatographed on silica gel eluted with dichloromethane/methanol (98/2). 410 mg of 3-[4-chloro-2-hydroxy-3-(4-methylpiperazine-1-sulfonyl)phenylamino]-4-{[(5-methylfuran-2-yl)-(tetrahydrothiophen-2-yl)methyl]amino}cyclobut-3-ene-1,2-dione were obtained in the form of a bright yellow solid. Yield=61%.

¹H NMR (DMSO-d6, 400 MHz): 1.81-1.85 (m, 1H); 1.90-1.93 (m, 1H); 1.99-2.09 (m,2H); 2.26 (s, 3H); 2.41 (s,3H); 2.68 (bs, 4H); 2.74-2.84 (m, 2H); 3.36 (bs, 4H); 3.83-3.88 (m, 1H); 5.19 (t, j=9.6 Hz, 1H); 6.06 (m, 1H); 6.29 (m, 1H); 6.80 (bs, 1H); 7.90 (d, j=8.6 Hz, 1H); 8.91 (d, j=9.6 Hz, 1H); 9.48 (s, 1H); 10.00 (bs, 1H).

BIOLOGICAL TESTS

EXAMPLE 23

In Vitro Affinity

The in vitro affinity of the compounds of the present invention for the CXCR1 and CXCR2 receptors was determined on a functional test of the β-arrestin recruitment after receptor activation type.

It was demonstrated that the activation by CXCL8 of the CXCR2 receptor in cells of the PathHunter HEK293-CXCR2 line or of the CXCR1. receptor in cells of the U2OS h CXCR1 β-arrestin line results in the recruitment of β-arrestin (Richardson, R. M., R. J. Marjoram, L. S. Barak, R. Snyderman. 2003. Role of the cytoplasmic tails of CXCR1 and CXCR2 in mediating leukocyte migration, activation, and regulation. J. Immunol. 170: 2904-2911).

In order to evaluate the direct interaction of the CXCR2 or CXCR1 receptor with β-arrestin 2, a β-arrestin 2 recruitment test for CXCR2 or CXCR1 based on β-galactosidase enzyme complementation (Olson K R, Eglen R M. Beta galactosidase complementation: a cell-based luminescent assay platform for drug discovery. Assay Drug Dev Technol. 2007 February; 5(1); 137-44), as established by DiscoveRx Corporation was used. The stimulation of these two cell lines with CXCL8 (10 nM) induces β-arrestin 2 recruitment, as indicated by a significant increase in the induction factor. All the CXCR2 antagonists were tested in a dose-dependent manner and the concentration corresponding to 50% inhibition of the response was determined ($IC_{50}$=half inhibition concentration).

β-Arrestin recruitment test: "PathHunter HEK293-CXCR2" or "U2OS hCXCR1 β-arrestin" cells (DiscoveRx Corporation) were seeded overnight at 10 000 cells/well (384-well format) in 20 μl of Opti MEM I medium. A preincubation with the antagonist or the vehicle for 30 min at 37° C. and 5% $CO_2$ was followed by 60 minutes of stimulation with CXCL8 at 37° C. and 5% $CO_2$. The cells were then placed at ambient temperature for 30 minutes. The PathHunter detection reagent (DiscoveRx Corporation) was added. After incubation for 60 min at ambient temperature, the β-galactosidase induced by the luminescence during the β-arrestin-CXCR2 interaction was measured for 0.3 s in an Envision 2102 Multilabel Reader (PerkinElmer Life and Analytical Sciences). The data were analyzed by means of a non-linear curve procedure using the XLFit4 exploitation software (IDBS) and the IC50 values were determined.

| Compound Example No. | CXCR1 (IC50; nM) | CXCR2 (IC50; nM) |
|---|---|---|
| 1 (Enantiomer 2 of diastereoisomer 2) | 244 | 53 |
| 1 (Diastereoisomer 1) | 2075 | 89 |
| 1 (Diastereoisomer 2) | 819 | 94 |
| 1 (Enantiomer 1 of diastereoisomer 2) | 9999* | 9999* |
| 2 (Enantiomer 1 of diastereoisomer 2) | 77 | 15 |
| 2 (Diastereoisomer 2) | 44 | 35 |
| 2 (Enantiomer 2 of diastereoisomer 1) | 692 | 56 |
| 2 (Enantiomer 2 of diastereoisomer 2) | 1564 | 134 |
| 2 (Diastereoisomer 1) | 661 | 135 |
| 2 (Enantiomer 1 of diastereoisomer 1) | 4554 | 273 |
| 3 (Enantiomer 1) | 552 | 195 |
| 3 (Mixture of enantiomers 1 and 2) | 812 | 221 |
| 3 (Enantiomer 2) | 8907 | 982 |
| 4 | 1892 | 109 |
| 5 | 711 | 106 |
| 6 | 108 | 30 |
| 7 (Diastereoisomer 2) | 171 | 37 |
| 7 (Diastereoisomer 1) | 859 | 86 |
| 8 (Diastereoisomer 2) | 85 | 47 |
| 8 (Diastereoisomer 1) | 508 | 115 |
| 9 (Diastereoisomer 2) | 89 | 80 |
| 9 (Diastereoisomer 1) | 580 | 153 |
| 10 (Diastereoisomer 1) | 20 | 16 |
| 10 (Diastereoisomer 2) | 1096 | 272 |
| 11 | 1322 | 176 |
| 12 | 483 | 83 |
| 13 | 1148 | 170 |
| 14 (Diastereoisomer 2) | 9999* | 1253 |
| 14 (Diastereoisomer 1) | 9999* | 9999* |
| 15 | 3808 | 294 |
| 16 | 652 | 23 |
| 17 | 384 | 44 |
| 18 | 36 | 15 |
| 19 | 42 | 20 |
| 20 | 43 | 21 |
| 21 | 113 | 69 |
| 22 | 30 | 17 |

*9999 signifies not active

EXAMPLE 24

Polypharmacology: "Receptor Profiling"

Measurement of calcium flux on cells: The experiments were carried out on the FLIPR TETRA® platform from Molecular Devices. After the basal level had been read, the compounds were added to the cells expressing the chemokine receptor of interest and the agonist activity was read at 10 seconds. After a further incubation for 10 minutes, the cells were activated, with a concentration equivalent to the AC80, using a reference agonist in order to detect whether this compound exhibits antagonist activity.

Each cell line expressing a chemokine receptor was established on the basis of the Chem-1 cell stably expressing the recombinant form of the chemokine receptor and also an associated G protein, with the aim of coupling the receptor to the calcium signalling pathway.

21 receptors belonging to the chemokine receptor family (CCRs and CXCRs) were analyzed. All the CXCR2 antagonists were tested in a dose-dependent manner and the concentration corresponding to 50% inhibition of the response was determined ($IC_{50}$).

The compounds corresponding to the general formula (I) and also the Schering compound SCH-527123 were profiled on a panel of 20 chemokine receptors. It emerges from this profiling that the compounds corresponding to the general formula (I) exhibit polypharmacology. For example, the compound of example 1 (enantiomer 2 of diastereoisomer 2) inhibits the CCR4, CCR6, CCR7 and CXCR3 receptors with respective IC50 values of 410 nM, 2.0 nM, 8.7 µM and 1.3 nM. The compound of example 2 (diastereoisomer 2) inhibits the CCR4, CCR6, CCR7, CCR8, CXCR3 and FPR1 receptors with the respective IC50 values of 52 nM, 4.4 nM, 1.5 µM, 620 nM, 1.7 µM and 6.5 µM.

The Schering compound SCH-527123 was inactive or not very active at all on all these receptors. It was also extremely interesting to note the strong activity of the compound of example 1 (enantiomer 2 of diastereoisomer 2) and of the compound of example 2 (diastereoisomer 2) on CXCR3 and CCR6.

| Antagonist | IC50 (nM) | | |
|---|---|---|---|
| | CCR4 | CCR6 | CXCR3 |
| Example 1 (Enantiomer 2 of diastereoisomer 2) | 410 | 2.0 | 1.3 |
| Example 2 (diastereoisomer 2) | 52 | 8 | 1700 |
| Example 1 (diastereoisomer 2) | ND | 2.2 | 55 |
| Example 2 (Enantiomer 1 of diastereoisomer 2) | 250 | 6 | 216 |
| Example 6 | ND | 9.7 | 140 |
| Example 10 | 39 | 1.6 | 93 |
| Example 18 | 97 | 60 | 450 |
| Example 19 | 8.1 | 11 | 510 |
| Example 20 | 7.2 | 8.8 | 180 |
| Example 22 | 9.4 | 2.2 | 150 |

ND: not determined

EXAMPLE 25

Dissociation Constant

The determination of the half-dissociation constants of the CXCR2 antagonists was based on the in vitro β-arrestin recruitment model previously described: "PathHunter HEK293-CXCR2" cells (DiscoveRx Corporation) were seeded overnight at 20 000 cells/well (in a 96-well format) in 100 µl/well of OptiMEM culture medium-1% FCS. A preincubation with the antagonist or the vehicle was carried out for 1 hour at 37° C.-5% $CO_2$. The cells were then washed 3 times with 100 µl/well of OptiMEM medium-1% FCS and then a variable incubation (0 h-0.5 h-6 h-12 h-24 h) of the cells at 37° C.-5% $CO_2$ was carried out. The cells were then stimulated with 4 nM of CXCL8 at 37° C.-5% $CO_2$ for 1 h 30. The PathHunter detection reagent (DiscoveRx Corporation) was added in a proportion of 50 µl/well. After incubation for 60 minutes at ambient temperature, the luminescence emitted, via the hydrolysis of the substrate by the β-galactosidase complemented during the β-arrestin-CXCR2 interaction, was measured for 0.3 seconds/well with an Envision Multilabel Reader (PerkinElmer Life and Analytical Sciences). The data were analyzed by means of a non-linear curve procedure using the XLFit4 exploitation software (IDBS) and the IC50 values were determined. The half-dissociation time was determined on a regression of type $y=(A*(1-\exp(((-1)*B)*x)))$ (where x=time and y=standardized luminescence) at saturating concentration of antagonist.

Results: The molecules described in the examples of the invention were compared to the SCH-527123 molecule (described as having a pseudo-irreversible dissociation) (Pharmacological Characterization of SCH-527123, a Potent Allosteric CXCR1/CXCR2 Antagonist. JPET 322:477-485, 2007).

EXAMPLE 26

A/ Metabolic Stabilities in Hepatic Microsomes

Hepatic microsomes (Becton Dickinson) were incubated at a protein concentration of 0.5 mg/ml in the reaction medium.

The reaction medium of the microsomes was composed of phosphate buffer, pH: 7.4 at 100 mM, of $MgCl_2$ at 100 mM (50/50), of an ATP-generating system composed of a mixture of nicotinamide adenine diphosphate (NADP), of glucose-6-phosphate (G6P) at 1 mg/ml and of glucose-6-phosphate dehydrogenase (G6PDH) at 4 U/ml. The compounds were tested at 1 µM (0.1% DMSO).

The samples of incubation medium after addition of the microsomes were taken at times 5, 10, 15, 30 and 60 minutes. At each time, the metabolic reaction was stopped by adding methanol (1 volume incubation medium/3 volumes of methanol). The disappearance of the parent product was measured by LC/MS/MS analysis. The time for which 50% of parent product disappeared (T1/2) was calculated from the kinetics of disappearance of the parent product as a function of time.

| Antagonist | Half-life time (min) |
|---|---|
| SCH-527123 | Stable (>60 min) |
| Example 2 (diastereoisomer 2) | 11 |
| Example 1 (diastereoisomer 2) | 27 |
| Example 2 (diastereoisomer 1) | 9 |
| Example 3 (pair of enantiomers 1 and 2) | 3 |
| Example 6 | 5 |
| Example 10 | 8 |
| Example 18 | 15 |
| Example 19 | 8 |
| Example 20 | 17 |
| Example 22 | 7 |

B/ Metabolic stabilities in hepatocytes

The human hepatocytes were supplied by Biopredic in 24-well plates. After 48 h of adaptation in culture, the hepatocytes were placed in a treatment medium containing 0.1% bovine serum albumin, and the compounds were tested at 1 µM (0.1% DMSO).

The samples of incubation medium after addition of the test compound were taken at times t=0, 1, 2, 4, 6 and 24 hours.

At each time, the metabolic reaction was stopped by adding methanol (1 volume incubation medium/3 volumes of methanol). The disappearance of the parent product was measured by LC/MS/MS analysis. The time for which 50% (T1/2) of parent product disappeared was calculated from the kinetics of disappearance of the parent product as a function of time.

| Antagonist | Half-life time (min) |
|---|---|
| SCH-527123 | 900 |
| Example 1 (Enantiomer 2 of diastereoisomer 2) | 300 |

-continued

| Antagonist | Half-life time (min) |
|---|---|
| Example 1 (diastereoisomer 2) | 539 |
| Example 2 (diastereoisomer 1) | 106 |
| Example 2 (Enantiomer 2 of diastereoisomer 2) | 229 |
| Example 3 (pair of enantiomers 1 and 2) | 141 |
| Example 2 (Enantiomer 1 of diastereoisomer 2) | 213 |
| Example 10 | 124 |
| Example 18 | 82 |
| Example 19 | 214 |
| Example 20 | 211 |
| Example 22 | 49 |

The invention claimed is:

1. A disubstituted 3,4-diamino-3-cyclobutene-1,2-dione compound corresponding to general formula (I) below, or a pharmaceutically acceptable salt or solvate thereof:

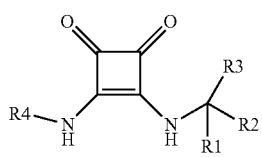

(I)

in which:
R1 represents a hydrogen atom or a methyl,
R2 represents a ring having five atoms, selected from the group consisting of structures (1), (2), (3) and (4) below:

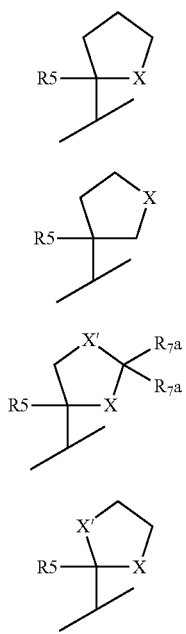

in which R5, $R_{7a}$, X and X' have the meaning given hereinafter,

R3 represents an aromatic or heteroaromatic ring selected from the group consisting of the rings corresponding to formulae (a) to (o) below:

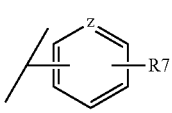
(a)

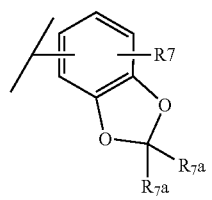
(b)

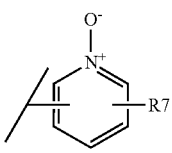
(c)

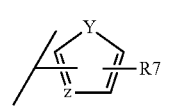
(d)

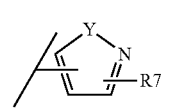
(e)

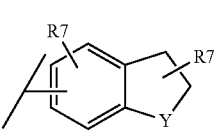
(f)

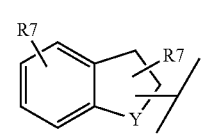
(g)

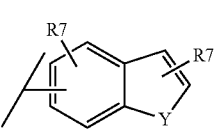
(h)

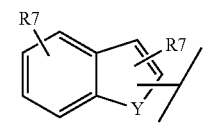
(i)

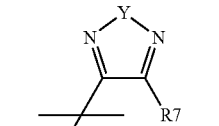
(j)

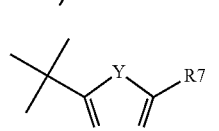
(k)

-continued

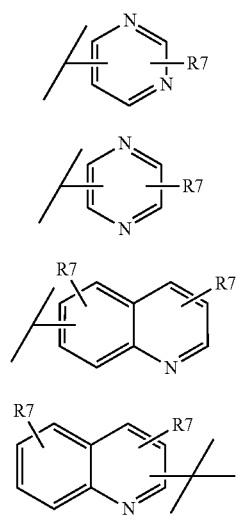

(l)

(m)

(n)

(o)

in which R7, R7a, Y and Z have the meaning given hereinafter, it being specified that the rings (a) to (o) can optionally bear several R7 groups, which are identical or different, the total number of such R7 groups being at most equal to the number of substitutable atoms of the ring;

X and X', which are identical or different, represent an oxygen atom, a sulfur atom, or a nitrogen atom substituted with an R6 radical;

R4 represents an aromatic or heteroaromatic ring selected from the group consisting of the rings corresponding to formulae (p) to (z) and (aa) to (ak) below:

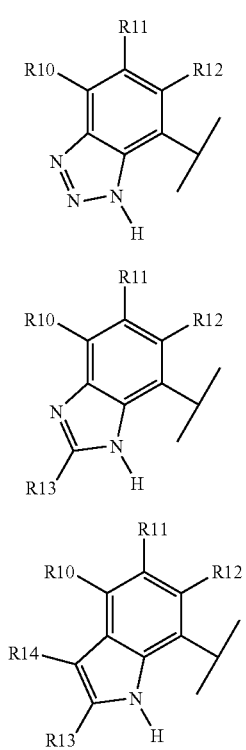

(p)

(q)

(r)

-continued

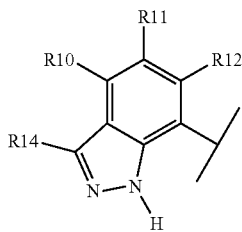

(s)

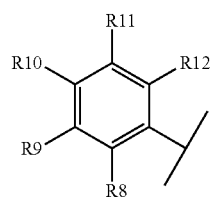

(t)

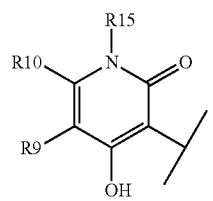

(u)

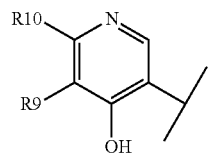

(v)

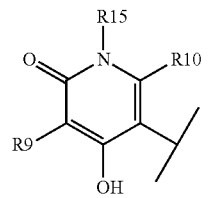

(w)

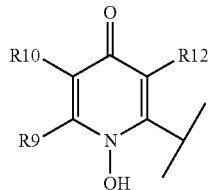

(x)

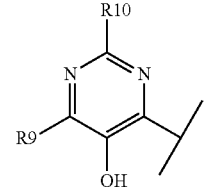

(y)

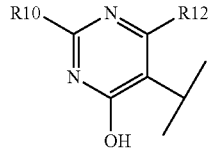

(z)

-continued (aa) 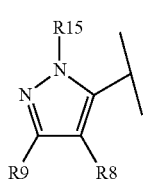

(ab) 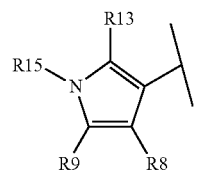

(ac) 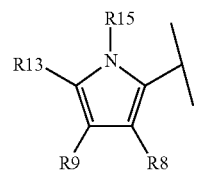

(ad) 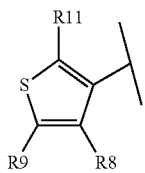

(ae) 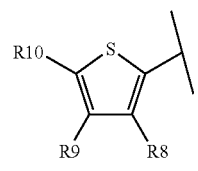

(af) 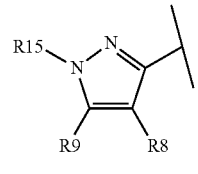

(ag) 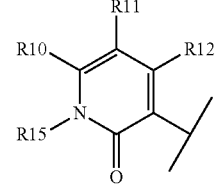

(ah) 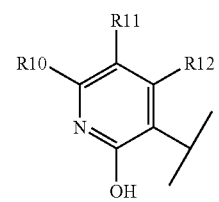

-continued (ai) 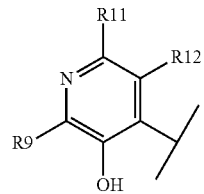

(aj) 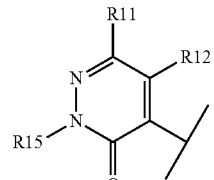

(ak) 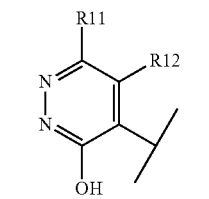

in which R7, R8, R9, R10, R11, R12, R13, R14 and R15 have the meaning given hereinafter, R5 represents a hydrogen atom, a fluorine atom, an alkyl radical having from 1 to 5 carbon atoms or a fluoroalkyl or perfluoroalkyl radical having from 1 to 5 carbon atoms, R6 represents a hydrogen atom, a —COOtBu radical or a —COOBn radical, R7 represents a halogen, or an —R16, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16 radical, R$_7$a represents a hydrogen atom or an alkyl radical having from 1 to 5 carbon atoms, R8 represents a hydrogen atom, a halogen atom, an —OH radical, or an —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently selected from the group consisting of a hydrogen, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 and —CO$_2$R16 radical, or alternatively, when two of the R9, R10, R11 and R12 radicals are in the ortho position on an aromatic or heteroaromatic ring selected from the group consisting of the rings corresponding to formulae (p) to (v), (x) and (ag) to (ak) above, then they can together form, with the bond which links them together, an aryl, heteroaryl, cycloalkyl or heterocycloalkyl ring, R13 and R14 are identical or different and are independently selected from the group consisting of a hydrogen atom, a halogen atom, and an alkyl, —CF$_3$, —OCF$_3$, —OH, —SH, —CN, —SO$_2$R16, —SO$_2$NR16R17, —NHSO$_2$NR16R17, —NR16R17, —NR16CONR16R17, —NR16COR17, —NR16CO$_2$R17, —CONR16R17, —COR16 and —CO$_2$R16 radical, R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently selected from the group consisting of a hydrogen atom, aryl, heteroaryl, arylalkyl, heteroarylalkyl, alkyl, fluoroalkyl having from 1 to 5 carbon atoms, cycloalkyl, cycloalkylalkyl, and a —CH$_2$COOR18 group in which R18 represents an alkyl radical having from 1 to 5 carbon atoms, or alternatively, when R16 and R17 are bonded to the same nitrogen atom, they form a heterocycle having between 3 and 7 ring members and optionally having one or two heteroatoms chosen from oxygen, sulfur and nitrogen in addition to the common nitrogen atom to which they are bonded, it being possible for said heterocycle to be substituted with an alkyl group having from 1 to 5 carbon atoms or a —COOR18 group in which R18 represents an alkyl radical having from 1 to 5 carbon atoms;

Y represents an oxygen atom, a sulfur atom, or a nitrogen atom substituted with an R15 radical, and Z represents a carbon or nitrogen atom.

2. The compound as claimed in claim 1, wherein, in the abovementioned formula (I):

R1 represents a hydrogen atom,

R2 represents a five-membered ring selected from the group consisting of structures (1), (2) and (3) below:

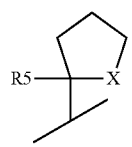
(1)

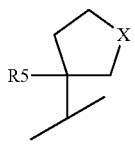
(2)

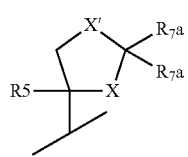
(3)

in which R5, R$_7$a, X and X' have the meaning given hereinafter,

R3 represents an aromatic or heteroaromatic ring selected from the group consisting of the rings corresponding to formulae (a), (b) and (d) below:

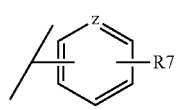
(a)

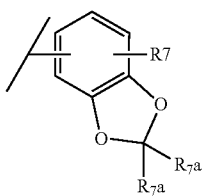
(b)

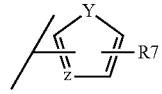
(d)

in which R7, R$_7$a, Y and Z have the meaning given hereinafter, it being specified that the rings (a), (b) and (d) can optionally bear several R7 groups, which are identical or different, the total number of such R7 groups being at most equal to the number of substitutable atoms of the ring;

R4 represents an aromatic or heteroaromatic ring selected from the group consisting of the rings corresponding to formulae (p), (q), (t), (z), (ad), (ag) and (ah) below:

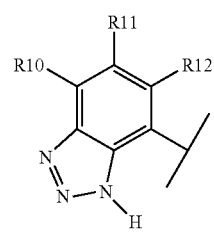
(p)

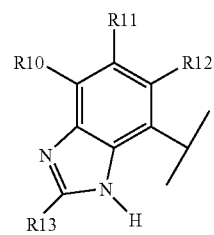
(q)

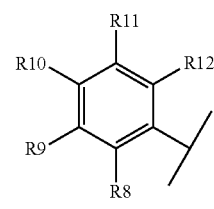
(t)

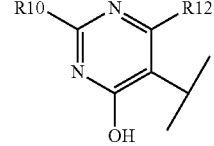
(z)

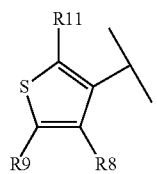
(ad)

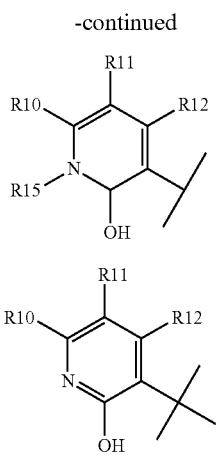

in which R8, R9, R10, R11, R12, R13 and R15 have the meaning given hereinafter,

R5 represents a hydrogen atom, a fluorine atom, an alkyl radical having from 1 to 5 carbon atoms or a fluoroalkyl or perfluoroalkyl radical having from 1 to 5 carbon atoms, R6 represents a hydrogen atom, a —COOtBu radical or a —COOBn radical, R7 represents a halogen, or an R16, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16 radical, R$_7$a represents a hydrogen or an alkyl radical having from 1 to 5 carbon atoms, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently selected from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 and —CO$_2$R16 radical, or alternatively, when two of the R9, R10, R11 and R12 radicals are in the ortho position on an aromatic or heteroaromatic ring selected from the group consisting of the rings corresponding to formulae (p), (q), (t), (ag) and (ah) above, then they can together form, with the bond which links them together, an aryl, heteroaryl, cycloalkyl or heterocycloalkyl ring, R13 is selected from the group consisting of a hydrogen atom, a halogen atom, and an alkyl, —CF$_3$, —OCF$_3$, —OH, —SH, —CN, —SO$_2$R16, —SO$_2$NR16R17, —NHSO$_2$NR16R17, —NR16R17, —NR16CONR16R17, —NR16COR17, —NR16CO$_2$R17, —CONR16R17, —COR16 and —CO$_2$R16 radical, R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently selected from the group consisting of a hydrogen atom, aryl, heteroaryl, arylalkyl, heteroarylalkyl, alkyl, fluoroalkyl having from 1 to 5 carbon atoms, cycloalkyl, cycloalkylalkyl, and a —CH$_2$COOR18 group in which R18 represents an alkyl radical having from 1 to 5 carbon atoms, or alternatively, when R16 and R17 are bonded to the same nitrogen atom, they form a heterocycle having between 3 and 7 ring members and optionally having one or two heteroatoms selected from oxygen, sulfur and nitrogen in addition to the common nitrogen atom to which they are bonded, it being possible for said heterocycle to be substituted with an alkyl group having from 1 to 5 carbon atoms or a —COOR18 group in which R18 represents an alkyl radical having from 1 to 5 carbon atoms;

X and X', which are identical or different, represent an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

3. The compound as claimed in claim 1 wherein in the abovementioned formula (I):

R1 represents a hydrogen atom,

R2 represents a ring comprising five atoms, having the structure (1) below:

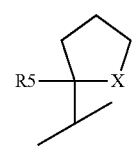

in which R5 and X have the meaning given hereinafter,

R3 represents a heteroaromatic ring corresponding to formula (d) below:

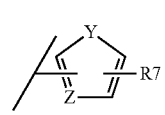

in which R7, Y and Z have the meaning given hereinafter, it being specified that the ring (d) can optionally bear several R7 groups, which can be identical or different, the total number of such R7 groups being at most equal to the number of substitutable atoms of the ring;

R4 represents an aromatic ring corresponding to formula (t) below:

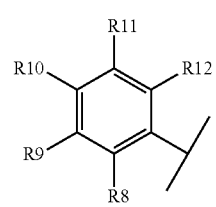

in which R8, R9, R10, R11 and R12 have the meaning given hereinafter,

R5 represents a hydrogen atom, a fluorine atom, an alkyl radical having from 1 to 5 carbon atoms or a fluoroalkyl or perfluoroalkyl radical having from 1 to 5 carbon atoms, R6 represents a hydrogen atom, a —COOtBu radical or a —COOBn radical, R7 represents a halogen atom, or an R16, —CF₃, —COR16, —OR16, —NR16R17, —NO₂, —CN, —SO₂R16, —SO₂NR16R17, —NR16COR17, —CONR16R17, —NR16CO₂R17 or —CO₂R16 radical, R8 represents a hydrogen atom, or an —OH, —SH, —CONHOR16, —CONR16OH, —NR16R17, —SO₃H, —OCOR16, —NHSO₂R16, —SO₂NR16R17, —NHCOR16, —CONR16R17, —NR16CO₂R17, —NHSO₂NR16R17, —CO₂R16, pyrrolyl, imidazolyl, triazolyl or tetrazolyl radical, R9, R10, R11 and R12 are identical or different and are independently selected from the group consisting of a hydrogen atom, a halogen atom and an alkyl, alkoxy, —CF₃, —OCF₃, —OH, —NO₂, —CN, —SO₂R16, —SO₂NR16R17, —NR16COR17, —NR16CO₂R17, —CONR16R17, —COR16 and —CO₂R16 radical, or alternatively, when two of the R9, R10, R11 and R12 radicals are in the ortho position on the aromatic ring (t), they can together form, with the bond which links them together, an aryl, heteroaryl, cycloalkyl or heterocycloalkyl ring, R15 represents a hydrogen atom or an —OH, —SO₂R16, —COR16, —CO₂R16, aryl, heteroaryl, arylalkyl, heteroarylalkyl, alkyl, cycloalkyl or cycloalkylalkyl radical, R16 and R17 are identical or different and are independently selected from the group consisting of a hydrogen atom, aryl, heteroaryl, arylalkyl, heteroarylalkyl, alkyl, fluoroalkyl having from 1 to 5 carbon atoms, cycloalkyl, cycloalkylalkyl, and a —CH₂COOR18 group in which R18 represents an alkyl radical having from 1 to 5 carbon atoms, or alternatively, when R16 and R17 are bonded to the same nitrogen atom, they form a heterocycle having between 3 and 7 ring members and optionally having one or two heteroatoms selected from the group consisting of oxygen, sulfur and nitrogen in addition to the common nitrogen atom to which they are bonded, it being possible for said heterocycle to be substituted with an alkyl group having from 1 to 5 carbon atoms and a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

4. A pharmaceutical composition comprising an effective amount of a compound, or of a pharmaceutically acceptable salt of said compound, as claimed in claim 1, in combination with a pharmaceutically acceptable solvent or support.

5. The compound as claimed in claim 1, selected from the group consisting of:

1/- 2-hydroxy-N,N-dimethyl-3-(2-{[(5-methylfuran-2-yl)-(2-methyltetrahydrofuran-2-yl)methyl]amino}-3,4-dioxocyclobut-1-enylamino)benzamide;

2/- 2-hydroxy-N,N-dimethyl-3-(2-{[(5-methylfuran-2-yl)-(tetrahydrothiophen-2-yl)methyl]amino}-3,4-dioxocyclobut-1-enylamino)benzamide;

3/- methyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate;

4/- isopropyl (S)-1[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate;

5/- ethyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate;

6/- methyl (R)-1-[2-hydroxy-3-(2-{[(5-methylfuran-2-yl)-(tetrahydrothiophen-2-yl)methyl]amino}-3,4-dioxocyclobut-1-enylamino)benzoyl]pyrrolidine-2-carboxylate;

7/- methyl (S)-1-[2-hydroxy-3-(2-{[(5-methylfuran-2-yl)-(tetrahydrothiophen-2-yl)methyl]amino}-3,4-dioxocyclobut-1-enylamino)benzoyl]pyrrolidine-2-carboxylate;

8/- 2-hydroxy-N-methyl-3-(2-{[(S)-(5-methylfuran-2-yl)tetrahydrothiophen-2-ylmethyl]amino}-3,4-dioxocyclobut-1-enylamino)-N-(2,2,2-trifluoroethyl)benzamide;

9/- methyl {[2-hydroxy-3-(2-{[(5-methylfuran-2-yl)-(tetrahydrothiophen-2-yl)methyl]amino}-3,4-dioxocyclobut-1-enylamino)benzoyl]methylamino}acetate;

10/- 6-chloro-2-hydroxy-N,N-dimethyl-3-(2-{[(5-methylfuran-2-yl)-(tetrahydrothiophen-2-yl)methyl]amino}-3,4-dioxocyclobut-1-enylamino)benzenesulfonamide;

11/- 2-hydroxy-N,N-dimethyl-3-(2-{[(R)-(5-methylfuran-2-yl)tetrahydro-furan-2-ylmethyl]amino}-3,4-dioxocyclobut-1-enylamino)benzamide;

12/- 2-hydroxy-N,N-dimethyl-3-(2-{[(S)-(5-methylfuran-2-yl)tetrahydrofuran-2-ylmethyl]amino}-3,4-dioxocyclobut-1-enylamino)benzamide;

13/- 3-(3,4-dioxo-2-{[phenyl(tetrahydrofuran-2-yl)methyl]amino}cyclobut-1-enylamino)-2-hydroxy-N,N-dimethylbenzamide;

14/- 3-(2-{[((R)-2,2-dimethyl-[1,3]dioxolan-4-yl)-(5-methylfuran-2-yl)methyl]amino}-3,4-dioxocyclobut-1-enylamino)-2-hydroxy-N,N-dimethylbenzamide;

15/ methyl (S)-1-[2-fluoro-3-(2-{[(5-methylfuran-2-yl)-(tetrahydrothiophen-2-yl)methyl]amino}-3,4-dioxocyclobut-1-enylamino)benzoyl]pyrrolidine-2-carboxylate;

16/ 3-(2-hydroxypyridin-3-ylamino)-4-{[(5-methylfuran-2-yl)-(tetrahydrothiophen-2-yl)methyl]amino}cyclobut-3-ene-1,2-dione;

17/ 3-{[(5-methylfuran-2-yl)-(tetrahydrothiophen-2-yl)methyl]-amino}-4-(1-methyl-2-oxo-1,2-dihydropyridin-3-ylamino)cyclobut-3-ene-1,2-dione;

18/ (−)-2-hydroxy-N-methyl-3-(2-{[(S)-(5-methylfuran-2-yl)-(tetrahydrothiophen-2-yl)methyl]amino}-3,4-dioxocyclobut-1-enylamino)-N-(2,2,2-trifluoroethyl)benzamide;

19/ methyl (−)-{[2-hydroxy-3-(2-{[(S)-(5-methylfuran-2-yl)-(tetrahydrothiophen-2-yl)methyl]amino}-3,4-dioxocyclobut-1-enylamino)benzoyl]methylamino}acetate;

20/ methyl (−)-1-[2-hydroxy-3-(2-{[((S)-5-methylfuran-2-yl)-(tetrahydrothiophen-2-yl)methyl]amino}-3,4-dioxocyclobut-1-enylamino)benzoyl]pyrrolidine-2-(R)-carboxylate;

21/ (−)-6-chloro-2-hydroxy-N,N-dimethyl-3-(2-{[((S)-5-methylfuran-2-yl)-(tetrahydrothiophen-2-yl)methyl]amino}-3,4-dioxocyclobut-1-enylamino)benzamide; and 22/ (−)-3-[4-chloro-2-hydroxy-3-(4-methylpiperazine-1-sulfonyl)phenylamino]-4-{[(5-methylfuran-2-yl)-(tetrahydrothiophen-2-yl)methyl]amino}-cyclobut-3-ene-1,2-dione.

6. A method of treating a patient suffering from an α-chemokine-mediated disease, the method comprising administering an effective amount of a medicament comprising the compound as claimed in claim 1.

7. A method of treating a patient suffering from an α-chemokine-mediated disease, the method comprising administering an effective amount of a pharmaceutical composition comprising the compound as claimed in claim 1.

8. The method according to claim 7, wherein the α-chemokine-mediated disease is selected from the group consisting of neutrophilic dermatosis, psoriasis, atopic dermatitis, acne, rosacea, asthma, chronic obstructive pulmonary diseases, respiratory diseases in adults, arthritis, inflammatory bowel diseases, Crohn's disease, transplant rejection, cystic fibrosis and skin cancers.

9. The method according to claim 7, wherein the α-chemokine-mediated disease is selected from the group consisting of neutrophilic dermatosis, atopic dermatitis, acne and rosacea.

10. The method according to claim 9, wherein the the α-chemokine-mediated disease is neutrophilic dermatosis in the form of psoriasis.

\* \* \* \* \*